United States Patent
Schumacher et al.

(10) Patent No.: US 11,224,469 B2
(45) Date of Patent: Jan. 18, 2022

(54) IMPLANTS AND RELATED METHODS FOR BUNION CORRECTION

(71) Applicants: PROCEPTION MEDICAL, LLC, West Caldwell, NJ (US); Josef J. Geldwert, New York, NY (US)

(72) Inventors: Brian Schumacher, Orlando, FL (US); Nicholas Slater, Chandler, AZ (US); Josef J. Geldwert, New York, NY (US)

(73) Assignee: PROCEPTION MEDICAL, LLC, West Caldwell, NJ (US)

( * ) Notice: Subject to any disclaimer, the term of this patent is extended or adjusted under 35 U.S.C. 154(b) by 139 days.

(21) Appl. No.: 16/562,961

(22) Filed: Sep. 6, 2019

(65) Prior Publication Data
US 2020/0054374 A1    Feb. 20, 2020

Related U.S. Application Data

(63) Continuation of application No. PCT/US2018/022010, filed on Mar. 12, 2018.
(Continued)

(51) Int. Cl.
*A61B 17/80* (2006.01)
*A61B 17/84* (2006.01)
(Continued)

(52) U.S. Cl.
CPC ........ *A61B 17/8061* (2013.01); *A61B 17/842* (2013.01); *A61B 17/1775* (2016.11);
(Continued)

(58) Field of Classification Search
CPC ............ A61B 17/8004; A61B 17/8061; A61B 17/8085; A61B 17/842; A61B 17/8866;
(Continued)

(56) References Cited

U.S. PATENT DOCUMENTS 3,824,995 A    7/1974 Getscher et al.
4,269,180 A    5/1981 Dall et al.
(Continued)

FOREIGN PATENT DOCUMENTS

EP    0768843    4/1997
RU    2056801 C1    3/1996
(Continued)

OTHER PUBLICATIONS

Extended European Search Report issued in corresponding European Patent Application No. 18764689.8, dated Dec. 22, 2020, 7 pages.
(Continued)

*Primary Examiner* — Marcela I. Shirsat
(74) *Attorney, Agent, or Firm* — Heslin Rothenberg Farley & Mesiti P.C.; Kristian E. Ziegler, Esq.; John W. Boger, Esq.

(57) ABSTRACT

Implants, systems and related methods for correcting bunions are disclosed. The implants, systems and methods may include a first bone engaging implant configured to couple to a first bone, and a second bone engaging implant configured to couple to a second bone that is adjacent the first bone. The implants, systems and methods may further include a flexible cable member extending between the first and second implants that allows motion between the first and second implants but for movement of the first and second implants away from each other. The length of the cable member may draw the first bone towards the second bone and decrease an angle formed between therebetween. The cable member may be rigidly or slidably coupled to the first and second implants.

20 Claims, 47 Drawing Sheets

Related U.S. Application Data

(60) Provisional application No. 62/470,137, filed on Mar. 10, 2017, provisional application No. 62/488,939, filed on Apr. 24, 2017.

(51) Int. Cl.
*A61B 17/88* (2006.01)
*A61B 17/56* (2006.01)
*A61B 17/17* (2006.01)

(52) U.S. Cl.
CPC ....... *A61B 17/8004* (2013.01); *A61B 17/8023* (2013.01); *A61B 17/8085* (2013.01); *A61B 17/8872* (2013.01); *A61B 2017/565* (2013.01)

(58) Field of Classification Search
CPC ............ A61B 17/1728; A61B 17/1775; A61B 2017/565; A61B 17/8019; A61B 17/8023
USPC ........................................................ 606/328
See application file for complete search history.

(56) References Cited

U.S. PATENT DOCUMENTS

| | | |
|---|---|---|
| 4,377,872 A | 3/1983 | Daniell, Jr. |
| 4,409,974 A | 10/1983 | Freedland |
| 5,246,443 A | 9/1993 | Mai |
| 5,415,661 A | 5/1995 | Holmes |
| 5,454,812 A | 10/1995 | Lin |
| 5,529,075 A | 6/1996 | Clark |
| 5,725,582 A | 5/1998 | Bevan et al. |
| 6,051,007 A | 4/2000 | Hogendijk et al. |
| 6,066,141 A | 5/2000 | Dall et al. |
| 6,451,019 B1 | 9/2002 | Zucherman et al. |
| 6,872,210 B2 | 3/2005 | Hearn |
| 7,235,091 B2 | 6/2007 | Thornes |
| 7,335,204 B2 | 2/2008 | Tornier |
| 7,635,365 B2 | 12/2009 | Ellis et al. |
| 7,875,058 B2 | 1/2011 | Holmes, Jr. |
| 8,246,664 B2 | 8/2012 | Terrill et al. |
| 8,257,403 B2 | 9/2012 | Den Hartog et al. |
| 8,277,459 B2 | 10/2012 | Sand et al. |
| 8,398,678 B2 | 3/2013 | Baker et al. |
| 8,425,554 B2 | 4/2013 | Denove et al. |
| 8,652,141 B2 | 2/2014 | Rush et al. |
| 8,696,716 B2 | 4/2014 | Kartalian et al. |
| 8,696,719 B2 | 4/2014 | Lofthouse et al. |
| 2002/0143336 A1 | 10/2002 | Hearn |
| 2004/0116930 A1 | 6/2004 | O'Driscoll et al. |
| 2005/0085819 A1 | 4/2005 | Ellis et al. |
| 2006/0235396 A1 | 10/2006 | Sanders et al. |
| 2006/0259076 A1 | 11/2006 | Burkhart et al. |
| 2007/0276383 A1 | 11/2007 | Rayhack |
| 2008/0208252 A1 | 8/2008 | Holmes |
| 2008/0234679 A1 | 9/2008 | Sarin et al. |
| 2009/0036893 A1 | 2/2009 | Kartalian et al. |
| 2009/0210011 A1 | 8/2009 | Den Hartog et al. |
| 2009/0275989 A1 | 11/2009 | Linares |
| 2010/0152752 A1 | 6/2010 | Denove et al. |
| 2010/0211071 A1 | 8/2010 | Lettmann et al. |
| 2010/0217328 A1 | 8/2010 | Terrill et al. |
| 2011/0077656 A1 | 3/2011 | Sand et al. |
| 2011/0093018 A1 | 4/2011 | Prasad et al. |
| 2011/0178552 A1 | 7/2011 | Biscup et al. |
| 2011/0178557 A1 | 7/2011 | Rush et al. |
| 2011/0224729 A1 | 9/2011 | Baker et al. |
| 2011/0301648 A1 | 12/2011 | Lofthouse et al. |
| 2012/0016426 A1 | 1/2012 | Robinson |
| 2013/0138150 A1 | 5/2013 | Baker et al. |
| 2014/0081336 A1 | 3/2014 | Zeetser et al. |
| 2015/0119944 A1 | 4/2015 | Geldwert |
| 2017/0079701 A1 | 3/2017 | Geldwert |

FOREIGN PATENT DOCUMENTS

| | | | |
|---|---|---|---|
| WO | 2010106507 A2 | 9/2010 | |
| WO | 2013154697 A1 | 10/2013 | |
| WO | 2013164819 | 11/2013 | |
| WO | 2015187773 A2 | 12/2015 | |
| WO | WO-2015187773 A2 * | 12/2015 | ........... A61B 17/842 |

OTHER PUBLICATIONS

Extended European Search Report for European Application No. 15803642.6 dated Dec. 15, 2017.
International Search Report and Written Opinion of the International Searching Authority for International Application No. PCT/US2013/029267 dated May 31, 2013.
International Search Report and Written Opinion of the International Searching Authority for International Application No. PCT/US2015/033893 dated Aug. 19, 2015.
International Search Report and Written Opinion of the International Searching Authority for International Application No. PCT/US2018/022010 dated May 29, 2018.

* cited by examiner

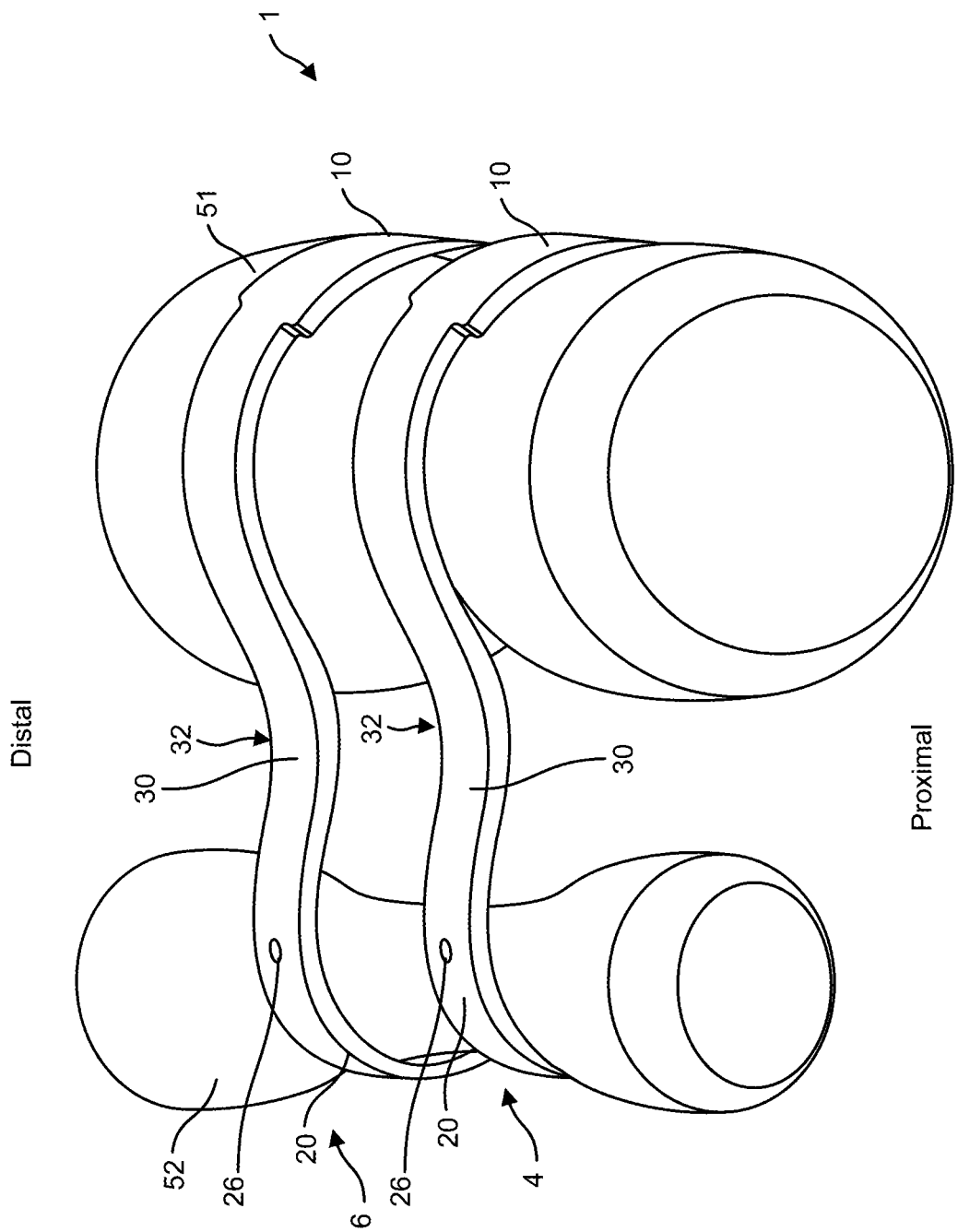

IMPLANTS AND RELATED METHODS FOR BUNION CORRECTION

CROSS-REFERENCE TO RELATED APPLICATIONS

This application is a continuation of PCT Application No. PCT/US2018/022010 filed on Mar. 12, 2018, which claimed priority benefit of U.S. Provisional Application No. 62/470,137 filed Mar. 10, 2017 and U.S. Provisional Application No. 62/488,939 filed Apr. 24, 2017, which are incorporated herein by reference in their entireties.

FIELD OF THE DISCLOSURE

Aspects herein relate to surgical implants for the correction of bunions. Methods of correcting bunions using a surgical implant are also described herein.

BACKGROUND

Hallux abducto valgus is a particular type of deformity of the foot which is more commonly referred to as a bunion. Hallux valgus is a condition or deformity in which the first metatarsal (commonly referred to as the big toe) points toward the second metatarsal or second toe, resulting in a protrusion or bony bump at the metatarsophalangeal (MTP) joint at the base of the first metatarsal. This bunion typically forms when the big toe points or pushes against the second or next toe, forcing the MTP joint of the first metatarsal to become larger and protrude laterally.

Other types of bunions (bunions involving other bones than the first metatarsal) exist. For example, a Tailor's bunion (sometimes referred to as a bunionette) is a similar condition or deformity to hallux valgus in which the fifth metatarsal or fifth toe (commonly referred to as the pinky toe) is angled toward the fourth metatarsal or fourth toe, resulting in a protrusion at the MTP joint at the base of the fifth metatarsal.

The exact cause of bunions is unknown, but is thought to be of genetic and/or hormonal etiology, and may be exacerbated by the use of constricting footwear. It has been reported that there were about 361,000 bunion-related surgeries performed in U.S. in 2014. It has also been reported that the number of bunion-related surgeries at least in the U.S. is growing at a rate of about 4% per year.

Current non-surgical treatment of bunions include externally applied devices such as orthotics, bunion pads, arch supports, and braces. Unfortunately, these treatments are typically ineffective. Current surgical procedures that correct bunions include arthroplasty, osteotomy, and arthrodesis. Conventional implantable devices for the treatment of bunions include an artificial joint that replaces all or part of the MTP joint and a suture-button construct that passes through and between the respective metatarsal bones to laterally tension the metatarsal bones together. These current surgical procedures and devices for treating bunions thereby all require or involve cutting (osteotomy) and/or drilling through the respective bone(s).

Bunion correction devices/implants and related methods that do not require bone cutting and/or bone drilling are therefore desirable. Bunion correction devices/implants and related methods that include fewer potential complications as compared to current bunion treatments are also desirable. Further, bunion correction devices/implants and related methods that utilize a simplified surgical procedure are also desirable. Still further, bunion correction devices/implants and related methods that allow for improved patient recovery times and/or address a larger number of patients and/or bunions, as compared to current bunion correction devices/implants and related methods, are desirable.

While certain aspects of conventional technologies have been discussed to facilitate disclosure of Applicant's inventions, the Applicant in no way disclaims these technical aspects, and it is contemplated that their inventions may encompass one or more conventional technical aspects.

In this specification, where a document, act or item of knowledge is referred to or discussed, the reference or discussion is not an admission that the document, act or item of knowledge or any combination thereof was, at the priority date, publicly available, known to the public, part of common general knowledge, or otherwise constitutes prior art under the applicable statutory provisions; or is known to be relevant to an attempt to solve any problem with which this specification is concerned.

SUMMARY

Briefly, the present disclosure satisfies the need for surgical bunion treatments that are not significantly invasive, do not include numerous potential complications, and involve lengthy relatively short periods.

The Applicant has found that the use of conventional bunion-correction implants gives rise to a high incidence of complications, including loosening of knots, stress fractures, stress risers, and recurrence of bunions, such as hallux valgus and/or tailor's bunions. Further, many conventional bunion-correction constructs invasively pass through the metatarsal bones, which may contribute to these complications. The Applicant has also appreciated that such complications (and/or other potential complications) may be reduced with the use of a less invasive construct, such as an implant that does not pass through the metatarsal bones. As a result, the Applicant has determined that current surgical bunion treatments unnecessarily involve lengthy recovery periods, which may discourage many potential patients from treatment.

Accordingly, the systems, implants and related methods disclosed herein may at least partially wrap around the metatarsal bones, and may be positioned on only the dorsal side thereof, rather than pass through them, thereby enabling a less invasive and more comfortable construct, for example.

In one aspect, the present disclosure provides an implant system for correcting a bunion. The system includes a first bone engaging implant configured to couple to a first bone, and a second bone engaging implant configured to couple to a second bone that is adjacent the first bone. The system further includes a flexible cable member extending between the first and second implants that allows motion between the first and second implants but for movement of the first and second implants away from each other.

In some embodiments, the length of the flexible cable member extending between the first and second implants is configured to decrease an angle and/or distance between the first and second bones, such as decreasing an angle between projections of the rays of the first and second bones. In some embodiments, length of the flexible cable member extending between the first and second implants is configured to decrease an intermetatarsal angle and/or distance between the first and second bones. In some embodiments, the first and second implants are configured to engage respective metatarsal bones of a foot of the patient. In some such embodiments, the length of the flexible cable member extending between the first and second implants is configured to decrease an intermetatarsal angle between the metatarsal bones. In some other such embodiments, the first bone is a first metatarsal bone and the second bone is a second metatarsal bone. In some embodiments, the flexible cable member is positioned between dorsal and plantar sides of the first and second bones when the first and second implants are coupled to the first and second bones, respectively.

In some embodiments, the first implant is configured to wrap partially around the first bone, and the second implant configured to wrap partially around the second bone. In some embodiments, the first implant includes a first bone engagement surface for engaging the first bone including a first portion defined by a first radius, and the second implant includes a second bone engagement surface for engaging the second bone including a portion defined by a second radius that is smaller than the first radius. In some embodiments, the first bone may include an anatomical defect (e.g., a bunion) that is to be corrected by the system. In some embodiments, the first portion has a first arc length and the second portion has a second arc length that is smaller than the first arc length.

In some embodiments, the first and second bone engaging implants further include at least one bone anchor hole configured to accept an anchoring element that anchors the implants to the respective first or second bone. In some such embodiments, the system further includes at least one bone anchoring element.

In some embodiments, the first and second implants are deformable and substantially rigid. In some embodiments, the flexible cable member allows an angle between the first and second implants to vary. In some embodiments, the flexible cable member is slidably coupled to at least one of the first and second implants. In some such embodiments, the flexible cable member forms a loop, and at least one end portion of the loop passes through at least one of the first and second implants to form at least one slidable connection. In some embodiments, the flexible cable member is rigidly coupled to at least one of the first and second implants. In some embodiments, the flexible cable member is rigidly coupled to one of the first and second implants and slidably coupled to the other of the first and second implants.

In another aspect, the present disclosure provides a kit for repositioning a first and second bone relative to each other. The kit may include an implant system (such as the implant system described above) and an inserter. In some embodiments, the kit may further include additional first and second implants of differing sizes. In this way, the kit may allow for customization of the system based on the particular anatomy of a patient.

In another aspect, the present disclosure provide a method of repositioning a first bone relative to a second bone, such as to a more anatomically correct position to treat a bunion formed by the first bone. The method includes coupling a first bone engaging implant to the first bone, and coupling a second bone engaging implant to a second bone adjacent the first bone. The method also includes coupling a flexible cable member between the first and second implants such that the first bone is drawn towards the second bone. The flexible cable member allows motion between the first and second bones but for movement away from each other.

In some embodiments, drawing the first bone toward the second bone decreases an angle formed between the first and second bones. In some embodiments, when the cable member is coupled between the first and second implants, the flexible cable member allows an angle between the first and second implants to vary. In some embodiments, the first and second implants are coupled to respective metatarsal bones of a foot of a patient. In some such embodiments, drawing the first bone toward the second bone decreases an intermetatarsal angle between the metatarsal bones. In some other such embodiments, the first bone is a first metatarsal bone and the second bone is a second metatarsal bone. In some embodiments, when the cable member is coupled between the first and second implants and the first and second implants are coupled to the first and second bones, respectively, the cable member is positioned between dorsal and plantar sides of the first and second bones.

In some embodiments, the first implant wraps partially around the first bone when coupled thereto, and the second implant wraps partially around the second bone when coupled thereto. In some embodiments, the first implant includes a first bone engagement surface for engaging the first bone including a first portion defined by a first radius, and the second implant includes a second bone engagement surface for engaging the second bone including a portion defined by a second radius that is smaller than the first radius. In some such embodiments, the first portion has a first arc length and the second portion has a second arc length that is smaller than the first arc length.

In some embodiments, the first and second implants further include at least one bone anchor hole configured to accept an anchoring element that coupled the implants to the respective first or second bone. In some such embodiments, the method further includes driving at least one anchoring element through a bone anchor hole of the first implant and into the first bone to couple the first implant to the first bone, and driving at least one anchoring element through a bone anchor hole of the second implant and into the second bone to couple the second implant to the second bone.

In some embodiments, the method further includes deforming at least one of the first and second implants to the anatomical shape of a portion of the respective first or second bone. In some embodiments, the cable member is coupled between the first and second implants prior to coupling the first bone engaging implant to the first bone and/or coupling the second bone engaging implant to a second bone. In some embodiments, the cable member is coupled between the first and second implants after at least one of coupling the first bone engaging implant to the first bone and coupling the second bone engaging implant to a second bone.

In some embodiments, coupling the cable member between the first and second implants includes slidably coupling the cable member to at least one of the first and second implants. In some such embodiments, the flexible cable member forms a loop, and coupling the cable member between the first and second implants includes passing at least one end portion through at least one of the first and second implants to form at least one slidable connection. In some embodiments, coupling the cable member between the first and second implants includes rigidly coupling the cable member to at least one of the first and second implants. In some embodiments, coupling the cable member between the first and second implants includes rigidly coupling the cable member to one of the first and second implants and slidably coupling the cable member to the other of the first and second implants.

According to another aspect, an implant for repositioning bones of a patient to a more anatomically correct position is provided. In some embodiments, implant includes a first bone engaging feature configured to wrap partially around the first bone, a second bone engaging feature configured to wrap partially around the second bone, and an intermediate portion connecting the first and second bone engaging features, the intermediate portion and the bone engaging features cooperating to enable the first bone to be drawn toward the second bone.

According to another aspect, a method of repositioning bones of a patient to a more anatomically correct position is provided. In some embodiments, the method includes engaging a first bone engaging feature to a first bone such that the first bone engaging feature partially wraps around the first bone, engaging a second bone engaging feature to a second bone such that the second bone engaging feature partially wraps around the second bone, and drawing the first bone toward the second bone with an intermediate portion that connects the first and second bone engaging features.

According to another aspect, an implant for repositioning bones of the patient to a more anatomically correct position is provided. In some embodiments, the implant includes a first bone engaging feature configured to engage a first bone, a second bone engaging feature configured to engage a second bone, an intermediate portion connecting the first and second bone engaging features, the intermediate portion and the bone engaging features cooperating to enable the first bone to be drawn toward the second bone, wherein the intermediate portion is arranged such that, when the implant is engaged with the first and second bones, the intermediate portion is located only dorsal to metatarsals of a foot of the patient.

According to another aspect, an implant for repositioning bones of the patient to a more anatomically correct position is provided. In some embodiments, the implant includes a first bone engaging feature configured to wrap partially around a first bone, a second bone engaging feature configured to wrap partially around a second bone and an intermediate portion connecting the first and second bone engaging features. In some embodiments, the intermediate portion and the bone engaging features cooperate to enable the first bone to be drawn toward the second bone. In some embodiments, the intermediate includes a flexure feature that permits relative movement of the first and second bone engaging features.

According to another aspect, an implant for repositioning bones of the patient to a more anatomically correct position is provided. In some embodiments, the implant includes a first bone engaging feature configured to engage a first bone, a second bone engaging feature configured to engage a second bone and an intermediate portion connecting the first and second bone engaging features. In some embodiments, the intermediate portion and the bone engaging features cooperate to enable the first bone to be drawn toward the second bone. In some embodiments, the intermediate includes a flexure feature that permits relative movement of the first and second bone engaging features. In some embodiments, the intermediate portion is adapted to be positioned substantially dorsal or ventral to the first and second bones when the implant is engaged with the first and second bones.

According to another aspect, an implant for repositioning bones of the patient to a more anatomically correct position is provided. In some embodiments, the implant includes a first bone engaging feature configured to engage a first bone, a second bone engaging feature configured to engage a second bone and an intermediate portion connecting the first and second bone engaging features. In some embodiments, the intermediate portion and the bone engaging features cooperate to enable the first bone to be drawn toward the second bone. In some embodiments, the intermediate portion is constructed and arranged such that, when the implant is engaged with the first and second bones, the intermediate portion is positioned substantially between the first and second bones without any portion of the implant passing entirely through either the first or second bones.

According to another aspect, an implant for repositioning bones of the patient to a more anatomically correct position is provided. In some embodiments, the implant includes a first bone engaging feature configured to engage a first bone, a second bone engaging feature configured to engage a second bone and an intermediate portion connecting the first and second bone engaging features. In some embodiments, the intermediate portion and the bone engaging features cooperate to enable the first bone to be drawn toward the second bone. In some embodiments, the first bone anchor hole is positioned on the first bone engaging feature to permit the first bone anchor to be angled relative to a vertical plane that bisects the first bone through dorsal and ventral sides of the first bone.

The bunion correction implants, systems and methods of the present disclosure may address one or more of the problems and deficiencies of the art discussed above. However, it is contemplated that the bunion correction implants, systems and methods of the present disclosure may prove useful in addressing other problems and deficiencies in a number of technical areas. Therefore, the disclosed and claimed inventions should not necessarily be construed as limited to addressing any of the particular problems or deficiencies discussed herein.

Certain embodiments of the presently-disclosed bunion correction implants, systems and methods have several features, no single one of which is solely responsible for their desirable attributes. Without limiting the scope of the bunion correction implants, systems and methods of the present disclosure (e.g., those that are defined by the claims that follow), their more prominent features will now be discussed briefly. After considering this discussion, and particularly after reading the section of this specification entitled "Detailed Description," one will understand how the features of the various embodiments disclosed herein provide a number of advantages over the current state of the art.

These and other features and advantages of this disclosure will become apparent from the following detailed description of the various aspects of the disclosure taken in conjunction with the appended claims and the accompanying drawings.

BRIEF DESCRIPTION OF DRAWINGS

The accompanying drawings are not intended to be drawn to scale. In the drawings, each identical or substantially similar component that is illustrated in various figures is represented by a like numeral. For purposes of clarity, not every component may be labeled in every drawing. Various embodiments of the disclosure will now be described, by way of example, with reference to the accompanying drawings, in which:

FIG. 37A depicts an elevational perspective view of metatarsal bones with the bunion correction implant system of FIG. 35;

DETAILED DESCRIPTION

Figure 1A:
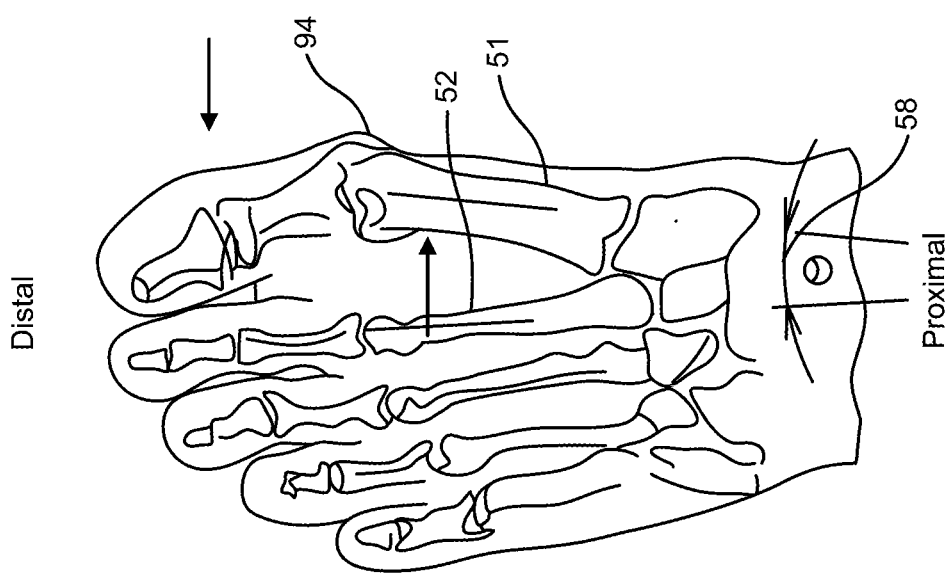
FIG. 1A illustrates a top view of a healthy foot without a hallux valgus bunion.

Aspects of the present disclosure and certain features, advantages, and details thereof, are explained more fully below with reference to the non-limiting embodiments illustrated in the accompanying drawings. Descriptions of well-known materials, fabrication tools, processing techniques, etc., are omitted so as to not unnecessarily obscure the inventions in detail. It should be understood, however, that the detailed description and the specific example(s), while indicating embodiments of inventions, are given by way of illustration only, and are not by way of limitation. Various substitutions, modifications, additions and/or arrangements within the spirit and/or scope of the underlying inventive concepts will be apparent to those skilled in the art from this disclosure.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. In addition, for the purposes of this disclosure when referencing the device, the term "proximal" will mean the portion of the device closest or nearest the insertion instrument. The term "distal" shall mean the portion of the device farthest away from the insertion instrument. The terms osteosynthesis, osteotomy and the like are used herein to refer to the promotion of bone formation/growth and bone in-growth, as explained further below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Any examples of parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein.

Any examples of parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein.

Hallux valgus and tailor's bunions have a wide variety of causes. Some deformities may be inherited or present at birth, while others develop later and/or are self-inflicted, for example. Self-inflicted causes may include high-heeled or ill-fitting shoes, high-impact exercise, foot injuries, and the like. As used herein, the top side of the foot will be referred to as the dorsal side and the bottom side of the foot will be referred to as plantar side or ventral side. Thus, a top facing surface of the implant may be referred to as the dorsal side and the bottom facing surface of the implant may be referred to as the plantar side or ventral side. In either case, as will be appreciated below, the implant in some embodiments will be positioned on the top side of the metatarsals such that the plantar side (or ventral side) of the implant faces the dorsal side of the metatarsals and the plantar side of the metatarsals is void of the implant.

Figure 1B:
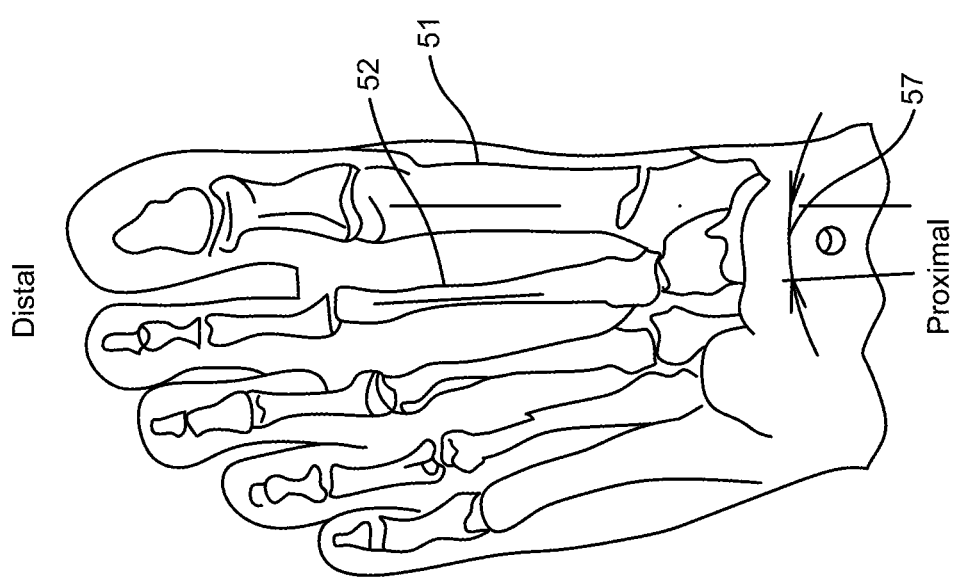
FIG. 1B illustrates a top view of a foot exhibiting a hallux valgus bunion.

FIG. 1A depicts a healthy foot while FIG. 1B depicts a foot exhibiting a hallux valgus type bunion. A hallux valgus-type bunion may develop when the pressures of bearing and shifting of weight fall unevenly on the joints and tendons in the feet, for example. This imbalance and pressure may make the metatarsophalangeal (MTP) or big toe joint unstable, leading to splaying of the first 51 and second 52 metatarsals, resulting in a protrusion 94 at the MTP joint of the first metatarsal 51 as shown in FIG. 1B. As shown in FIG. 1A, in a normal foot, the intermetatarsal angle 57 between the first 51 and second 52 metatarsal bones is typically less than about 9 degrees. As shown in FIG. 1B, a foot exhibiting hallux valgus bunion may include an intermetatarsal angle 58 between the first 51 and second 52 metatarsal bones greater than that of a normal foot, such as within the range of about 9 to about 20 degrees. The systems, implants and related methods of the present disclosure may bring or draw the first metatarsal 51 towards the second metatarsal 52 from the hallux valgus type bunion arrangement in FIG. 1B, resulting in a more anatomically correct intermetatarsal angle 57 resembling that of the healthy foot in FIG. 1A.

Figures 2A, 2B:
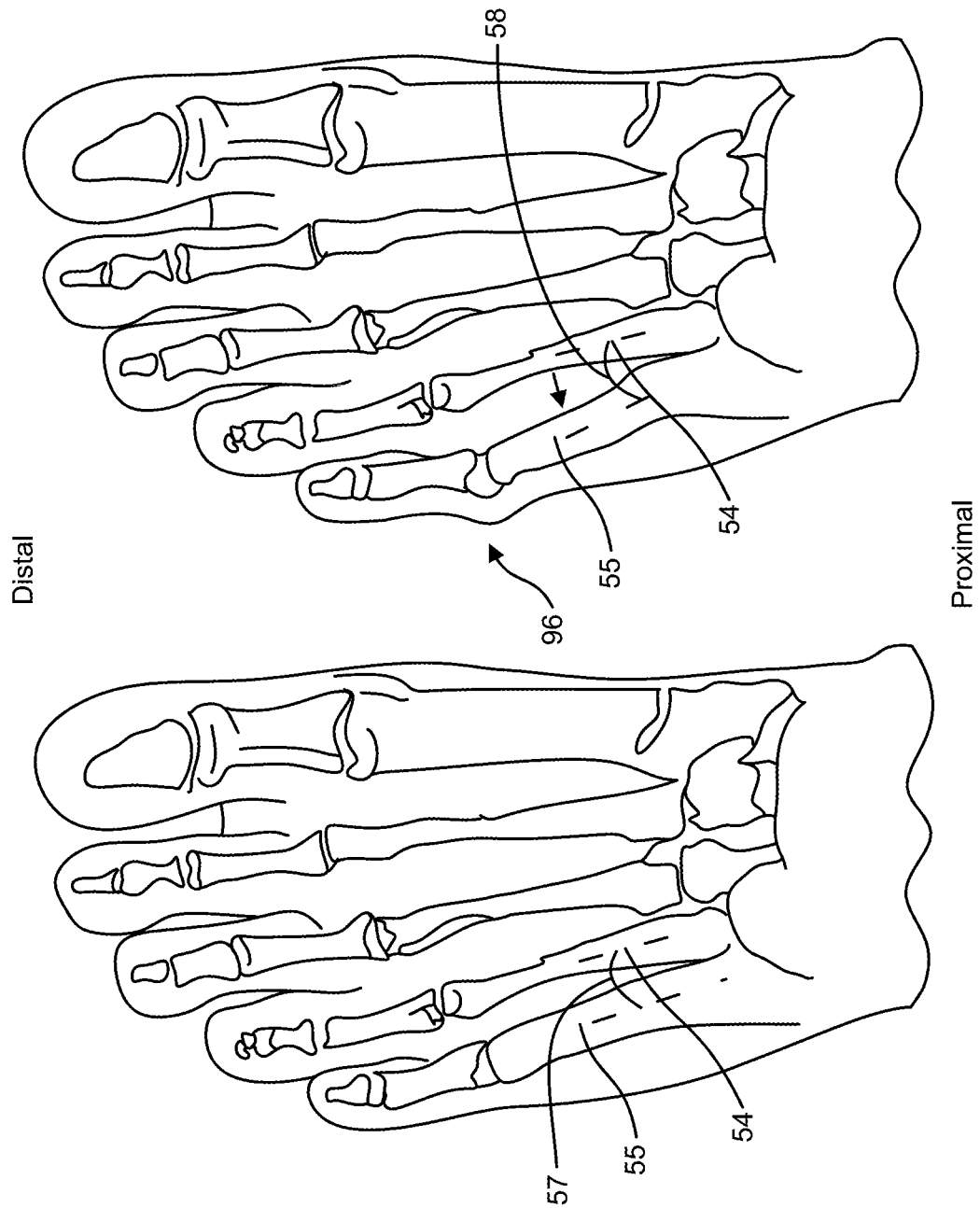
FIG. 2A illustrates a top view of a healthy foot without a tailor's bunion.
FIG. 2B illustrates a top view of a foot exhibiting a tailor's bunion.
Figure 3:
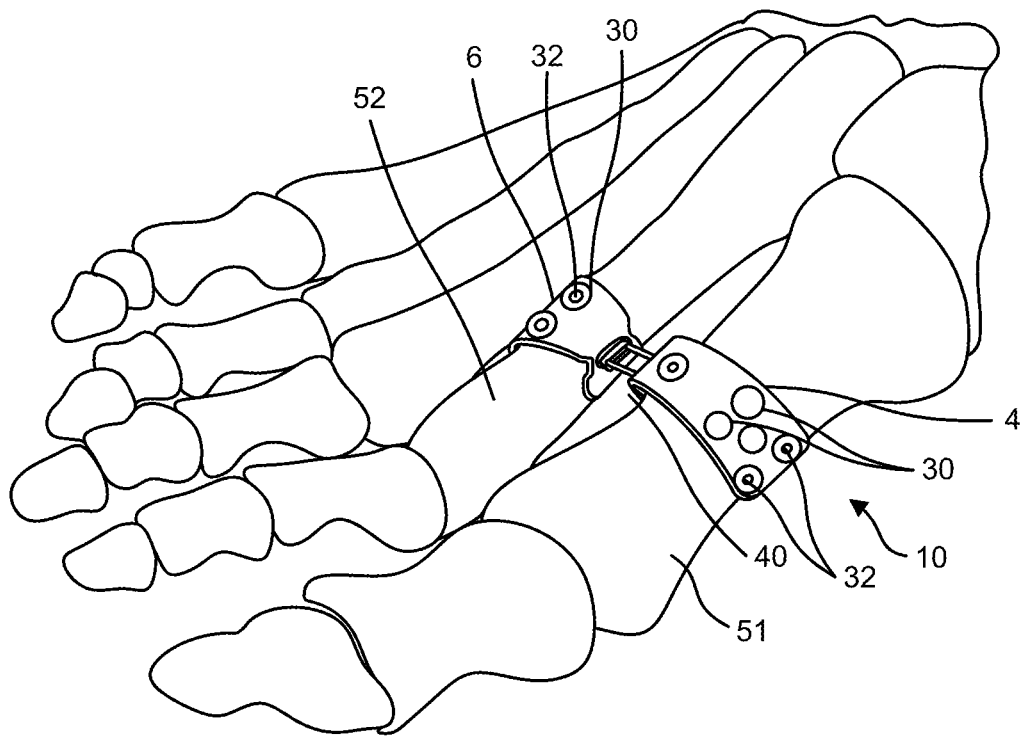
FIG. 3 illustrates an elevational perspective view of an exemplary implant system of the present disclosure coupled to first and second metatarsal bones to correct a hallux valgus bunion.
Figure 4:
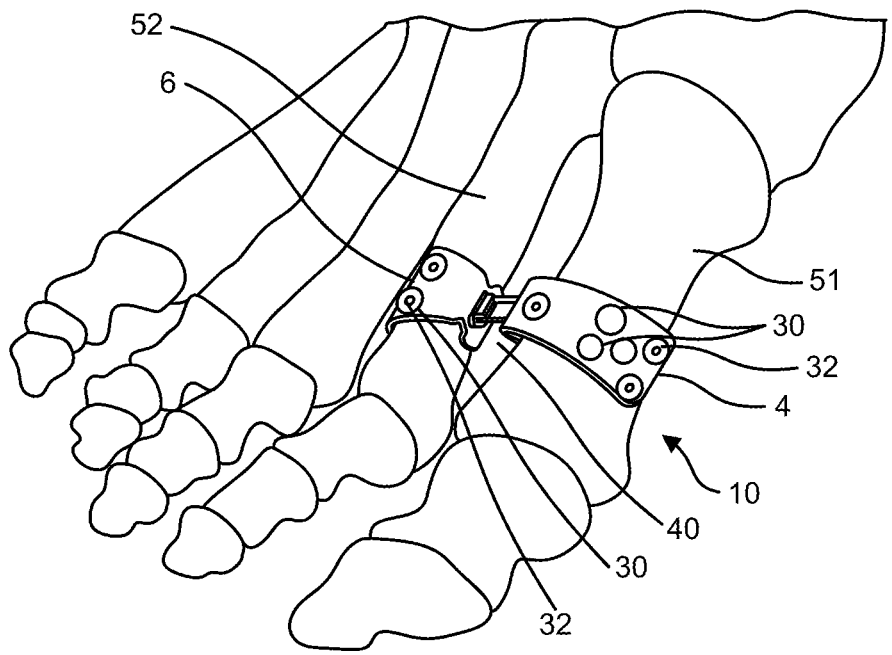
FIG. 4 illustrates another elevational perspective view of the exemplary implant system of FIG. 1 correcting a bunion.
Figure 5:
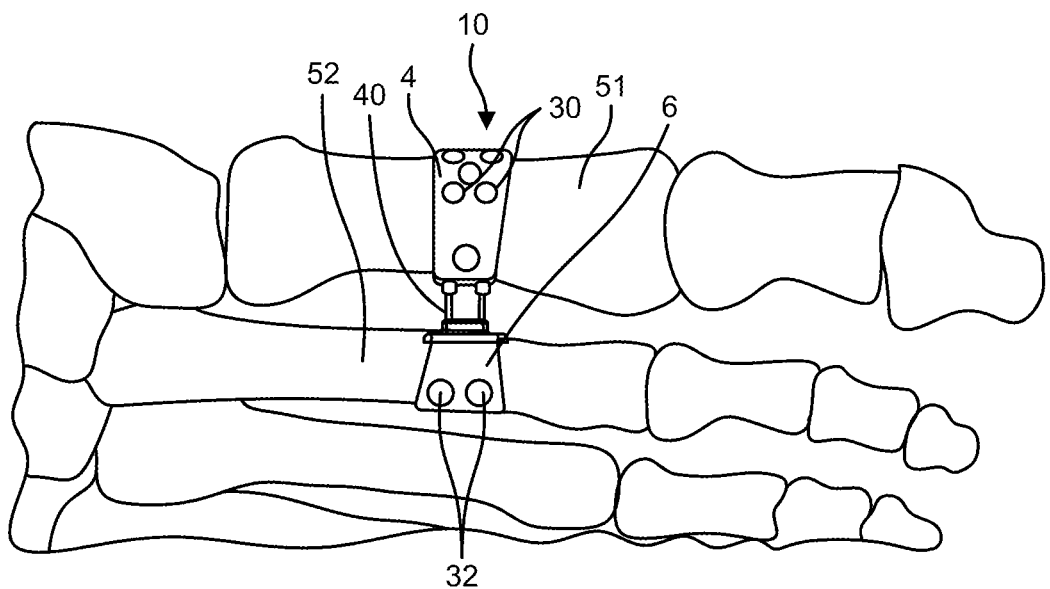
FIG. 5 illustrates a top view of the exemplary implant system of FIG. 1 correcting a bunion.
Figure 6:
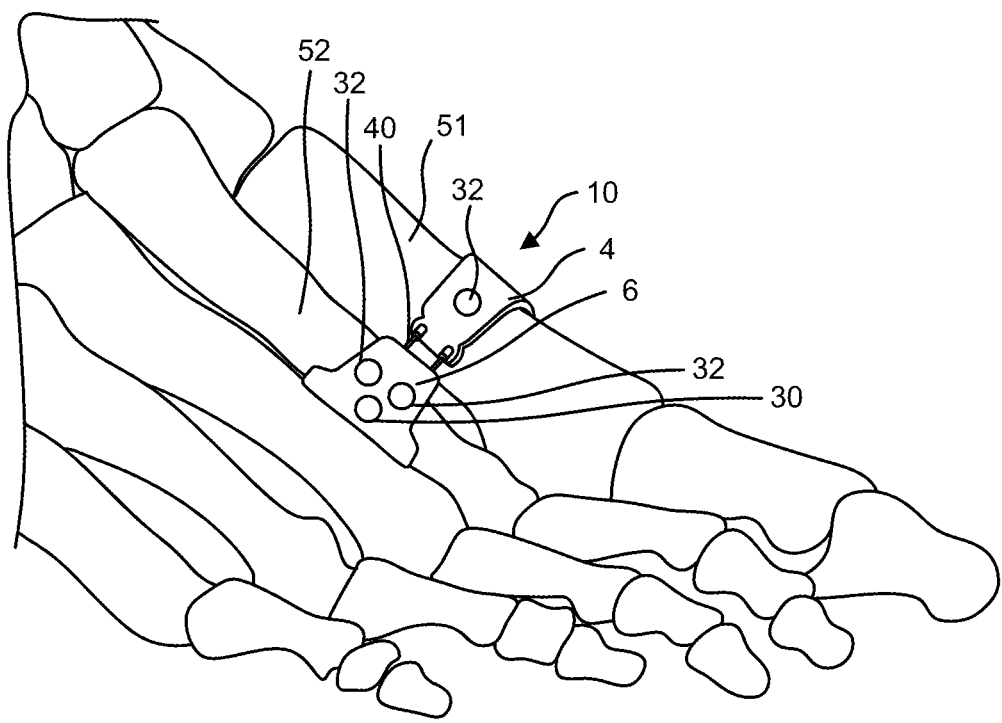
FIG. 6 illustrates another elevational perspective view of the exemplary implant system of FIG. 1 correcting a bunion.

Similarly, tailor's bunion involves instability of the fifth metatarsal that leads to splaying of the fourth and fifth metatarsals. FIG. 2A depicts a healthy foot while FIG. 2B depicts a foot with tailor's bunion. With tailor's bunion, splaying of the fourth 54 and fifth 55 metatarsal results in a protrusion 96 at the MTP joint of the fifth metatarsal. As shown in FIG. 2A, in a normal foot, the intermetatarsal angle 57 between the fourth 54 and fifth 55 metatarsal bones is typically less than about 8 degrees. As shown in FIG. 2B, a foot with tailor's bunion has an intermetatarsal angle 58 between the fourth 54 and fifth 55 metatarsal bones greater than that of a normal foot, ranging from about 8 to 15 degrees.

While particular bunion correction implants, systems and related methods of the present disclosure may be described and/or illustrated with respect to a hallux valgus type bunion, the systems, implants and related methods of the present disclosure may equally apply or be utilized to correct or treat a tailor's bunion. For example, the systems, implants and related methods of the present disclosure may bring or draw the fifth metatarsal towards the fourth metatarsal rather than drawing the first metatarsal towards the second metatarsal, resulting in a more anatomically correct intermetatarsal angle resembling that of a healthy foot. Similarly, while particular bunion correction implants, systems and related methods of the present disclosure may be described and/or illustrated with respect to a tailor's bunion, the systems, implants and related methods of the present disclosure may equally apply or be utilized to correct or treat a hallux valgus type bunion. For example, the systems, implants and related methods of the present disclosure may bring or draw the first metatarsal towards the second metatarsal rather than drawing the fifth metatarsal towards the fourth metatarsal resulting in a more anatomically correct intermetatarsal angle resembling that of a healthy foot.

One challenge with the use of prior bunion correction constructs is their attachment to the involved foot bones. Such prior implants anchor to the foot bones by fully penetrating through the bones and/or wrapping completely around the bones. Arrangements that penetrate completely through the foot are invasive, and they may weaken the structural integrity of the bones and lead to stress fractures, stress risers and other post-operative complications. Arrangements that wrap completely around the metatarsals may also require invasive surgical procedures because of their size resulting in soft tissue complications to the patient, and they may weaken the structural integrity of the bones and lead to stress fractures and stress risers. Arrangements that wrap completely around the metatarsals may also be bulky and uncomfortable to the patient.

According to one aspect of the present disclosure, surgical systems, implants and related methods are provided that partially wrap around a bone, such as a metatarsal bone, rather than penetrate completely through the entire bone or wrap completely around the bone. Further, the implants may be positioned on only the dorsal side of the bones, allowing the implant to engage the bones through a less invasive surgical procedure.

According to one aspect of the present disclosure, as shown in FIGS. 3-12 the surgical systems, implants and related methods 10 include first and second implants 4, 6 that each includes one or more feature that enables attachment or coupling of the first and second bone engaging implants 4, 6 to corresponding first and second bones 51, 52, such as adjacent first and second metatarsal bones 51, 52 in a hallux valgus type bunion arrangement as depicted in FIG. 1B (or fourth and fifth metatarsal bones 54, 55 in a tailor's type bunion arrangement as depicted in FIG. 2B (not shown)). In this manner, the system or implant 10 can exert an appropriate force on the first and second bones 51, 52 to urge the first bone 51 into its correct anatomical position. As shown in FIGS. 3-6, in one embodiment the first bone engaging implant 4 may be configured to engage and couple to a dorsal portion of the first bone 51, and the second bone engaging implant 6 may be configured to engage and couple to a dorsal portion of the second bone 52. The first and second implants 4, 6 may be formed from at least one biocompatible material. The first and second implants 4, 6 may be of one-piece construction or monolithic.

As shown in FIGS. 3-11, the first and second bone engaging implants 4, 6 may each be shaped such that the first and second implants 4, 6, including a bottom bone engaging surface thereof, is configured (e.g., shaped and sized) to substantially correspond to the shape of a portion of a cortex of the first and second bones 51, 52, respectively, to engage therewith. In some embodiments, the bone engaging surface of the first and second bone engaging implants 4, 6 may be configured to partially wrap around the respective first and second bones 51, 52. In the embodiment shown in FIGS. 3-11, the first and second implants 4, 6 each form a generally C-shape, for example, to extend over at least a portion of the dorsal, medial and lateral portions or aspects of the respective first and second bones 51, 52. The first and second implants 4, 6 may thereby hook on the lateral or medial aspect of a bone. In some embodiments, at least a portion of the engagement surface of the first and/or second implants 4, 6 may include a surface roughness or other mechanism to enhance the friction between the first and/or second implants 4, 6 and the respective first and second bones 51, 52. In some embodiments, at least a portion of the engagement surface of the first and/or second implants 4, 6 may include areas of surface roughness or other suitable features or materials that encourage growth of tissue into the implants 4, 6 to help the integration of the implants 4, 6 into the body. Examples of possible surface treatments for promotion of a surface roughness and/or tissue ingrowth include, but are not limited to: plasma etching, sand blasting, machining and other treatments to roughen the surface or otherwise provide a suitable surface texture. Alternatively, or in addition, the implants 4, 6 may include certain features and/or materials in desired locations that resist tissue attachment to help prevent immobilization. In some embodiments, the surface roughness or other surface treatment is applied only to the underside surface of the implants 4, 6 that contacts or engages the bones, and not to the top surface of the implants 4, 6 facing away from the bones.

In some embodiments, the implants 4, 6 may include other types of bone engaging features such as anchor holes. Anchoring elements may be passed through the anchor holes and fixed into the bone, thereby anchoring the implants 4, 6 to respective bones. Anchoring elements include bone screws, surgical screws, orthopedic screws, barbs, and other suitable hardware, as this aspect is not limited in this regard. In addition, screws may be of the locking or non-locking type, as this aspect is not limited in this regard.

In some embodiments, the implants 4, 6 may include other types of or additional bone engaging features that enhances attachment of the implants 4, 6 to bones. Other types of bone engaging features may include bonding or cementation that adheres the implants 4, 6 to a bone. Such bonding or cementation may be applied at any contacting interface between the implants 4, 6 and the bones.

At least the bone engagement surface of the first and second implants 4, 6 may include a at least one bone engaging portion with a radius of curvature and arc length, as discussed further below. Each bone engaging portion of the first and second implants 4, 6 may have a specific radius of curvature and arc length. The radius of curvature and arc length of each portion of the bone engagement surfaces of the first and second implants 4, 6 may allow each implant 4, 6 to hook onto or make intimate contact with the dorsal, medial and lateral aspects of the respective first and second bones 51, 52, and may mimic the shape and size of the outer surface of the respective first and second bones 51, 52.

In some embodiments, the radius of curvature of each bone engaging surface or feature of the first and second implants 4, 6 may range from about 1 mm to 25 mm. In some embodiments, the arc length of each bone engaging surface or feature of the first and second implants 4, 6 may range from about 1 mm to about 150 mm. As shown in FIGS. 4-7, the first implant 4 of the proximal implant 4 may hook on the medial aspect of the first metatarsal 51 and partially wrap around the first metatarsal 51. Similarly, as also shown in FIGS. 4-7, the second implant 6 may hook on the lateral aspect of the second metatarsal 52 and partially wraps around the second metatarsal 52. Depending on its radius of curvature and arc length, the bone engaging feature may partially wrap around bone by extending to a certain dorsal-ventral depth along the lateral or medial aspect of the bone. In some embodiments, as shown in FIGS. 4-7, the first implant 4 may partially wrap around the first metatarsal 51 or another bone by extending down to more than half the dorsal-ventral depth of the medial aspect of the first metatarsal 51 or other bone. In some embodiments, the first and second implants 4, 6 may partially wrap around a bone by extending to slightly more than half the dorsal-ventral depth, half the dorsal-ventral depth, slightly less than half the dorsal-ventral depth, or less than half the dorsal-ventral depth of the lateral or medial aspect of the bone. In some embodiments, the first and second implants 4, 6 may also be shaped to fit the medial-lateral contours of a bone. For example, in one embodiment a distal portion of the first implant 4 may curve inward medially (not shown) to meet the first metatarsal 51. Of course, it should be appreciated that the first and second implants 4, 6 are not limited in this respect and other suitable shapes may be employed. For example, the first and second implants 4, 6 may be formed in a semi-circular shape or otherwise have a longer arc length to wrap further, but still partially, around respective bones. In some cases, the first and second implants 4, 6 may be arranged to wrap completely around respective bones.

Figure 9:
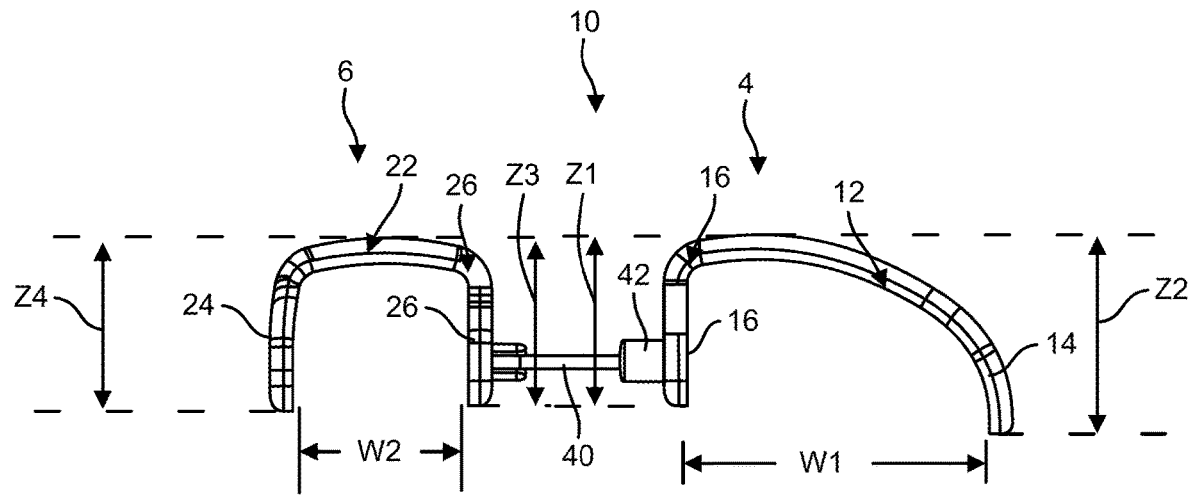
FIG. 9 illustrates a side view of the implant system of FIG. 7.

As shown in FIG. 9, the first implant may include an arcuate intermediate portion 12 that connects between an outer portion 14 and an inner portion 16. The outer portion 14, intermediate portion 12 and inner portion 16 may be configured to engage at least a portion of the lateral, dorsal and medial sides, aspects or portions of the first bone 51, respectively, such as a first metatarsal bone. In some embodiments, at least the bone engagement surface of the inner portion 16 may extend in a dorsal-plantar direction, such as for an arc length within the range of about 3 mm to about 9 mm, such as about 6 mm. In some embodiments, the at least the engagement surface of the inner portion 16 may be substantially flat or planar. In some embodiments, at least the engagement surface of the outer portion 14 may be arcuate and/or concave and extend generally in a dorsal-plantar direction. In some embodiments, at least the engagement surface of the outer portion 14 may be defined by a radius within the range of about 3 mm to about 10 mm (or about 5 mm to about 8 mm) and define an arc length within the range of about 3 mm to about 7 mm (or about 4 mm to about 6 mm) As shown in FIG. 9, the outer portion 14 of the first implant 4 may extend further in a plantar direction than the inner portion 16.

In some embodiments, at least the engagement surface of the intermediate portion 12 may be arcuate and/or concave and extend generally extend in a medial-lateral direction. In some embodiments, at least the engagement surface of the intermediate portion 12 may be defined by a radius within the range of about 10 mm to about 17 mm (or about 13 mm to about 14 mm), and define an arc length within the range of about 8 mm to about 18 mm (or about 11 mm to about 15 mm). The engagement surface of the first implant 4 may thereby form a concave surface that defines a first width W1 between the ends of the inner portion 16 and the outer portion 14 in a medial-lateral direction. In some embodiments, the first width W1 of the engagement surface of the first implant 4 may be within the range of about 11 mm to about 18 mm (or about 13 mm to about 16 mm). However, although the first implant 4 may be substantially rigid, in some embodiments the first implant 4 may be deformable such that the shape of the engagement surface may be formed into any shape or configuration to suit a particular first bone 51.

As shown in FIG. 9, the transitions between (e.g., join) the intermediate portion 12 and the outer portion 14 and the inner portion 16 of the first implant 4 may be curved. These transitions may comprise an inflection point at which the curvature of the first implant 4 changes direction. It should be understood that an object, such as a plate, can have a radius of curvature of zero, in which case the object is flat. In some embodiments, the transition areas of the first implant 4 may be a bend that is, or is close to, 90 degrees, greater than 90 degrees, or less than 90 degrees. Each of the transitions of the first implant 4 may have a radius of curvature. In some embodiments, the radius of curvature for each transition of the first implant 4 may fall within one of the following ranges: 1 to 10 mm, 0.1 to 5 mm, 0.5 to 3 mm, 0.5 to 2 mm, 0.5 to 1 mm, or 0.01 to 1 mm. Each of the radii of curvature of the transitions of the first implant 4 may fall within the same or different ranges.

Similar to the first implant 4, the second implant 6 may include an arcuate intermediate portion 22 that extends between an outer portion 24 and an inner portion 26, as shown in FIG. 9. The outer portion 24, intermediate portion 22 and inner portion 26 may be configured to engage at least a portion of the lateral, dorsal and medial sides, aspects or portions of the second bone 52, respectively, such as a second metatarsal bone that is adjacent to the first metatarsal bone that the first implant 4 engages.

In some embodiments, at least the engagement surface of the inner portion 26 may extend in a dorsal-plantar direction, such as for an arc length within the range of about 3 mm to about 9 mm (e.g., be about 6 mm). In some embodiments, at least a portion of at least the engagement surface of the inner portion 26 may be substantially flat or planar, or may be arcuate or concave. In some embodiments, at least a portion of at least the engagement surface of the outer portion 24 may be substantially flat or planar. In some embodiments, at least a portion of at least the engagement surface of the outer portion 24 may be arcuate and/or concave and extend generally extend in a dorsal-plantar direction. In some embodiments, at least a portion of at least the engagement surface of the outer portion 24 may be defined by a radius of at least about 10 mm (or at least about 15 mm), and define an arc length within the range of about 1 mm to about 10 mm (or about 2 mm to about 3 mm). In some embodiments, at least the engagement surface of the outer portion 24 may include a substantially flat or planar portion and an arcuate and/or concave portion, with a total length within the range of about 3 mm to about 10 mm (or about 6 mm to about 8 mm.) As shown in FIG. 9, the outer portion 24 of the second implant 6 is longer in a plantar direction than the inner portion 16. In some other embodiments, the engagement surface of the outer portion 24 may be substantially planar.

In some embodiments, at least the engagement surface of the intermediate portion 22 may be flat. In some embodiments, at least the engagement surface of the intermediate portion 22 may be arcuate and/or concave and extend generally extend in a medial-lateral direction. In some embodiments, at least the engagement surface of the intermediate portion 22 may be defined by a radius of at least about 10 mm (or within the range of about 14 mm to about 17 mm), and define an arc length within the range of about 3 mm to about 11 mm (or about 6 mm to about 7 mm). The engagement surface of the second implant 6 may thereby form a concave surface that defines a second width W2 between the ends of the inner portion 26 and the outer portion 24 in a medial-lateral direction. In some embodiments, the second width W2 of the engagement surface of the second implant 6 may be within the range of about 5 mm to about 11 mm (or about 7 mm to about 9 mm). However, although the second implant 6 may be substantially rigid, in some embodiments the second implant 6 may be deformable such that the shape of the engagement surface may be formed into any shape or configuration to suit a particular second bone 52.

As shown in FIG. 9, the transitions between (e.g., join) the intermediate portion 22 and the outer portion 24 and the inner portion 26 of the second implant 6 may be curved. These transitions may comprise an inflection point at which the curvature of the second implant 6 changes direction. It should be understood that an object, such as a plate, can have a radius of curvature of zero, in which case the object is flat. In some embodiments, the transition areas of the second implant 6 may be a bend that is, or is close to, 90 degrees, greater than 90 degrees, or less than 90 degrees. Each of the transitions of the second implant 6 may have a radius of curvature. In some embodiments, the radius of curvature for each transition of the second implant 6 may fall within one of the following ranges: 1 to 10 mm, 0.1 to 5 mm, 0.5 to 3 mm, 0.5 to 2 mm, 0.5 to 1 mm, or 0.01 to 1 mm. Each of the radii of curvature of the transitions of the second implant 6 may fall within the same or different ranges.

Figure 10:
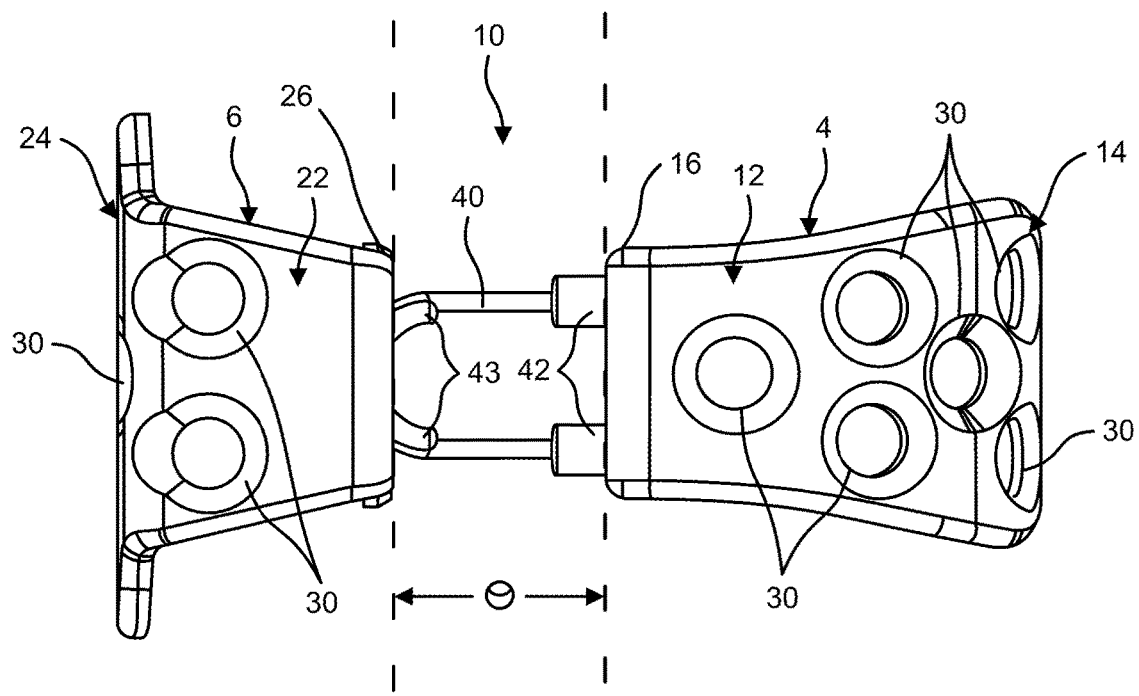
FIG. 10 illustrates a top view of the implant system of FIG. 7.

In some embodiments, the length of the implants 4, 6 in a distal-proximal direction may vary. As shown in FIG. 10, the outer portion 14 of the first implant 4 may be longer or wider in the distal-proximal direction than the intermediate portion 12, and the intermediate portion 12 may be longer or wider in the distal-proximal direction than the inner portion 16. However, the length or width of the first implant 4 may vary and may be configured differently than depicted on FIGS. 3-12. As also shown in FIG. 10, the outer portion 24 of the second implant 6 may be longer or wider in the distal-proximal direction than the intermediate portion 22, and the intermediate portion 22 may be longer or wider along the distal-proximal direction than the inner portion 26. However, the length or width of the second implant 6 may vary and may be configured differently than depicted in FIGS. 3-12.

As shown in FIG. 9, the depth of the system 10 in the dorsal-plantar direction, as measured from the dorsal-most surface of the system 10, may vary along the system 10 and/or the first and second implants 4, 6. This depth of the first and second implants 4, 6 determines how far the first and second implants 4, 6 extend along the medial or lateral aspects of their respective bones. As shown in FIG. 9, in the first implant 4, the outer depth Z2 is greater than the inner depth Z1. In the second implant 6, the inner depth Z3 is smaller than the lateral depth Z4 (e.g., to a lesser (or greater) extent than that of the first implant 4). In some embodiments, a greater outer depth Z4 of the second implant 6 may help to decrease concentration of stress on the respectively engaged bone, such as a second metatarsal. However, it should be understood that, in other embodiments, the outer depth Z4 of the second implant 6 (as well as the outer depth Z2 of the first implant 4) may be smaller than that shown in FIG. 9.

In some embodiments, the bone engagement surface of the first and/or second implant 4, 6 may be configured to provide a close anatomical fit to the respective first and second bones 51, 52 such that the distance between the implants 4, 6 and the respective first and second bones 51, 52 in a plantar-dorsal direction is minimized. Providing a close anatomical fit between the implants 4, 6 and the respective first and second bones 51, 52 may help enhance patient comfort. A large gap or distance between the implants 4, 6 and the respective first and second bones 51, 52 in a plantar-dorsal direction may give rise to a bulky protrusion on the dorsal surface of the foot resulting in soft tissue complications. In addition, a poorly fitting first and/or second implants 4, 6 may be more easily disturbed or dislodged by external forces. In some embodiments, the configuration (e.g., radius of curvature, length, etc.) of the portions of the engagement surface of the first and/or second implants 4, 6 may be adjustable to provide a close anatomical fit to the respective first and second bones 51, 52. The engagement surface of the first and/or second implants 4, 6 may be adjusted preoperatively or intraoperatively. For example, a surgeon may bend (manually or with a tool such as a plate bender) the first and/or second implants 4, 6 to change the configuration of at least one portion of the engagement surfaces (e.g., radius of curvature, length, etc.) to custom fit the subject's respective first and second bones 51, 52. In some embodiments, the bone engaging surfaces may be manually adjusted to fit the medial-lateral contours of the respective first and second bones 51, 52 by bending the first and second implants 4, 6 in the medial or lateral direction. In some embodiments, the bone engaging surfaces may be heat-shrinkable. In yet another embodiment, the bone engaging surfaces may include multiple segments that can be removed or added to alter the configuration thereof (e.g., radius of curvature and/or arc length). In some embodiments, the configuration of the bone engaging surface may be permanent, and a surgeon may choose from a set of first and/or second implants 4, 6 with different bone engaging surfaces or portions to best suit the patient's anatomy.

As shown in FIGS. 3-8 and 10-12, the first and/or second implants 4, 6 may include at least one fixation or anchor hole 30. The at least one fixation or anchor hole 30 of the first and/or second implants 4, 6 may be configured to allow a fixation or anchor element 32 to extend therethrough and into the respective first or second bone 51, 52 to fix the first and second implants 4, 6 thereto, as shown in FIGS. 3-6. The anchoring elements may be any mechanism, such as any bone screws, screw, orthopedic screw, barbs, tine, pin, wire, nail, or any other suitable hardware, as this aspect is not limited in this regard. In addition, if the anchoring elements are screws, they may be of the locking or non-locking type, as this aspect is not limited in this regard.

As shown in FIGS. 7, 8 and 10-12, the first and/or second implants 4, 6 may include one or more anchoring hole 30. The anchoring holes 30 may be positioned anywhere along the first and/or second implants 4, 6. In some embodiments first implant 4 may include anchoring holes 30 located toward the medial side thereof, and one more anchoring hole 30 located at the dorsal side thereof. For example, in some embodiments the first implant 4 may include at least one anchoring hole 30 in the intermediate portion 12 and/or the outer portion 14. In some embodiments, the inner portion 16 may be void of an anchoring hole 30, while in other embodiments the inner portion 16 may include at least one anchoring hole 30. As shown in FIGS. 3-6, all of the anchoring holes 30 of the first implant 4 may not be utilized with an anchoring element 32. In this way, at least one of the anchoring holes 30 of the first implant 4 may be left void during use of the system 10. For example, in some embodiments, only two anchors are used to attach the first implant 4 to a bone.

Similar to the first implant 4, the second implant 6 may include at least one anchoring hole 30 located at least in the dorsal side thereof. For example, in some embodiments the second implant 6 may include at least one anchoring hole 30 in the intermediate portion 22 and/or the outer portion 24. In some embodiments, the outer portion 24 may be void of an anchoring hole 30. In some embodiments, the inner portion 26 may be void of an anchoring hole 30, while in other embodiments the inner portion 26 may include at least one anchoring hole 30. As shown in FIGS. 3-6, each of the anchoring holes 30 of the second implant 6 may not be utilized with an anchoring element 32 (i.e., left void during use of the system 10). For example, in some embodiments, only two anchors are used to attach the second implant 6 to a bone.

As shown in FIGS. 3-12, the system 10 may include a flexible cable member 40 that is coupled to, and extend between, the first and second implants 4, 6. The cable member 40 may be positioned between dorsal and plantar sides of the first and second bones 51, 52, when the first and second implants 4, 6 are coupled to the first and second bones 51, 52, respectively, as shown in FIGS. 2-6. The cable member 40 may be formed from at least one biocompatible material. The cable member 40 may be formed from one or more components. The cable member 40 may also be substantially flexible. In some embodiments, the cable member 40 may be made from a biocompatible metal (e.g., titanium), a monofilament polymer, a braided polymer, a suture or a combination thereof.

The cable member 40 may be flexible such that it allows for motion in all planes between first and second implants 4, 6. However, the cable member 40 may be stiff in tension (e.g., in a medial-lateral direction) such that it restricts any movement of the first and second implants 4, 6 apart from each other. In this way, although the flexible cable member 40 prevents movement of the first and second implants 4, 6 apart from each other, the cable member 40 may allow the angle ⊖ between the first and second implants 4, 6 (e.g., along an axial view of the first and second bones 51, 52), and thereby the first and second bones 51, 52 coupled thereto, to self-adjust (see FIG. 10). For example, when the first and second bones 51, 52 are first and second metatarsal bones, the flexible cable member 40 may prevent enlargement of the intermetatarsal angle ⊖ between the first and second metatarsal bones 51, 52, yet allow the first and second bones 51, 52 to otherwise move or angle with respect to each other. The angle ⊖ between the first and second implants 4, 6, such as the intermetatarsal angle ⊖, may be measured along the transverse plane.

In some embodiments, the length of the flexible cable member 40 extending between the first and second implants 4, 6 (e.g., in a medial-lateral direction) may be configured to move the first bone 51 towards the second bone 52, and thereby decrease an angle ⊖ formed between the first and second bones 51, 52. In this way, when the first and second bones 51, 52 are first and second metatarsal bones, the length of the flexible cable member 40 extending between the first and second implants 4, 6 may be configured to reduce the intermetatarsal angle ⊖. The length of the flexible cable member 40 extending between the first and second implants 4, 6 may be a fixed length or may be adjustable. In some embodiments, the flexible cable member 40 may be provided in fixed lengths, and/or the length thereof may be adjustable before or after the system 10 is implanted.

As shown in FIGS. 7-12, the flexible cable member 40 may be coupled to the first and second implants 4, 6 via a rigid attachment or a sliding or slidable attachment such that the respective implant 4, 6 can translate/move along a length of the cable member 40. In some embodiments, the flexible cable member 40 may be rigidly coupled to both the first and second implants 4, 6. In some other embodiments, the flexible cable member 40 may be slidably coupled to both the first and second implants 4, 6. As shown in FIGS. 7-12, in some embodiments one of the first and second implants 4, 6 may be rigidly coupled to the flexible cable member 40 and the other of the first and second implants 4, 6 may be slidably coupled to the flexible cable member 40. For example, in the embodiment shown in FIGS. 7-12 the flexible cable member 40 is rigidly coupled to the first implant 4 and slidably coupled to the second implant 6.

The flexible cable member 40 may be rigidly coupled to the at least one of the first and second implants 4, 6 in any manner or by any mechanism. For example, as shown in FIGS. 7-12 the system 10 may include at least one fitting 42 that is configured to couple to the flexible cable member 40 and one of the first and second implants 4, 6. The fitting 42 may be configured to rigidly couple or affix to an end portion or an intermediate portion of the flexible cable member 40. The fitting 42 may extend through a portion of one of the first and second implants 4, 6 and rigidly couple or affix thereto. For example, as shown in FIGS. 6-12, the at least one fitting 42 may include a shaft portion with an aperture extending therein or therethrough configured to accept the flexible cable member 40 therein. The shaft portion of the fitting 42 may be crimped or compressed onto the flexible cable member 40 positioned therein to rigidly couple the cable member 40 and the fitting 42. The at least one fitting 42 may be rigidly coupled to the first and second implants 4, 6, such as to the inner portions 16, 26 thereof, via any mechanism or configuration. For example, the at least one fitting 42 may extend through an aperture in a portion of the first or second implants 4, 6, and may be rigidly coupled within the aperture via any means or mechanism. For example, in some embodiments the fitting 42 may be welded to the aperture (i.e., to the portion of the first or second implants 4, 6 proximate to the aperture). In some embodiments, as shown in FIGS. 7-12, the at least one fitting 42 may (or may not) include a rim portion that defines a larger cross-section than the shaft portion and the smallest portion of the aperture. The rim portion of the fitting 42 may thereby prevent the fitting 42 from passing through the aperture of the first and second implants 4, 6. In one embodiment, the rim portion (and/or the shaft portion) may be welded to the aperture (i.e., to the portion of the first or second implants 4, 6 proximate to the aperture). The aperture of the first or second implant 4, 6 may be straight (e.g., cylindrical) or stepped.

As yet another example (not shown), the fitting 42 may be spherical or rounded and may be positioned within a recess or groove formed into the engagement surface of the first or second implant 4, 6. The groove may cooperate with an aperture that allows the flexible cable member 40 to extend therein from the exterior side or surface of the first or second implant 4, 6. The flexible cable member 40 may be crimped or otherwise rigidly coupled to the spherical or rounded fitting 42, and the fitting 42 may be able to freely rotate and pivot within the recess in the first or second implant 4, 6. In this way, the flexible cable member 40 and the fitting 42 are able to both rotate within the recess during relative movement between the first and second implants 4, 6, which may reduce bending forces on the flexible cable member 40. However, the rigid connections between the flexible cable member 40 and one of the first and second implants 4, 6 disclosed herein are only exemplary, and any other arrangement or configuration that effectively rigidly couples the flexible cable member 40 and the one of the first and second implants 4, 6 (such that the respective first or second implant 4, 6 is unable to slide along the cable member 40), may be utilized.

As discussed above, at least one of the first and second implants 4, 6 may be slidably coupled to the flexible cable member 40 such that it can translate along the cable member 40, yet is prevented from translating away from the other of the first and second implants 4, 6 (and thereby the first and second bones 51, 52 coupled thereto) to prevent the intermetatarsal angle ⊖ from enlarging. Such a sliding connection between the flexible cable member 40 and the first and/or second implants 4, 6 may be accomplished by any mechanism or means.

In some embodiments, the flexible cable member 40 may form at least one loop (a continuous loop) that passes through the first and/or second implants 4, 6 at least once, as shown in FIGS. 7-12. For example, two portions of the looped flexible cable member 40 may pass through corresponding apertures of the first and/or second implants 4, 6. In this way, the first and/or second implant 4, 6 may be slidably coupled to the looped flexible cable member 40 such that the cable member 40 prevents the implants 4, 6 from moving away from each other. However, as the looped flexible cable member 40 is able to feed through the at least one aperture, the respective first and/or second implant 4, 6 may be able to slide along the cable member 40. In this way, system 10 may allow the angle Θ between the first and second implants 4, 6 (and thereby the intermetatarsal angle Θ between the first and second metatarsal bones 51, 52 coupled, respectively, therewith) to self-adjust to match a patient's anatomy.

Figure 7:
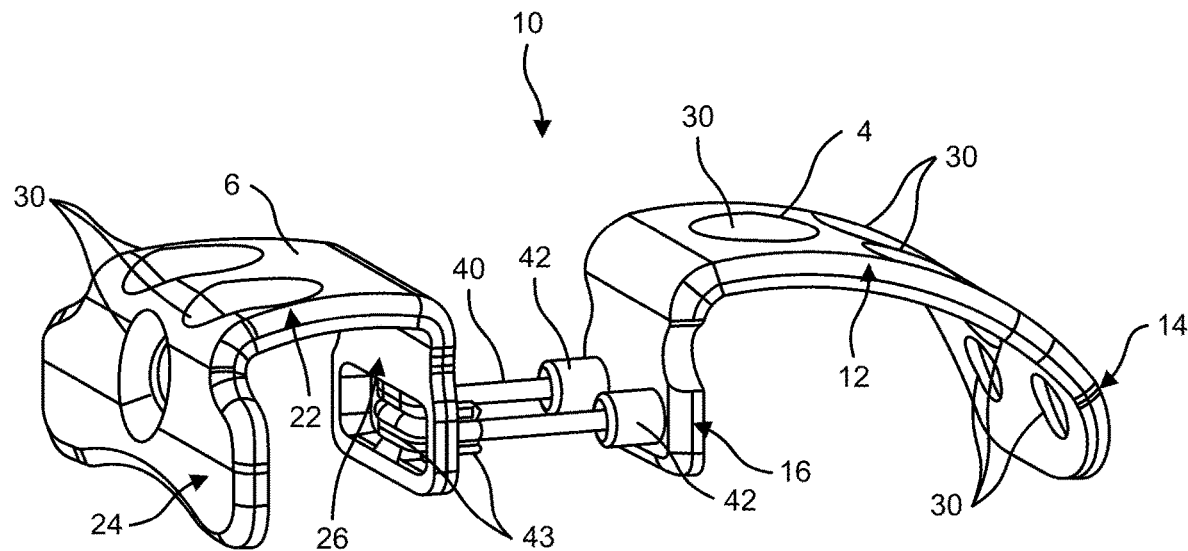
FIG. 7 illustrates a perspective view of the implant system of FIG. 1.
Figure 8:
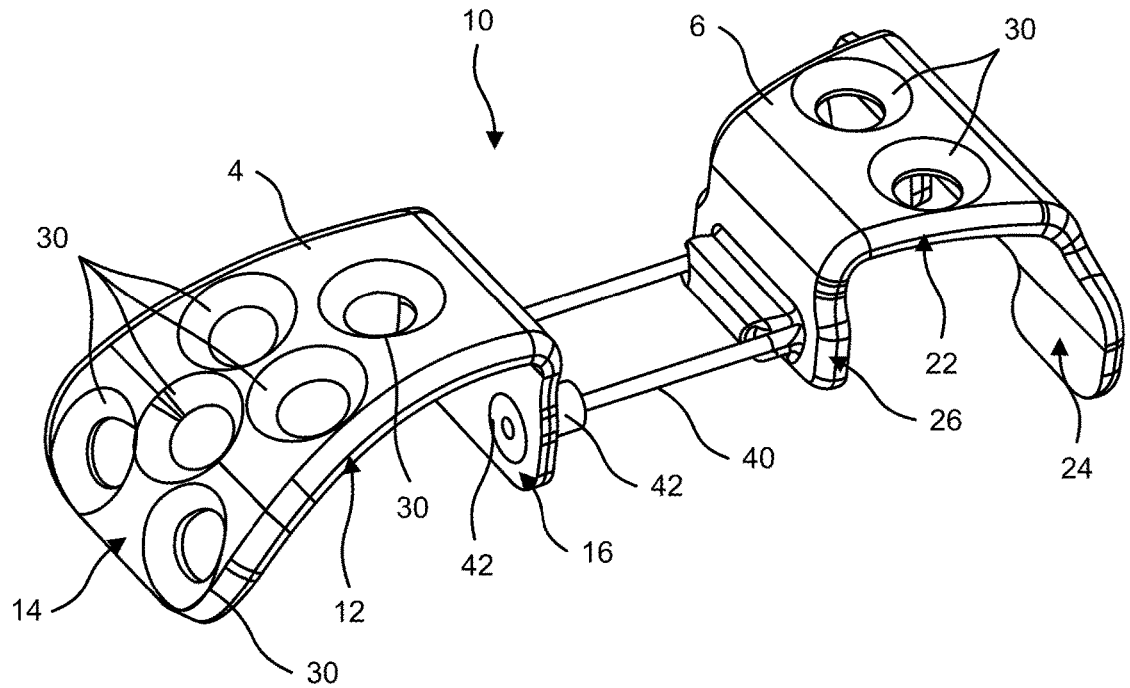
FIG. 8 illustrates an elevational perspective view of the implant system of FIG. 7.
Figure 11:
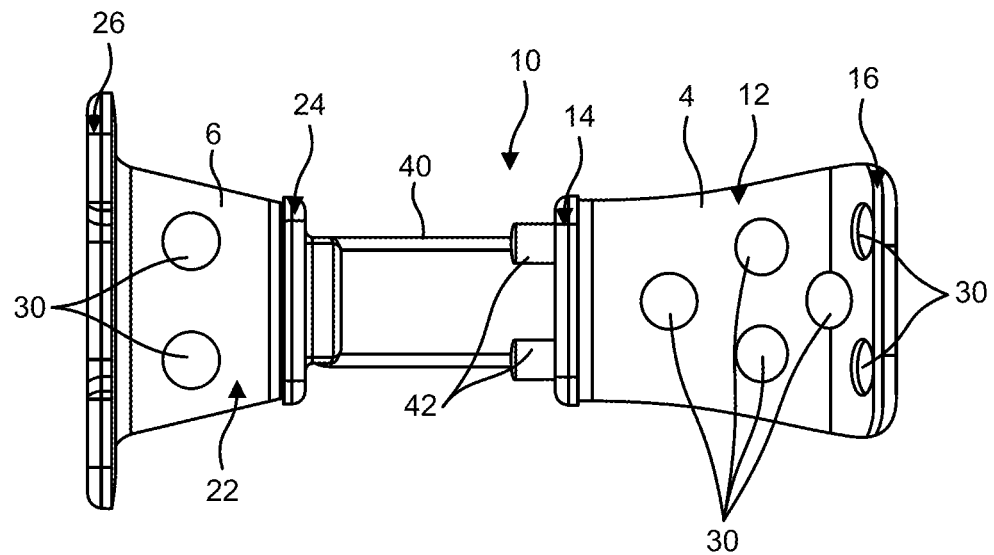
FIG. 11 illustrates a bottom view of the implant system of FIG. 7.
Figure 12:
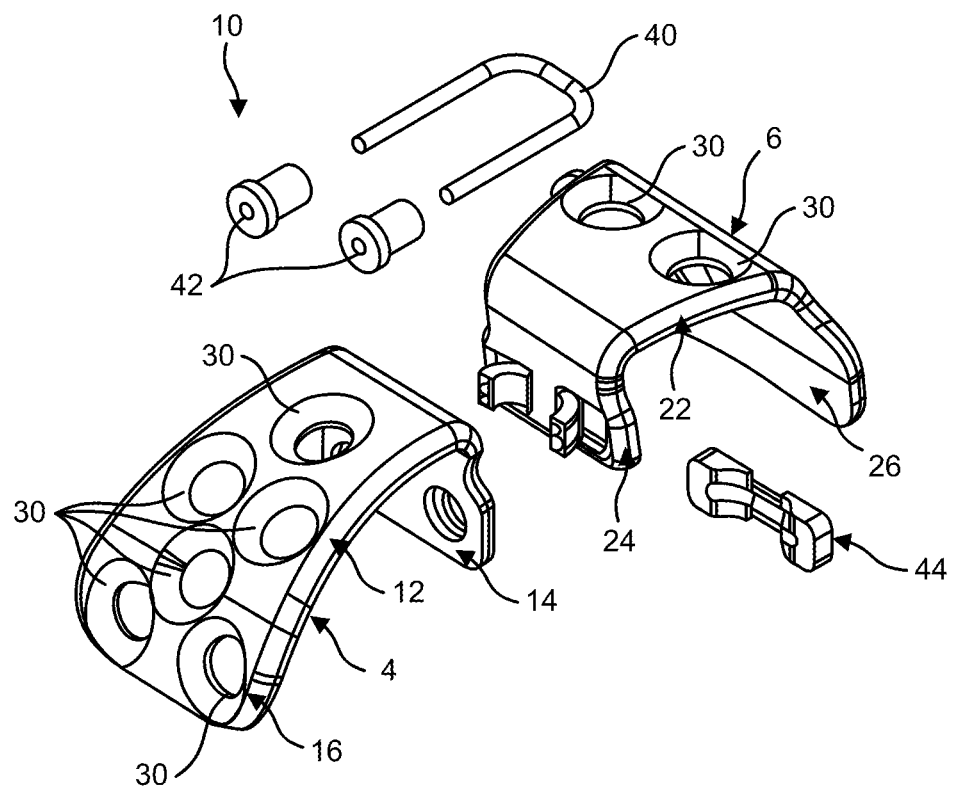
FIG. 12 illustrates an elevational perspective exploded view of the implant system of FIG. 7.

In some embodiments, the first and/or second implant 4, 6 may be slidably attached to the cable member 40 via at least one aperture of the first and/or second implant 4, 6 that is configured to accept the cable member 40 therethrough. For example, as shown in FIGS. 3-12 the inner portion 16, 24 of the first or second implant 4, 6 may include at least one aperture, such as a pair of apertures, to allow the cable member 40 to extend therethrough and between the first and second implants 4, 6. In some such embodiments, the first and/or second implant 4, 6 may include at least one guide portion and/or arm 43 that provides a smooth guide surface (e.g., groove) for the cable member 40 to translate along as the respective implant 4, 6 slides along the length of the cable member 40, as shown in FIGS. 7, 10 and 12. In some embodiments, the system 10 may further include at least one cap member 44 configured to couple to the first and/or second implant 4, 6 and cooperate with the least one guide portion and/or arm 43 to form a channel therebetween to further guide the cable member 40 through the respective implant 4, 6 as it slides along the length of the cable member 40, as shown in FIGS. 11 and 12. The at least one cap may also substantially close or seal off the at least one aperture in the first and/or second implant 4, 6 through which the cable member 40 passes.

Figure 13:
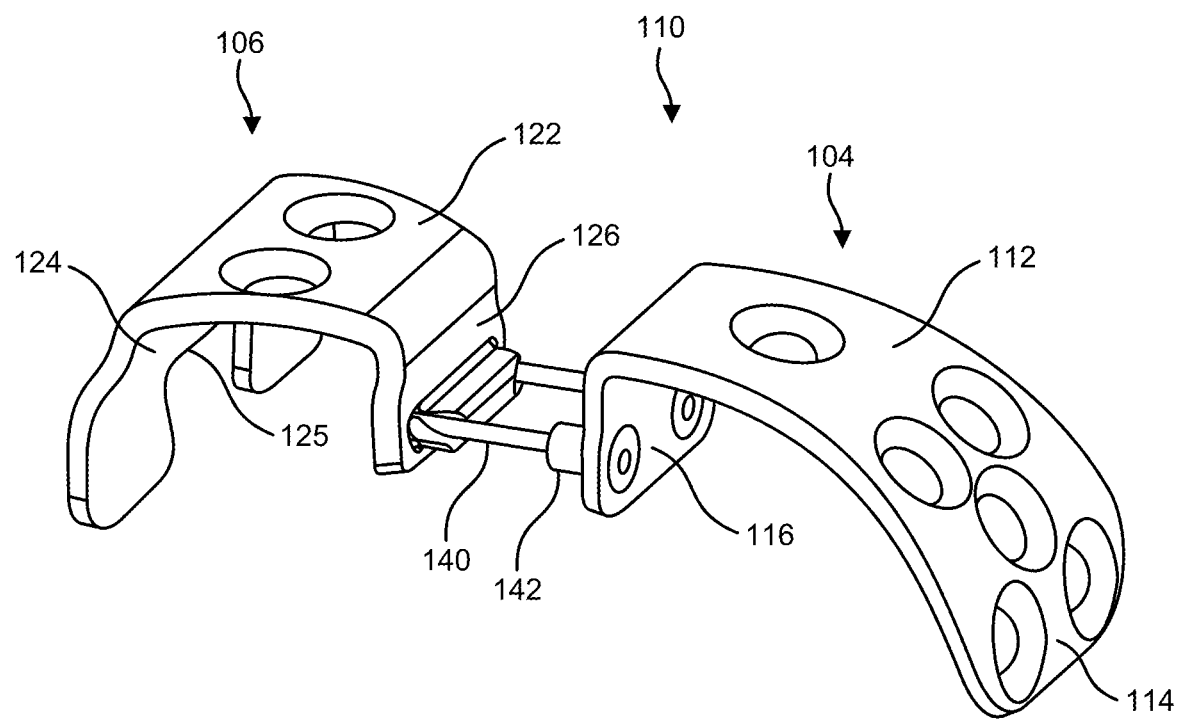
FIG. 13 illustrates an elevational perspective view of another exemplary implant system for correcting a bunion.
Figure 14:
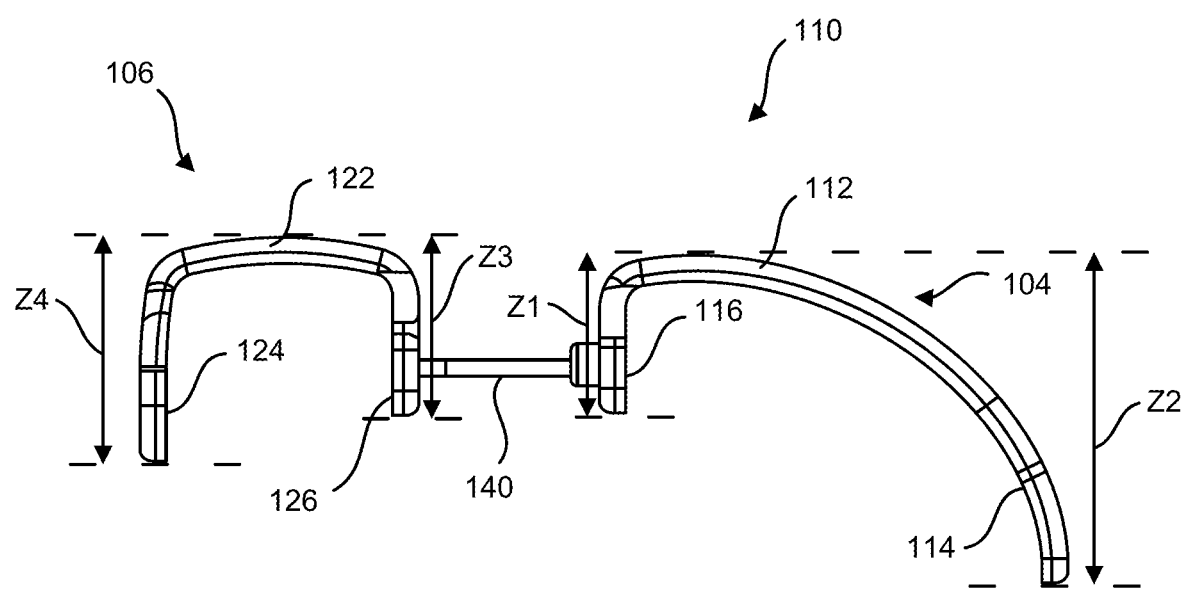
FIG. 14 illustrates a side view of the implant system of FIG. 13.

FIGS. 13 and 14 illustrate another exemplary bunion correction system generally indicated by the reference numeral 110. Exemplary bunion correction system 110 is substantially similar to exemplary bunion correction system 10 described above in connection with FIGS. 1-12, and therefore like reference numerals preceded by the number "1" are used to indicate like elements or features. The description above with reference to exemplary bunion correction system 10 may therefore equally apply to the particular components, systems, features or the like of exemplary bunion correction system 110 and is not repeated hereinafter for brevity sake.

As shown in FIG. 14, system 110 differs from system 10 (see FIG. 8) in the relative dorsal-plantar depths of the portions of the first and second implants 104, 106. As shown in FIG. 14, in the first implant 104, the outer depth Z2 is still greater than the inner depth Z1, but to a much greater extent. As also shown in FIG. 14, in the second implant 106, the outer depth Z4 is still greater than the inner depth Z3, but also to a much greater extent. The system 110 of FIGS. 13 and 14 is thereby larger that the system 10 of FIGS. 1-12 and thus may be suitable for a larger patient and/or may wrap further around respective bones.

As shown in FIG. 13, the plantar portion of the outer portion 124 of the second implant 106 includes a space or indentation 125. The presence of the space or indentation 125 creates a pair of tab portions that are spaced from one another in the proximal-distal direction, as shown in FIG. 13.

Figure 15:
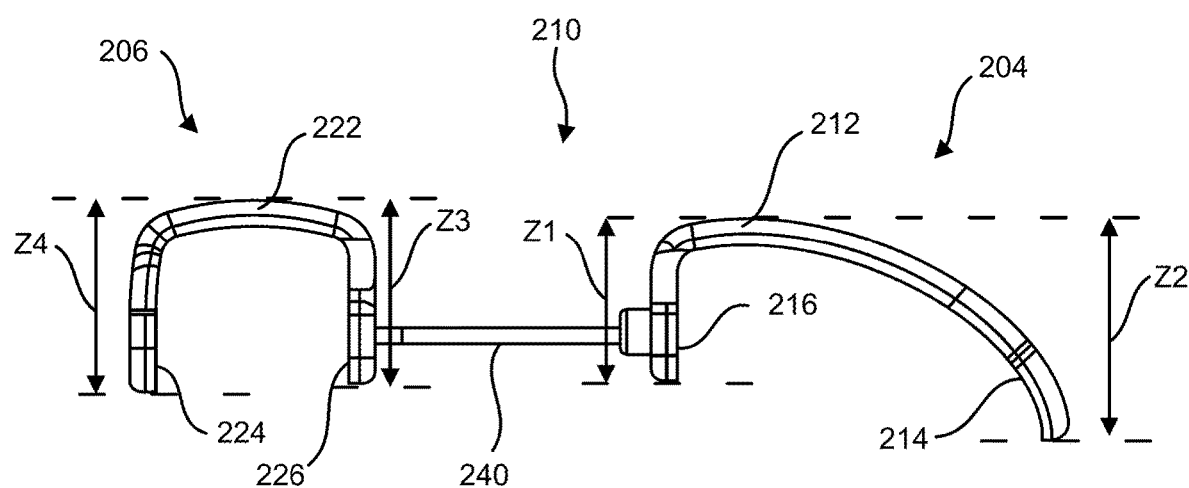
FIG. 15 illustrates a side view of another exemplary implant system for correcting a bunion.

FIG. 15 illustrates another exemplary bunion correction system generally indicated by the reference numeral 210. Exemplary bunion correction system 210 is substantially similar to exemplary bunion correction system 10 described above in connection with FIGS. 1-12 and exemplary bunion correction system 110 described above in connection with FIGS. 13 and 14, and therefore like reference numerals preceded by the number "2" are used to indicate like elements or features. The description above with reference to exemplary bunion correction systems 10 and 110 may therefore equally apply to the particular components, systems, features or the like of exemplary bunion correction system 210 and is not repeated hereinafter for brevity sake.

As shown in FIG. 15, system 210 differs from system 10 (see FIG. 8) and system 110 (see FIG. 14) in the relative dorsal-plantar depths of the portions of the first implant 204. As shown in FIG. 15, in the first implant 204, the outer depth Z2 is greater than the inner depth Z1, but to a greater extent than in the first implant 4 and to a lesser extent than in the first implant 104. The system 210 of FIG. 15 is thereby larger that the system 10 of FIGS. 1-12 but smaller that the system 110 of FIGS. 13 and 14, and thus may be suitable for an intermediately sized patient. Further, as shown in FIG. 15 the depth of the outer portion 224 is only slight greater than the depth of the inner portion 226 of the second implant 206. In some embodiments, the depths of the outer and inner portions 224, 226 of the second implant 206 are substantially the same.

Figure 16:
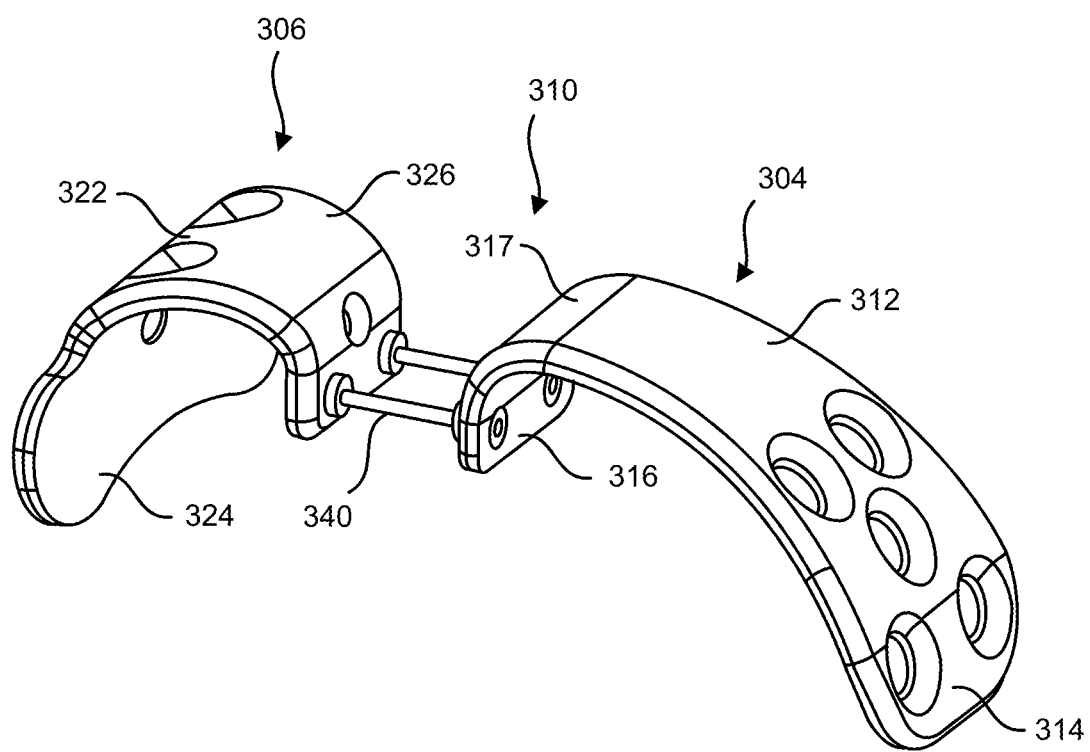
FIG. 16 illustrates an elevational perspective view of another exemplary implant system for correcting a bunion.
Figure 17:
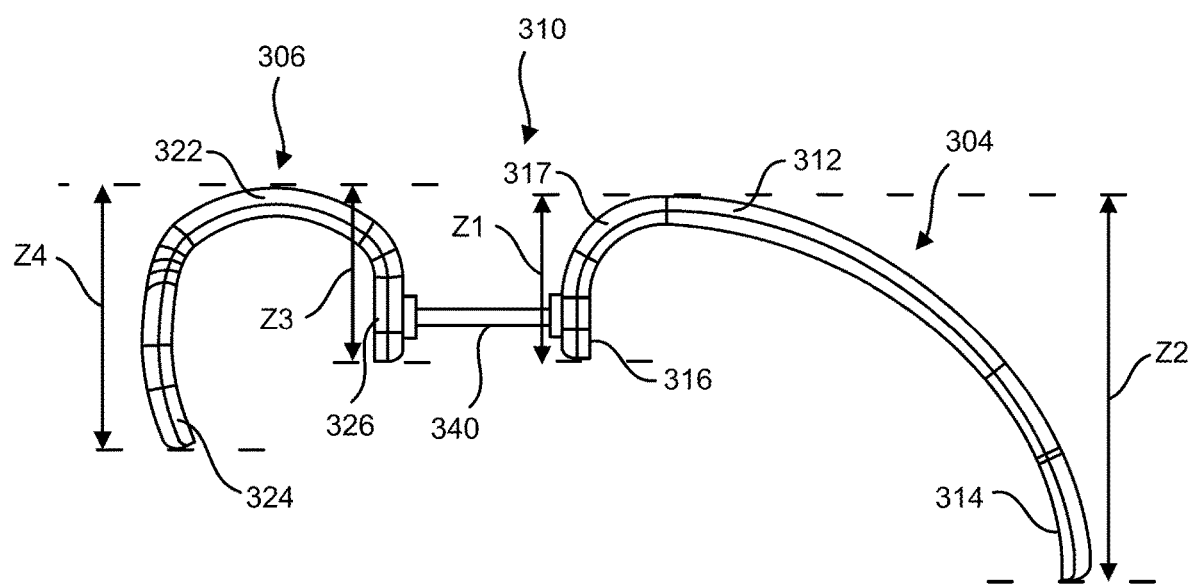
FIG. 17 illustrates a side view of the implant system of FIG. 16.

FIGS. 16 and 17, illustrates another exemplary bunion correction system generally indicated by the reference numeral 310. Exemplary bunion correction system 310 is substantially similar to exemplary bunion correction system 10 described above in connection with FIGS. 1-12, exemplary bunion correction system 110 described above in connection with FIGS. 13 and 14, and exemplary bunion correction system 210 described above in connection with FIG. 15, and therefore like reference numerals preceded by the number "3" are used to indicate like elements or features. The description above with reference to exemplary bunion correction systems 10, 110 and 210 may therefore equally apply to the particular components, systems, features or the like of exemplary bunion correction system 310 and is not repeated hereinafter for brevity sake.

As shown in FIG. 17, system 310 differs from system 10 (see FIG. 8), system 110 (see FIG. 14) and system 210 (see FIG. 15) in the curvature or shape of the first and second implants 304, 306. As shown in FIG. 17, the first implant 304 includes a second inner portion 317 that extends between the planar inner portion 316 and the intermediate portion 312. The second inner portion 317 is curved to a greater extent (i.e., define by at least one smaller radius) than the intermediate portion 312. The second inner portion 317 may provide a smoother or more gentle transition between the planar inner portion 316 and the intermediate portion 312 as opposed to a relatively sharp 90-degree transition or bend therebetween. The second inner portion 317 may act to increase the medial-lateral width of the first implant 304.

As also shown in FIG. 17, both the outer portion 324 and the intermediate portion 322 of the second implant 306 may be radiused or curved, and may be defined by relatively smaller radii. As such, the outer portion 324 and the intermediate portion 322 may be significantly curved. As also shown in FIG. 17, the inner portion 326 of the second implant 306 maybe shortened in the dorsal-plantar direction, which may account for the added height of the intermediate portion 322 due to its curvature.

Figure 18:
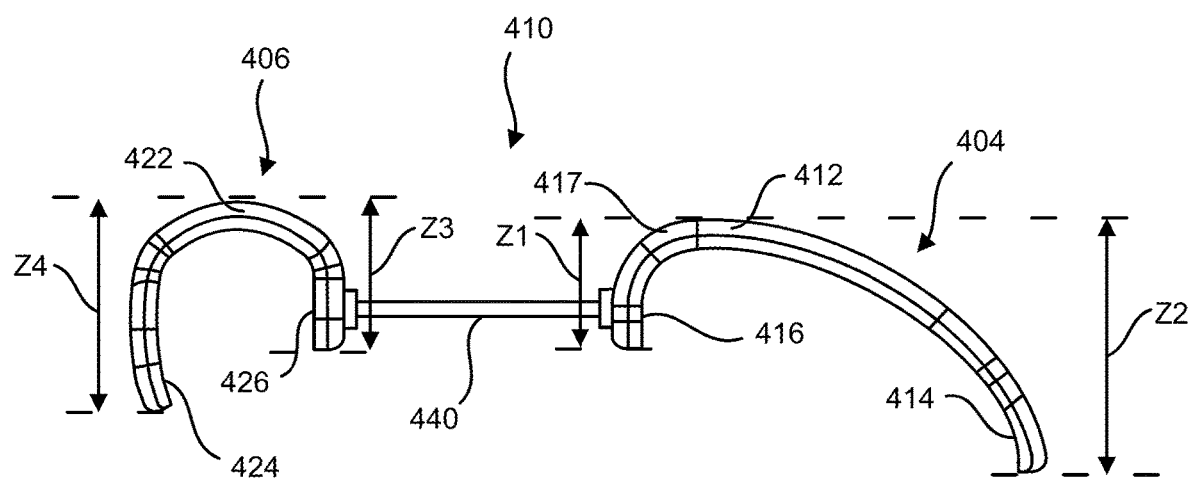
FIG. 18 illustrates a side view of another exemplary implant system for correcting a bunion.

FIG. 18, illustrates another exemplary bunion correction system generally indicated by the reference numeral 410. Exemplary bunion correction system 410 is substantially similar to exemplary bunion correction system 310 described above in connection with FIGS. 16 and 17, and therefore like reference numerals preceded by the number "4" are used to indicate like elements or features. The description above with reference to exemplary bunion correction system 310 may therefore equally apply to the particular components, systems, features or the like of exemplary bunion correction system 410 and is not repeated hereinafter for brevity sake.

As shown in FIG. 18, system 410 differs from system 310 (see FIG. 7) in the relative dorsal-plantar depth of the portions of the first implant 404. As shown in FIG. 18, in the first implant 404, the outer depth Z2 is still greater than the inner depth Z1, but to a lesser extent. The system 410 of FIG. 18 is thereby smaller that the system 310 of FIGS. 16 and 17, and thus may be suitable for a smaller patient and/or may wrap less around a respective bone.

The systems 10, 110, 210, 310 and 410 disclosed herein (e.g., the first and second implants and a flexible cable member thereof) may be utilized to reposition a first bone (e.g., a first or fifth metatarsal bone) toward an adjacent second bone (e.g., a second or further metatarsal bone, respectively) to a more anatomically correct position to treat a bunion formed by the first bone. Initially, the system 10, 110, 210, 310 and 410 may be introduced into a patient via at least one incision that is proximate to the first and second bones. For example, a first dorsal incision may be formed between the first and second bones and a second dorsal incision may be formed on an opposing side of the first bone. A tissue tunnel may also be formed across and/or between the first and second dorsal incisions over the first and second bones to accommodate placement of the system 10, 110, 210, 310 and 410. As another example, a dorsal incision may be formed that bisects the width of the first bone.

After the at least one incision is formed proximate to the first and second bones (e.g., at least one dorsal incision), soft tissue may be released from at least one of the first and second bones. Further, the intermetatarsal angle $\ominus$ between the first and second bones may be reduced. For example, the metatarsal angle $\ominus$ between the first and second bones may be reduced manually or via surgical instrument (e.g., a bone clamp or another instrument). Once the metatarsal angle $\ominus$ between the first and second bones is reduced and maintained, the space or gap between the first and second bones may be gauged. The space or gap between the reduced first and second bones may also be intraoperatively imaged to confirm correct gap size.

With the metatarsal angle $\ominus$ reduced and the gap size corrected, the system 10, 110, 210, 310 and 410 may be placed/fit onto the first and second bones to evaluate the fit. For example, the engagement surface of the first implant thereof may be positioned over and on the dorsal side of the first bone, and the engagement surface of the second implant thereof may be positioned over and on the dorsal side of the second bone. The flexible cable member may or may not be coupled to the first and second implants during such trial fitting. If the first and/or second implants do not fully fit/comply with or mirror the first and second bones, respectively, the first and/or second implants may be bend or otherwise deformed to more closely match the profile of the first and second bones.

Figure 19:
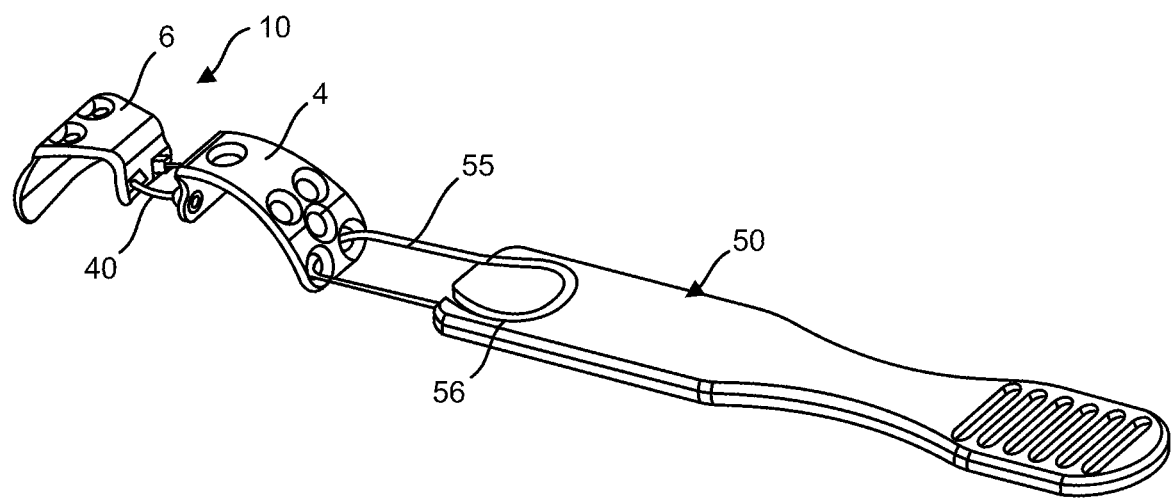
FIG. 19 illustrates an elevational perspective view of a first exemplary inserter for implanting a bunion correction implant system.
Figure 20:
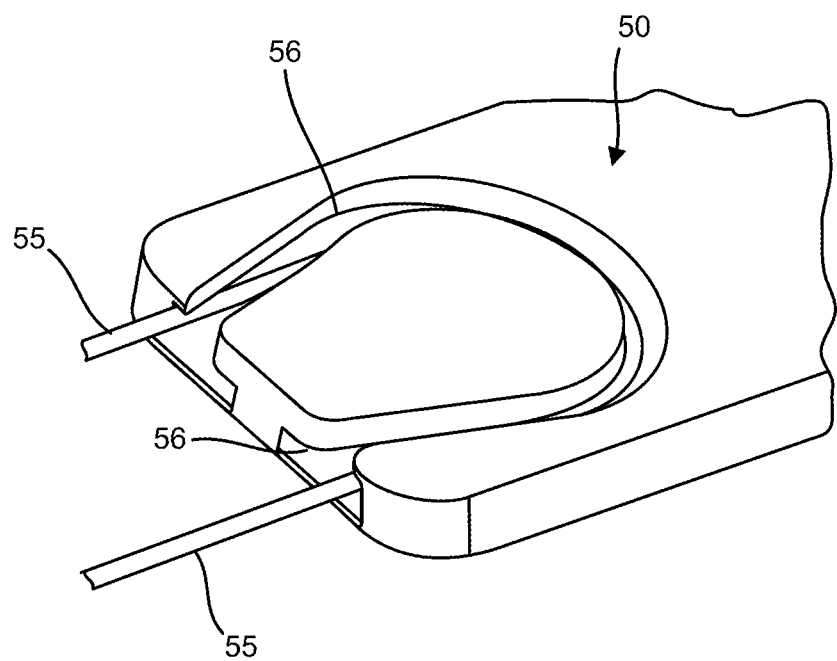
FIG. 20 illustrates an enlarged elevational perspective view of a portion of the exemplary inserter of FIG. 19.

Once the system 10, 110, 210, 310 and 410 has been gauged and adjusted, if needed, the system 10 may be implanted. FIGS. 19 and 20 illustrate an exemplary inserter 50 and a closed cable loop 55 that may be utilized to insert the system 10 into the at least one incision and engage the first and second implants 4, 6, with the first and second bones 51, 52, respectively. While the system 10 is utilized in the figures as the exemplary bunion correction system being implanted, systems 110, 210, 310 and 410 or any other bunion correction system may equally be utilized by inserter 50.

As shown in FIGS. 19 and 20, the inserter 50 may be substantially flat and elongate and include a groove or slot 56 at one end. The groove 56 may be arcuate shaped such that an end portion of the cable loop 55 may be positioned within and extend through the groove 56. In this way, the inserter 50 may hook or attach to the cable loop 55 for pulling the system 10 through the incision, as described further below. The groove 56 may include an undercut that further aids in retaining the cable loop 55 within the groove 56.

The closed cable loop 55 may be coupled to the system 10, such as to the first and/or second implants 4, 6. In the exemplary embodiments, the closed cable loop 55 is coupled to the first implants 4, as shown in FIG. 19. The cable loop 55 may couple to the system 10 via any mechanism or configuration. For example, the cable loop 55 may be coupled to the system 10 by extending through an aperture of the system 10, such as through at least one of the anchoring holes 30 of the first and/or second implants 4, 6. In such an embodiment, after an end of the cable loop 55 is passed through the at least one aperture of the first and/or second implants 4, 6, the end may be joined with the other end of the cable 55 to form a closed loop. For example, the ends of the cable loop 55 may be joined via a crimped fitting or sleeve or by any mechanism or configuration to form a closed loop.

With the inserter 50 coupled to the system 10 via the closed loop 55, an end of the inserter 50 void of the closed loop 55 may be inserted and/or translated through the at least one incision. The inserter 50 may be pulled or otherwise moved through the incision, such as along a lateral to medial direction, until the first and second implants 4, 6 are substantially positioned on the first and second bones 51, 52, respectively. The inserter 50 may be translated through the incision such that the first and second implants 4, 6 are positioned distally on the first and second bones 51, 52, respectively, with the system 10 positioned just proximal to the head of the first bone 51, such as at the metaphyseal/diaphyseal junction if the first bone 51 is a first metatarsal bone. The second implant 6 may then be manually placed on the second bone 52 such that the engagement surface thereof engages the corresponding outer surface of the second bone 52.

Once the second implant 6 is engaged with the second bone 52, the first bone 51 may be translated toward the second bone 52 to reduce the metatarsal angle $\ominus$ manually or with an instrument/tool. With the angle between the first and second bones 51, 52 reduced, the first implant 4 may be manually placed on the first bone 51 such that the engagement surface thereof engages the corresponding outer surface of the first bone 51. In some embodiments, the inserter 50 and/or another instrument/tool may be utilized to engage the first implant 4 with the first bone 51. Once the first implant 4 is engaged with the first bone 51, the cable loop 55 may be cut or otherwise opened, and then pulled out from the system 10.

Figure 21:
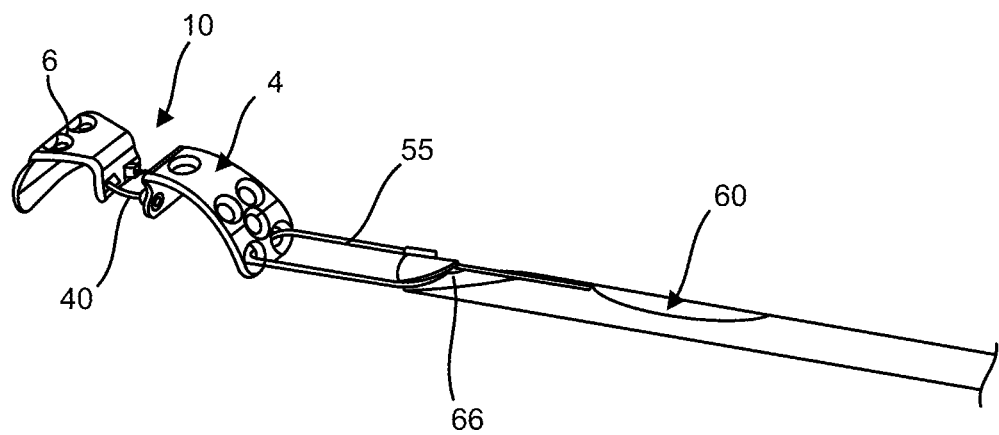
FIG. 21 illustrates an elevational perspective view of a second exemplary inserter for implanting a bunion correction implant system.
Figure 22:
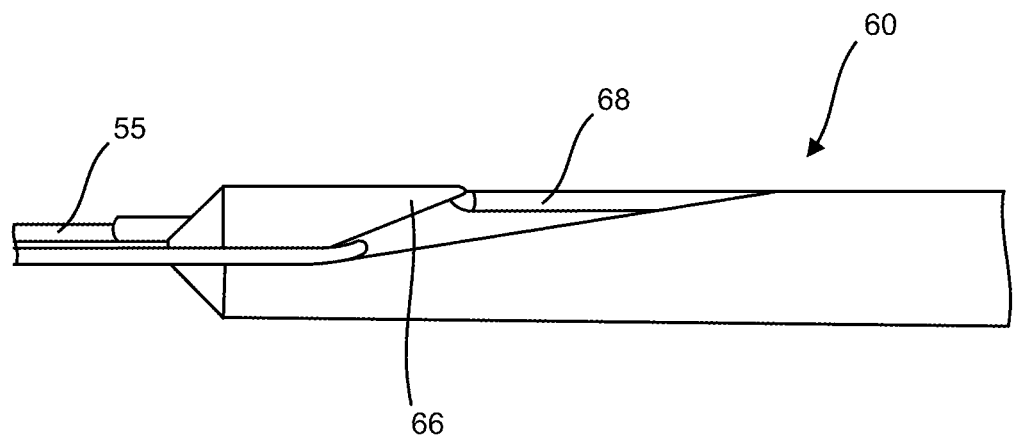
FIG. 22 illustrates an enlarged elevational perspective view of a portion of the exemplary inserter of FIG. 21.

FIGS. 21 and 22 illustrate another inserter 60 that may be utilized with the closed cable loop 55 to insert the system 10 into the at least one incision and the engage the first and second implants 4, 6, with the first and second bones 51, 52, respectively. As shown in FIGS. 21 and 22, the inserter 60 may be substantially elongate and/or cylindrical. One end of the inserter 60 may include a hook portion 66 formed by an angled undercut at one end of the inserter 60. The cable loop 55 may extend around the hook portion 66 and be positioned within the undercut to couple the cable loop 55 and the inserter 60 so that the inserter 60 can pull the system 10 coupled to the cable loop 55 through the at least one incision, as shown in FIG. 22. As also shown in FIG. 22, the inserter 60 may include a flexible pin, tab or member 68 that extends at least partially across the undercut, and potentially to the hook portion 66, to allow the cable loop 55 to be positioned within the undercut and around the hook portion 66 and prevent or inhibit the cable loop 55 from disengaging from the hook portion 66. Further, the flexible pin, tab or member 68 may protect the patient from the hook portion 66 as the inserter is pulled through the incision. Once the cable loop 55 is engaged with the inserter 60 and the system 10, the inserter 60 may be utilized to implant the system 10 in the same manner as discussed above with respect to inserter 50, for example.

Figure 23:
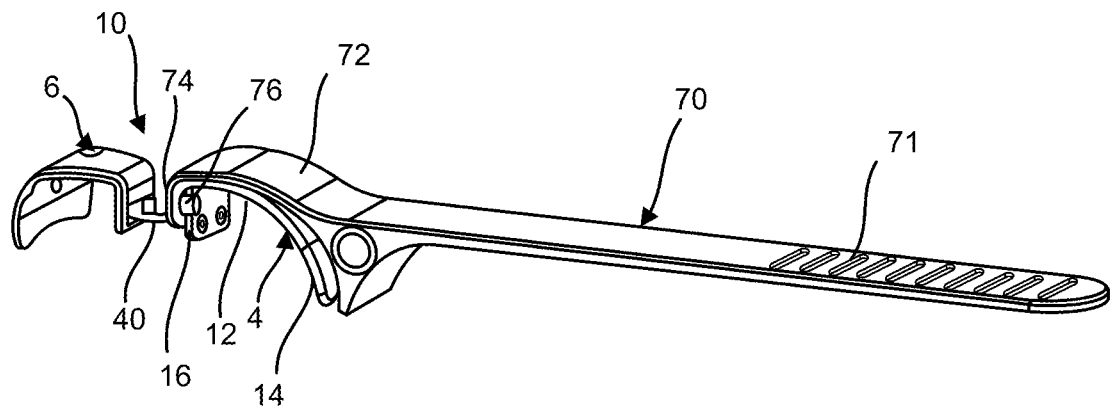
FIG. 23 illustrates an elevational perspective view of a third exemplary inserter for implanting a bunion correction implant system.
Figure 24:
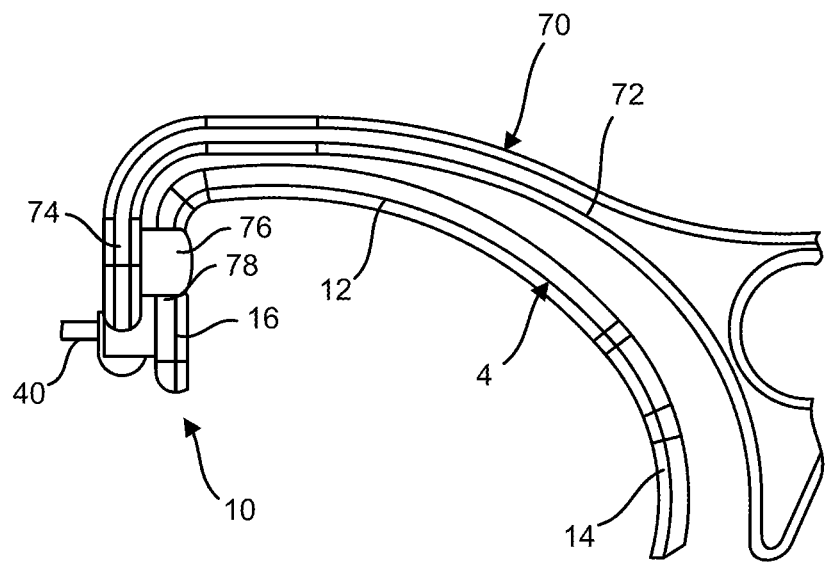
FIG. 24 illustrates an enlarged elevational perspective view of a portion of the exemplary inserter of FIG. 23.

FIGS. 23 and 24 illustrate another inserter 70 that may be utilized to insert the system 10 into the at least one incision and engage the first and second implants 4, 6, with the first and second bones 51, 52, respectively. The inserter 70 may not be utilized with the cable loop 55. The inserter 70 may include an elongate handle portion 71 and a head portion 72, as shown in FIGS. 23 and 24. The head portion 72 of the inserter 70 may include a contoured inner surface that substantially mirrors the shape of the first implant 4. The head portion 72 also includes a portion 74 that extend along the exterior of the inner portion 16 of the first implant 4, as shown in FIG. 24. The portion 74 of the head portion 72 may include at least one tapered pin or other projection 78 that is configured to extend into at least one aperture or groove 78 of the inner portion 16 of the first implant 4, as shown in FIG. 24. In some embodiments, the at least one aperture 78 in the inner portion 16 of the first implant 4 that engages with the at least one pin 78 may be an anchoring hole. The head portion 72 of the inserter 70 may also extend over the intermediate portion 12 and/or outer portion 14 of the first implant 4. The head portion 72 of the inserter 70 may thereby capture the first implant 4 within the contoured inner surface via the contoured inner surface itself and the at least one pin 78 extending within the at least one aperture 78 in the inner portion 16 of the first implant 4. The inserter 70 may thereby be utilized to implant the system 10 in a similar manner as discussed above with respect to inserter 50, for example. During insertion, the head portion 72 of the inserter 70 may act to shield the system 10 and the first implant 4 from the incision site to prevent the system 10 and the first implant 4 from disengaging from the inserter 70.

Figure 25:
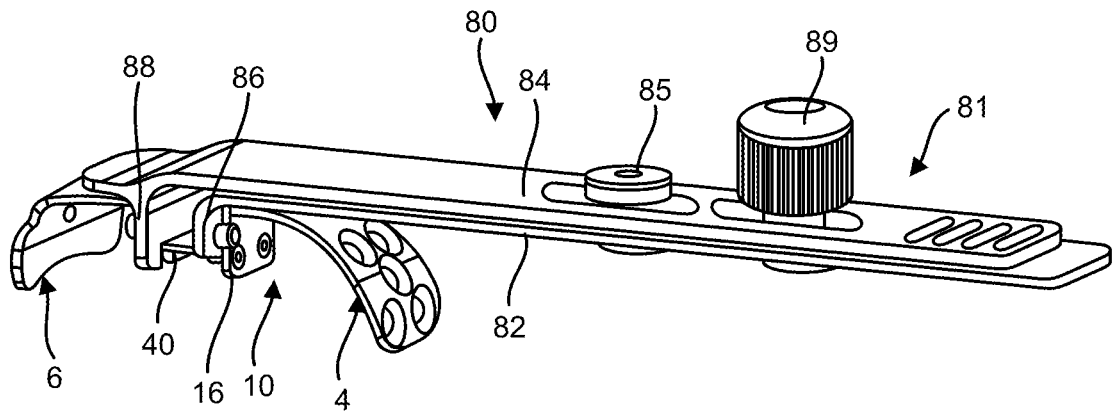
FIG. 25 illustrates an elevational perspective view of a fourth exemplary inserter for implanting a bunion correction implant system.
Figure 26:
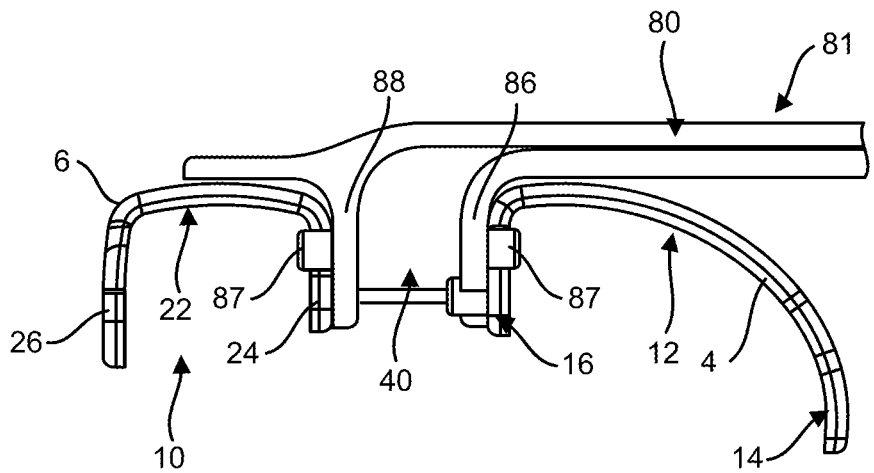
FIG. 26 illustrates an enlarged side view of a portion of the exemplary inserter of FIG. 25.
Figure 27:
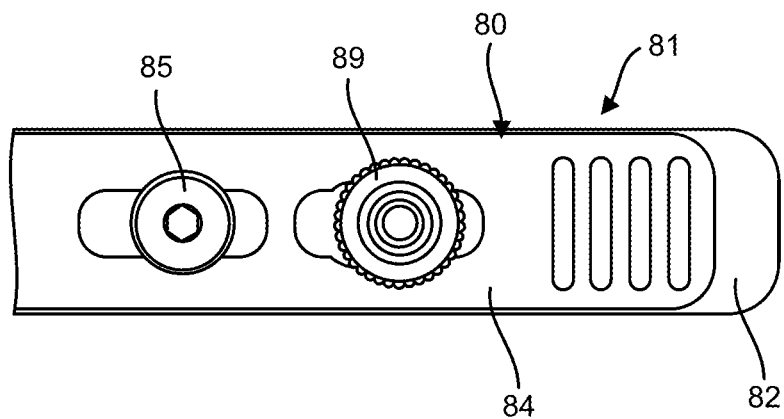
FIG. 27 illustrates an enlarged top view of a portion of the exemplary inserter of FIG. 25.

FIGS. 25-27 illustrate yet another inserter 80 that may be utilized to insert the system 10 into the at least one incision and engage the first and second implants 4, 6, with the first and second bones 51, 52, respectively. The inserter 80 may not be utilized with the cable loop 55. The inserter 80 may include first and second elongate substantially flat members 82, 84 overlying each other, as shown in FIGS. 25-27. The inserter 80 may include an elongate handle portion 81 formed by the first and second members 82, 84, as shown in FIGS. 25-27. The first and second members 82, 84 may include a first and second head portion 86, 88, respectively. The first head portion 86 of the first member 82 may extend along the exterior of the inner portion 16 of the first implant 4, as shown in FIGS. 25 and 26. The first head portion 86 of the first member 82 may include at least one tapered pin or other projection 87 that is configured to extend into at least one aperture, groove or recess of the inner portion 16 of the first implant 4, as shown in FIG. 25. As shown in FIGS. 25 and 26, the second head portion 88 of the second member 84 may extend along the exterior of the inner portion 26 of the second implant 6. The second head portion 86 of the second member 84 may also include at least one tapered pin or other projection 87 that is configured to extend into at least one aperture, groove or recess of the inner portion 26 of the second implant 6, as shown in FIGS. 25 and 26.

The first and second members 82, 84 may be slidably coupled to each other such that the first and second head portions 86, 88 can be manually translated away from each other to apply pressure between the inner portion 16 of the first implant 4 and the inner portion 26 of the second implant 6, as shown in FIG. 26. The first and second members 82, 84 may be slidably coupled via at least two pins or screws 85, 89 and corresponding slots, as shown in FIGS. 25 and 27. One of the screw 89 may be positioned within a scalloped slot to control relative spacing or positioning of the first and second members 82, 84. However, any other arrangement or configuration may be utilized to allow and/or control a sliding connection between the first and second members 82, 84.

In use, first and second members 82, 84 may be manually translated with respect to each other such that the first head portion 86 and the at least one projection 87 of the first member 82 engages the inner portion 16 of the first implant 4, and the second head portion 86 and the at least one projection 87 of the second member 84 engages the inner portion 26 of the second implant 6. In this way, the inserter 80 may be coupled between the first and second implants 4, 6 of the system 10. As least one screw or other mechanism 89 may be utilized to lock the first and second members 82, 84 in such a position to prevent the inserter 80 from disengaging from the system 10. The inserter 80 may thereby be utilized to implant the system 10 in the same manner as discussed above with respect to inserter 50, for example.

Once the system 10 is translated through the at least incision and the first implant 4 is engaged with the first bone 51 (such as via at least one of the inserters 50, 60, 70, 80, or any other inserter) and the utilized inserter 50, 60, 70, 80 is removed from the incision site, the first and/or second implants 4, 6 may be affixed to the first and second bones 51, 52, respectively via at least one temporary fixation mechanism. For example, with the first and second implants 4, 6 engaging the first and second bones 51, 52, respectively, at least one olive k-wire or other temporary fixation mechanism may be inserted through at least one aperture of the first and second implants 4, 6 (e.g., at least one anchoring hole 30) and into the first and second bones 51, 52, respectively.

With the first and second implants 4, 6 engaging and affixed to the first and second bones 51, 52, at least one bone screw or other bone fixation member 32 may be inserted through at least one of the anchoring apertures 30 of the first and second implants 4, 6 and into the first and second bones 51, 52 to rigidly couple the first implant 4 to the first bone 51 and the second implant 6 to the second bone 52. In some embodiments, each of the first and second implants 4, 6 may include at least two fixation members 32 extending through the anchoring holes 30 and into the first and second bones 51, 52, respectively. In some embodiments, the first and second bones 51, 52 may be pre-drilled to receive the at least one bone screw or other bone fixation member 32 via a drill and, potentially, a drill guide. After the at least one bone fixation member 32 rigidly couples the first and second implants 4, 6 to the first and second bones 51, 52, respectively, any temporary fixation mechanisms may be removed from the first and second implants 4, 6 and the first and second bones 51, 52.

Figure 28:
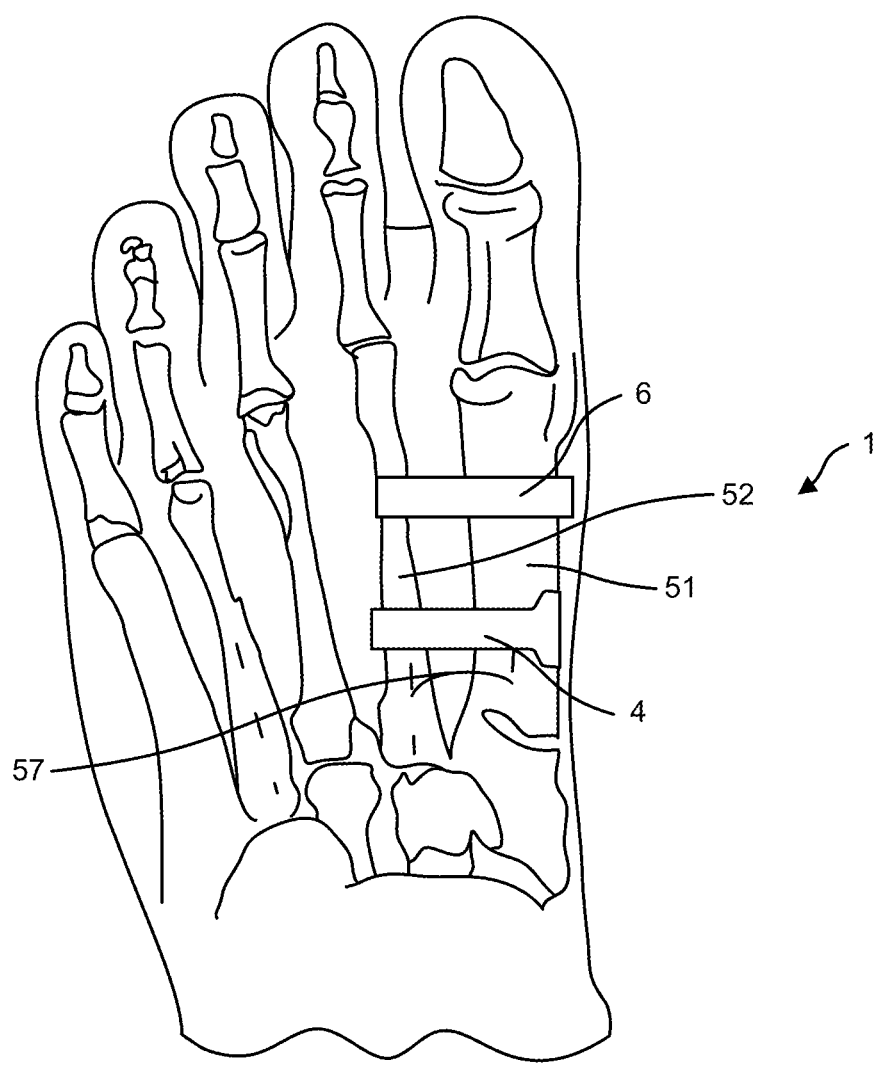
FIG. 28 depicts a corrected foot with another exemplary bunion correction implant system positioned on first and second metatarsals.
Figure 29A:
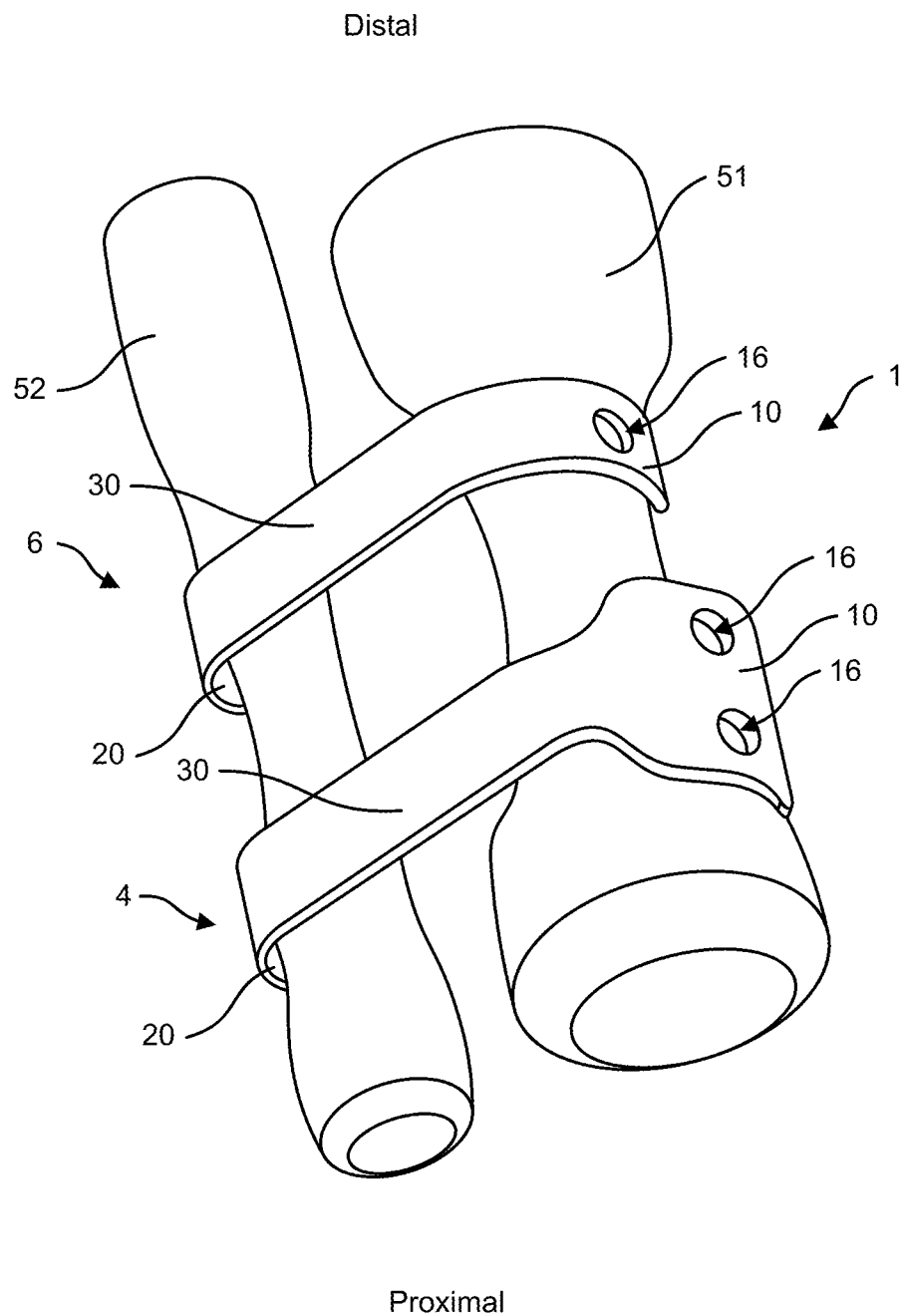
FIG. 29A depicts a top perspective view of the implant system of FIG. 28.
Figure 29B:
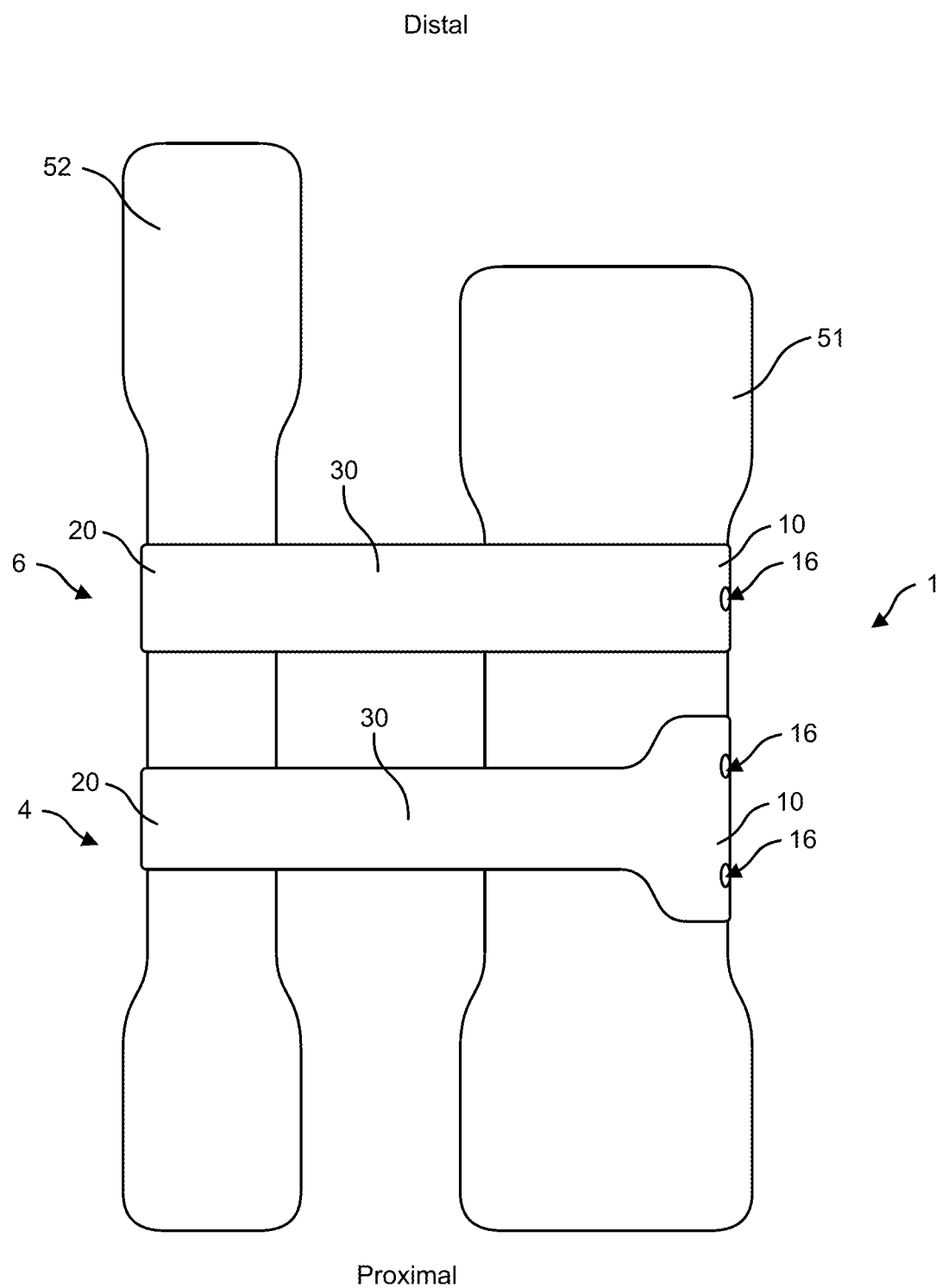
FIG. 29B depicts a top view of FIG. 29A.

As shown in FIGS. 28-29B, in one embodiment, implants 4, 6 of a bunion correction system 1 may include a first bone engaging feature 10 at one end that is constructed in a manner to engage the first metatarsal bone 51, and a second bone engaging feature 20 at the other end that is constructed in a manner to engage the second metatarsal bone 52.

Figure 31:
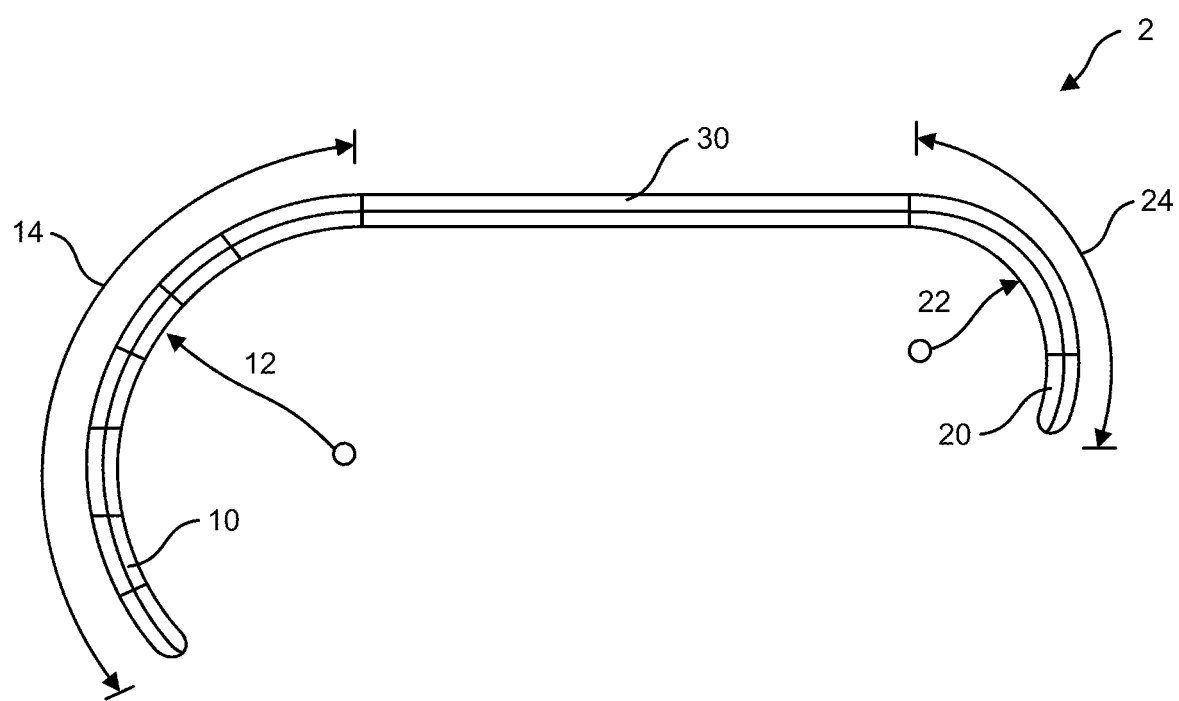
FIG. 31 depicts a side view of the implant of FIG. 30A.
Figure 32:
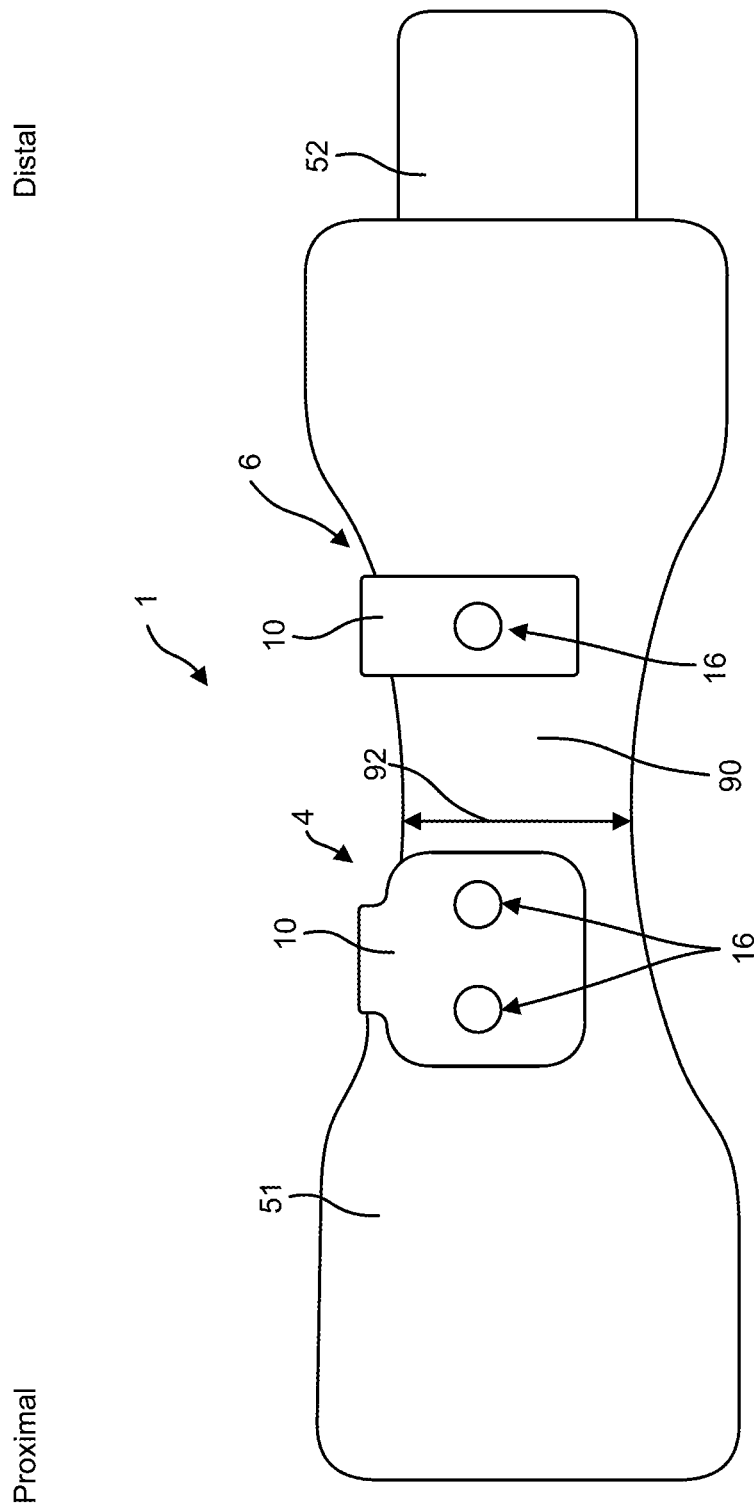
FIG. 32 depicts a medial view of the implant system of FIG. 28.
Figure 33A:
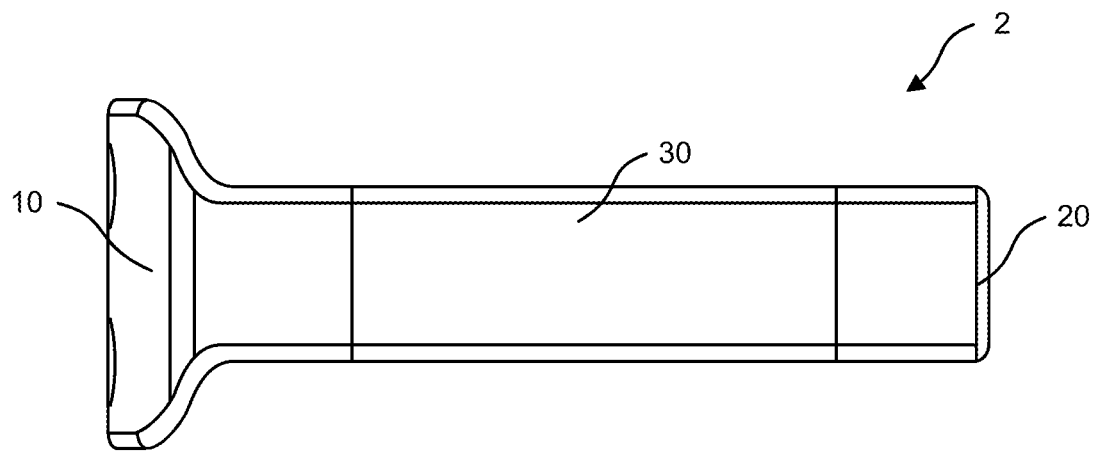
FIG. 33A depicts a top view of the implant of FIG. 30A.
Figure 33B:
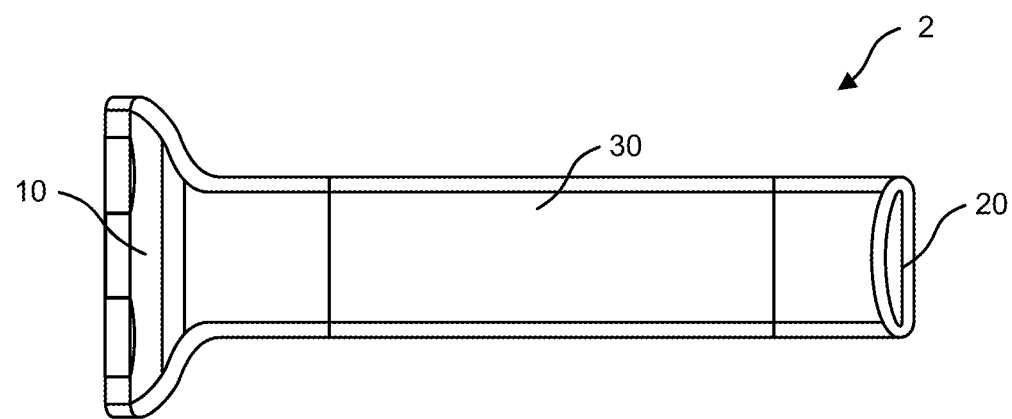
FIG. 33B depicts a bottom view of the implant of FIG. 30A.
Figure 34:
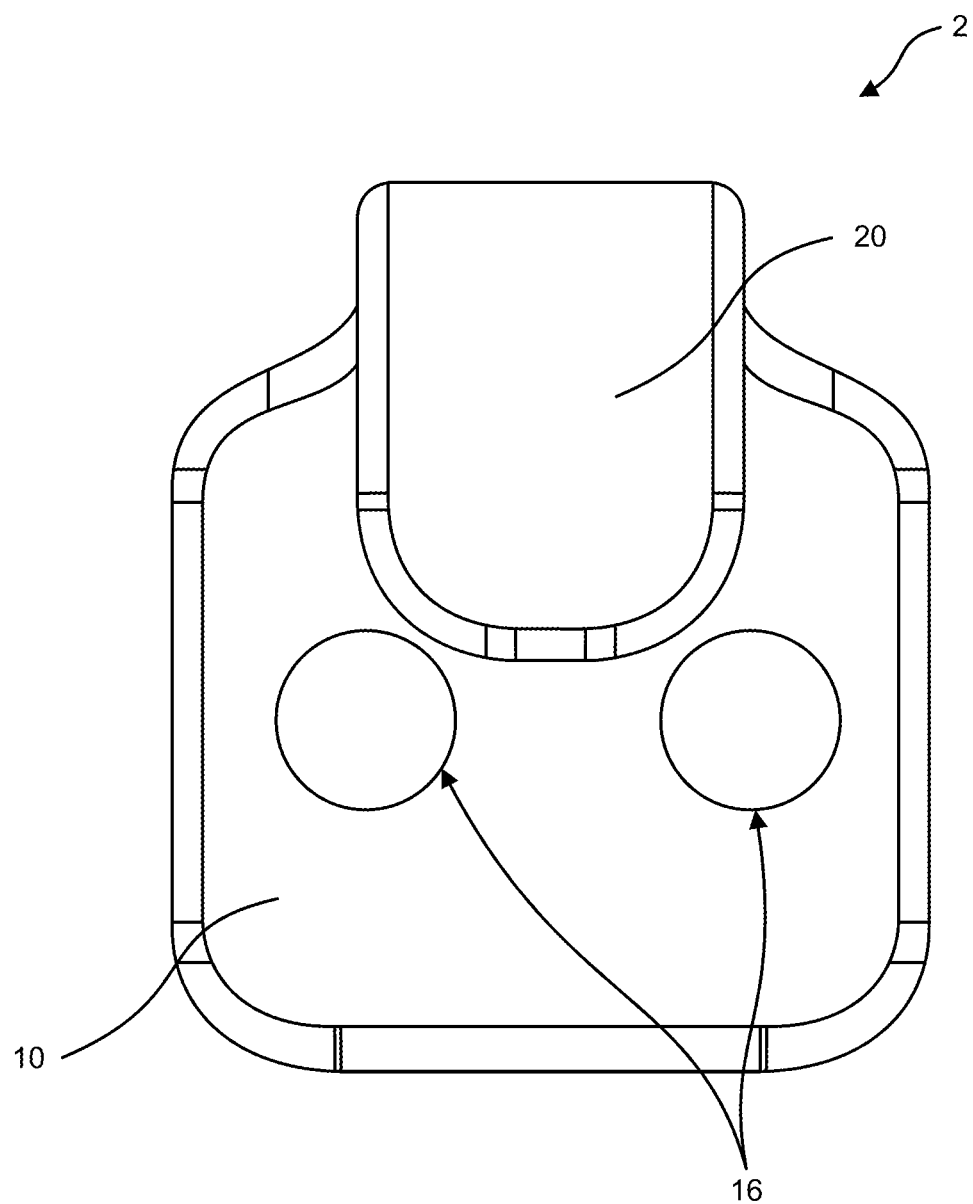
FIG. 34 depicts an end view of the implant of FIG. 30A.

In one embodiment, the bone engaging feature is shaped to partially wrap around the bone. In the embodiment shown in FIG. 31, the side profile of implant 2 may form a C-shape to hook on the lateral or medial aspect of a bone. Each bone engaging feature 10, 20 may have a specific radius of curvature and arc length. The radius of curvature and arc length of each bone engaging feature may allow each end of the implant to hook on the lateral or medial aspect of a bone, thereby partially wrapping around the bone. First bone engaging feature 10 has a radius of curvature 12 and arc length 14. Likewise, second bone engaging feature 20 has a radius of curvature 22 and arc length 24. The radius of curvature of each bone engaging feature may range from about 1 mm to 25 mm. The arc length of each bone engaging feature may range from about 1 mm to about 150 mm. As shown in FIG. 29A, first bone engaging feature 10 of the proximal implant 4 hooks on the medial aspect of the first metatarsal 51 and partially wraps around the first metatarsal 51. Similarly, as shown in FIG. 29B, second bone engaging feature 20 of the proximal implant 4 hooks on the lateral aspect of the second metatarsal 52 and partially wraps around the second metatarsal 52. Depending on its radius of curvature and arc length, the bone engaging feature may partially wrap around bone by extending to a certain dorsal-ventral depth along the lateral or medial aspect of the bone. In some embodiments, as shown in FIG. 32, the first bone engaging feature 10 partially wraps around the first metatarsal 51 by extending down to more than half the dorsal-ventral depth 92 of the medial aspect 90 of the first metatarsal 51.

Figure 35:
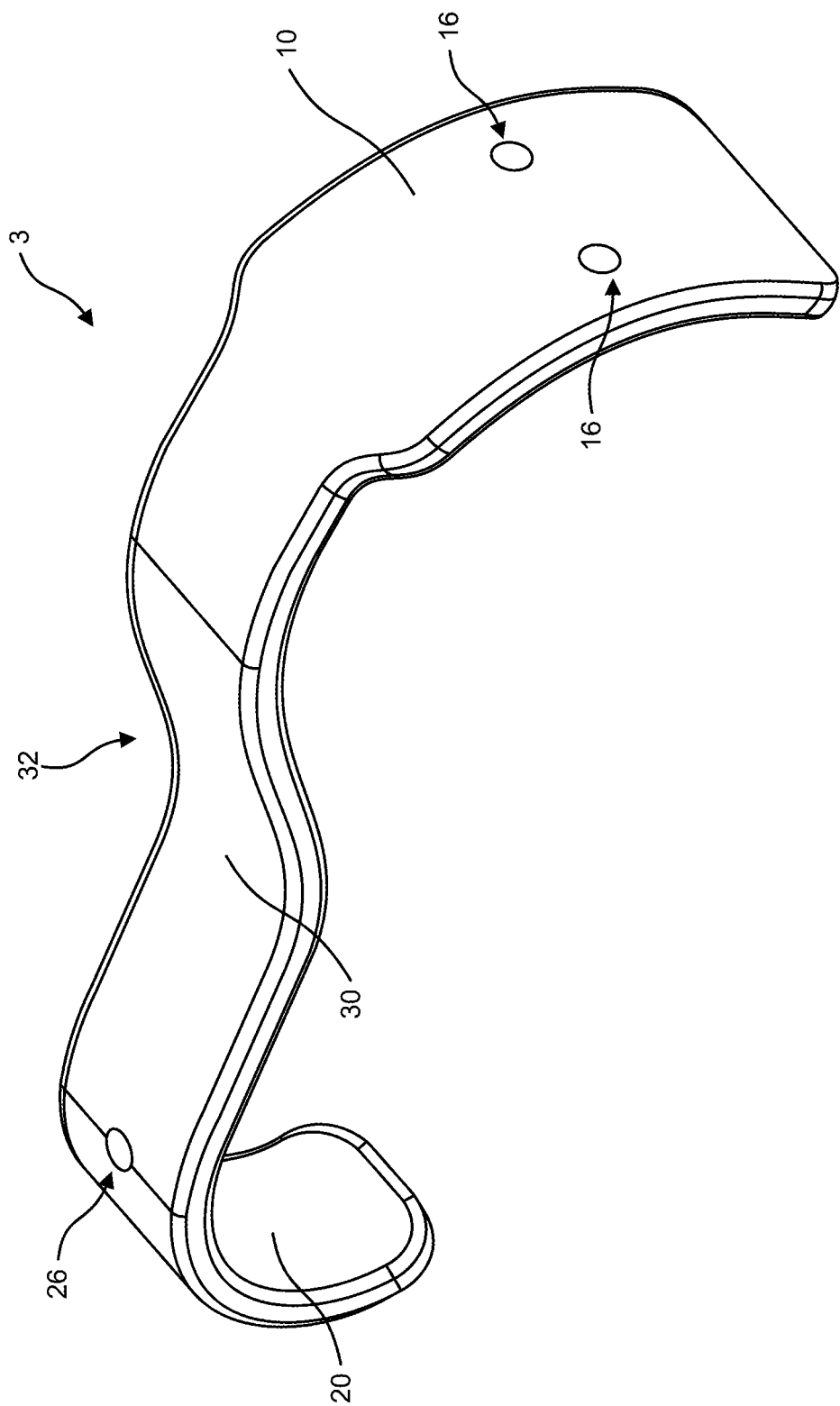
FIG. 35 depicts an elevational perspective view of another exemplary bunion correction implant system.

FIGS. 29A and 29B illustrate an embodiment in which bone engaging features 10, 20 include a rounded shape that permits the end of the implant to wrap around the bone, combined with bone anchor holes 16, which also promote engagement between the implant to bone. Bone anchor holes may be positioned anywhere along the implant. As illustrated in FIG. 35, in some embodiments, an implant 3 may have an intermediate portion 30 that includes a dorsal bone anchor hole 26.

Figure 36:
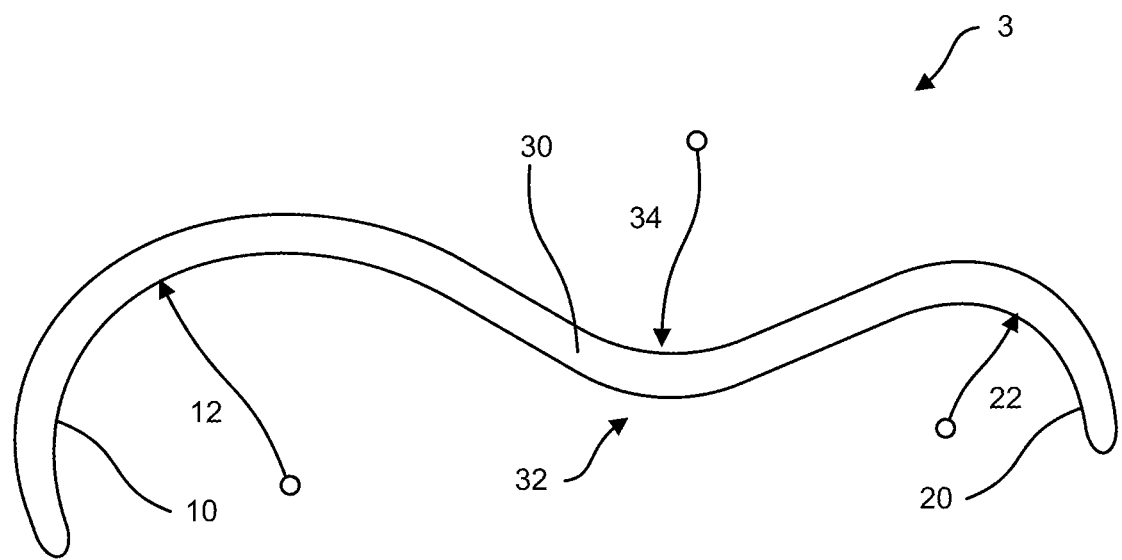
FIG. 36 depicts a side view of the implant of FIG. 35.
Figure 37B:
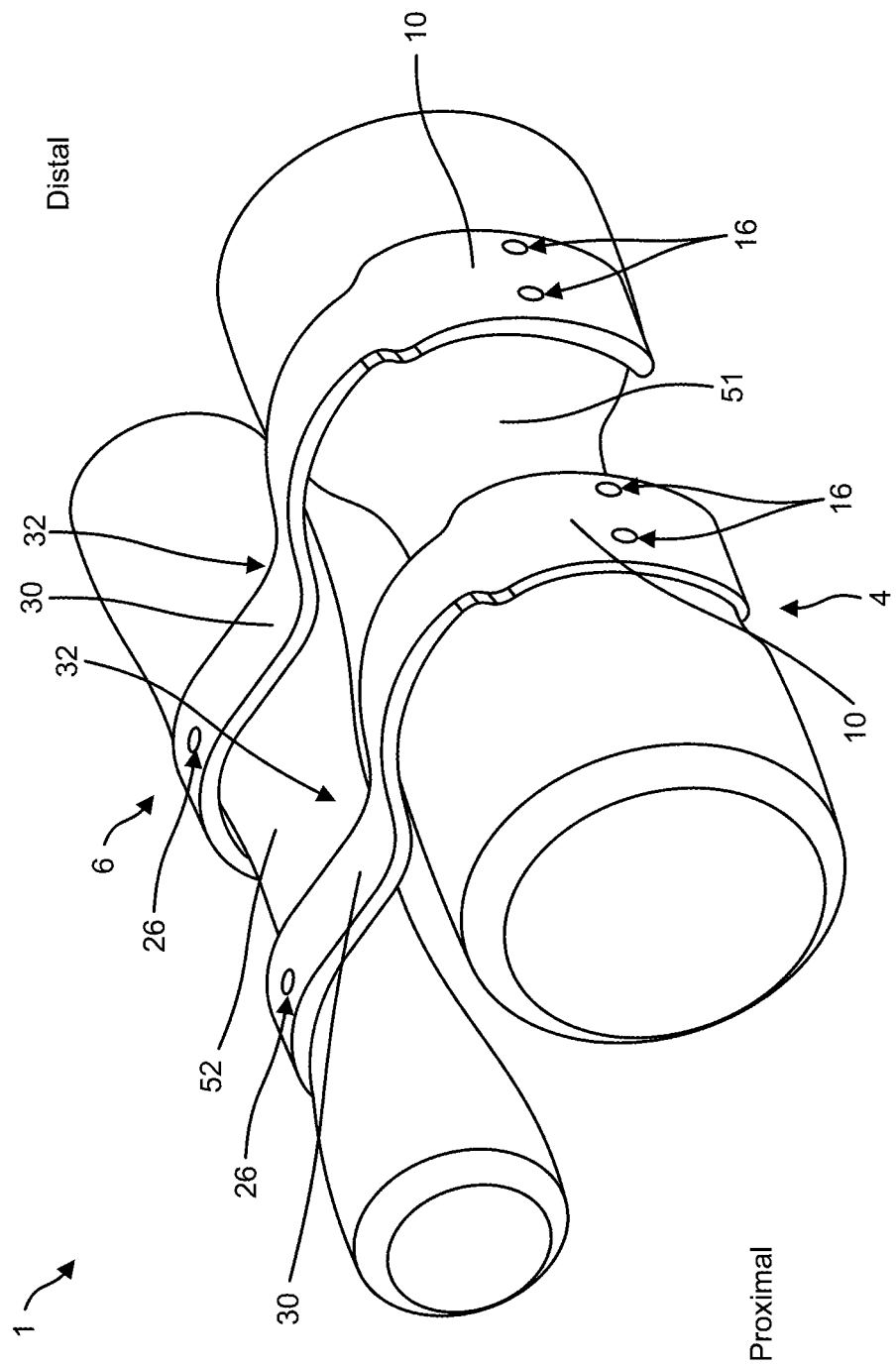
FIG. 37B depicts another elevational perspective view of FIG. 37A.

As can be appreciated, the implant exerts an appropriate tension force between the metatarsals to draw the first toward the second metatarsal, urging the improperly positioned metatarsal back toward its correct anatomical position. In one embodiment, as shown in FIGS. 30A, 30B, 33A and 33B, the implant includes an intermediate portion 30 connecting the first 10 and second 20 bone engaging features. In some embodiments, the intermediate portion connects only a first bone engaging feature and a second bone engaging feature such that the implant is constructed and arranged to only couple to two bones. In this particular embodiment, the intermediate portion has a substantially flat profile. In some embodiments, in order to improve the anatomical fit of the implant, the intermediate portion may include a curvature. As shown in FIGS. 35 and 36, intermediate portion 30 of implant 3 includes a curvature 32. The curvature may be positioned such that, when the implant is engaged with the metatarsals, the curvature is positioned between the metatarsals. This curvature may allow the implant to be positioned closer to the metatarsals in the ventral-dorsal direction, thereby reducing the ventral-dorsal distance from the implant to the bones. FIGS. 37A and 37B depict one embodiment in which intermediate portion 30 includes a curvature 32 positioned between the first 51 and second 52 metatarsals.

Figure 30A:
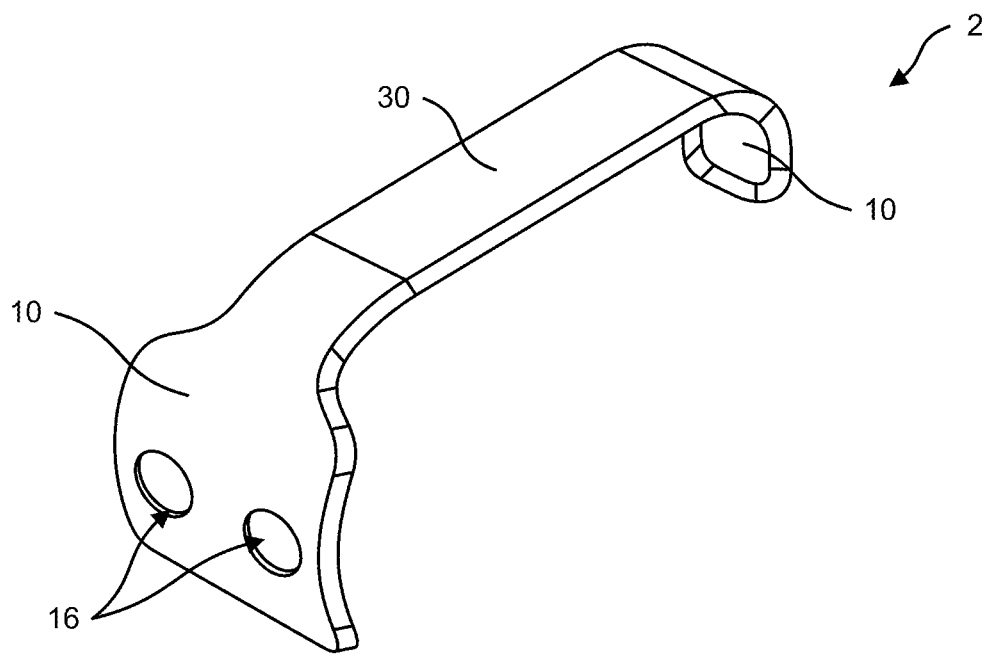
FIG. 30A depicts a top perspective view of an implant of FIG. 28.
Figure 30B:
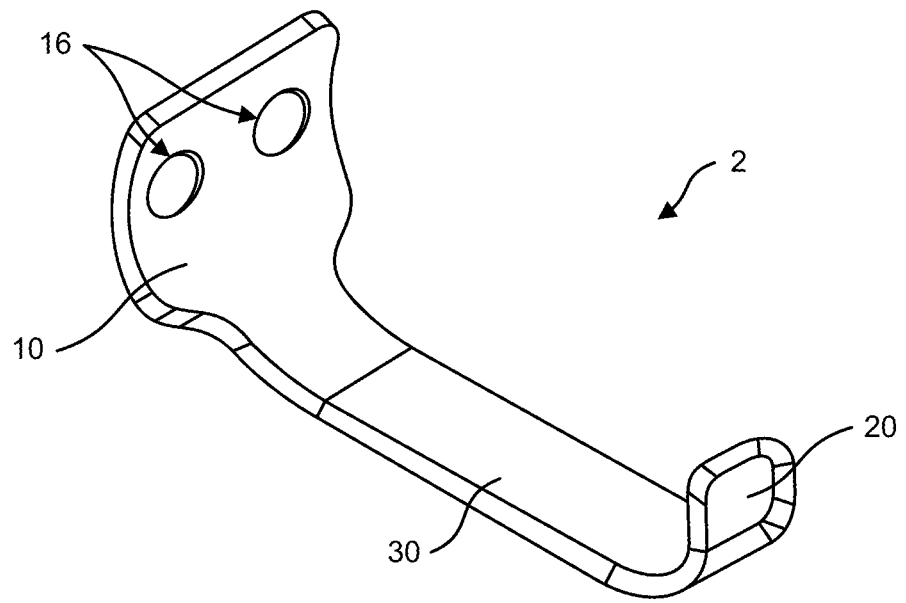
FIG. 30B depicts an underside perspective view of the implant of FIG. 30A.
Figure 30C:
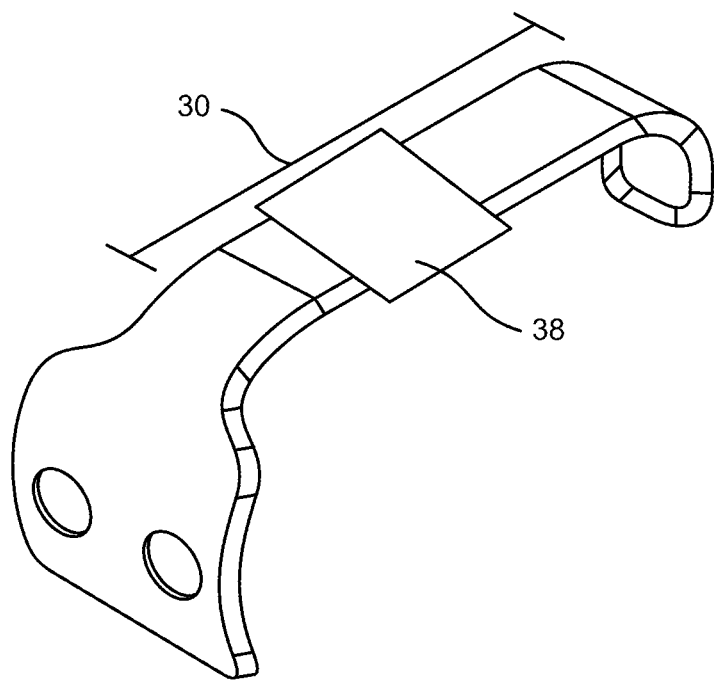
FIG. 30C depicts the of FIGS. 30A and 30B with an adjustable section.
Figure 30D:
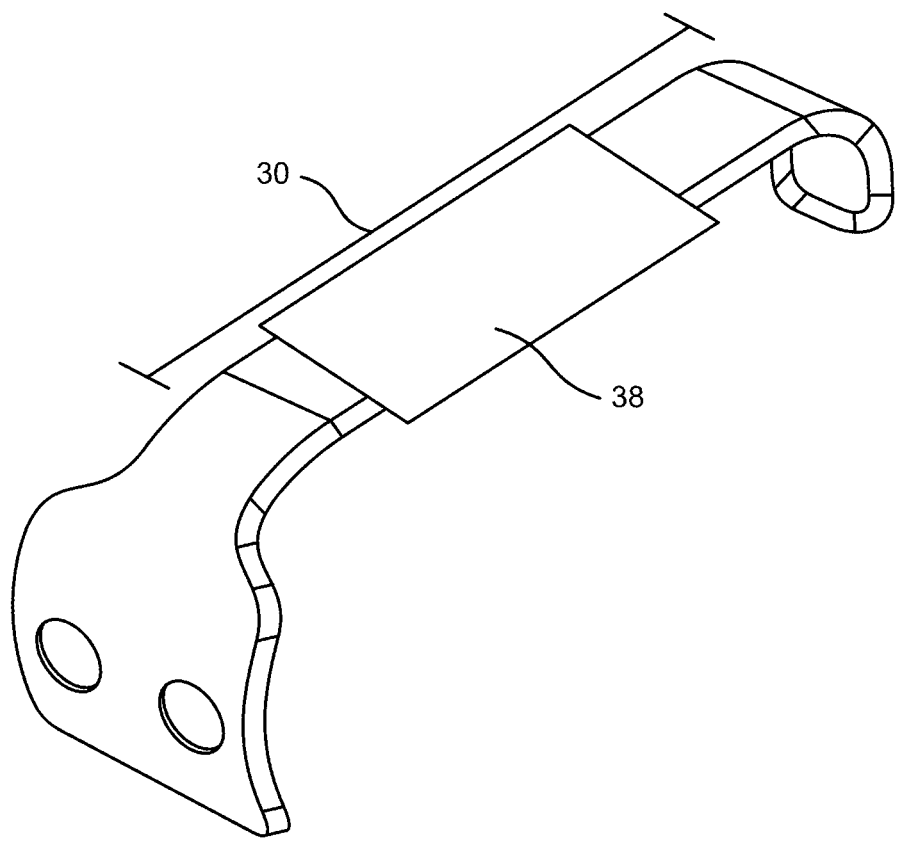
FIG. 30D depicts the implant of FIG. 30C with the adjustable section expanded.

According to one aspect, the intermediate portion may be adjustable to enhance the anatomical fit of the implant. In some embodiments, the intermediate portion may have an adjustable length, width, and/or curvature. For example, the intermediate portion may include heat shrinkable components, slidably adjustable components, and/or bendable components that permit a user to adjust the length, width, and/or curvature of the intermediate portion. For example, FIGS. 30C and 30D shows schematics of an implant with an adjustable section 38 that expands from a shorter length in FIG. 30C to a longer length in FIG. 30D, thereby increasing the overall length of the intermediate portion 30. In one embodiment, the adjustable section may comprise one or more struts that may be length-adjustable, such as a turnbuckle-like device. In another embodiment, the adjustable section may comprise multiple telescoping segments such that the intermediate portion can be expanded or compressed to various lengths. In yet another embodiment, adjustable section may include multiple removable segments. Segments may be added or removed to increase or decrease the length of the adjustable section. In another embodiment, the adjustable section may comprise two segments that can be interlocked with one another at multiple positions to enable a range of intermediate portion lengths. For example, the first segment may have a series of slots arranged linearly along the length of the first segment. The second segment may have a series of tabs arranged linearly along the length of the second segment. The tabs on the second segment may be sized to be able to slide into the slots on the first segment. The tabs and slots may be arranged such that engagement between the tabs and slots locks the tabs in place, e.g., by shaping tabs into a hooked configuration that can hook onto the slots, by interference fit between the tabs and the slots, or by other suitable arrangement. The length of the intermediate portion is adjusted by sliding the two portions relative to one another and changing the amount of overlap between the two portions. A maximum amount of overlap between the two portions enables a minimum intermediate portion length, while a minimum amount of overlap between the two portions enables a maximum intermediate portion length. The adjustable section may span the entire length and width of the intermediate portion, or the adjustable section may be only one section of the intermediate portion. In addition, the intermediate portion may be bendable, either by hand or with a tool such as a plate bender, to create a curvature suitable to the patient's anatomy. The intermediate portion may be adjusted preoperatively or intraoperatively.

According to one aspect, the intermediate portion may be located on only one side of the bone. In some embodiments, where the implant is used in a foot, the intermediate portion may be located only dorsal to the metatarsals, such that the intermediate portion is positioned above the metatarsals, as opposed to between the metatarsals or below the metatarsals. Such an arrangement may provide increased patient comfort and may require a less invasive implantation procedure.

Figure 37C:
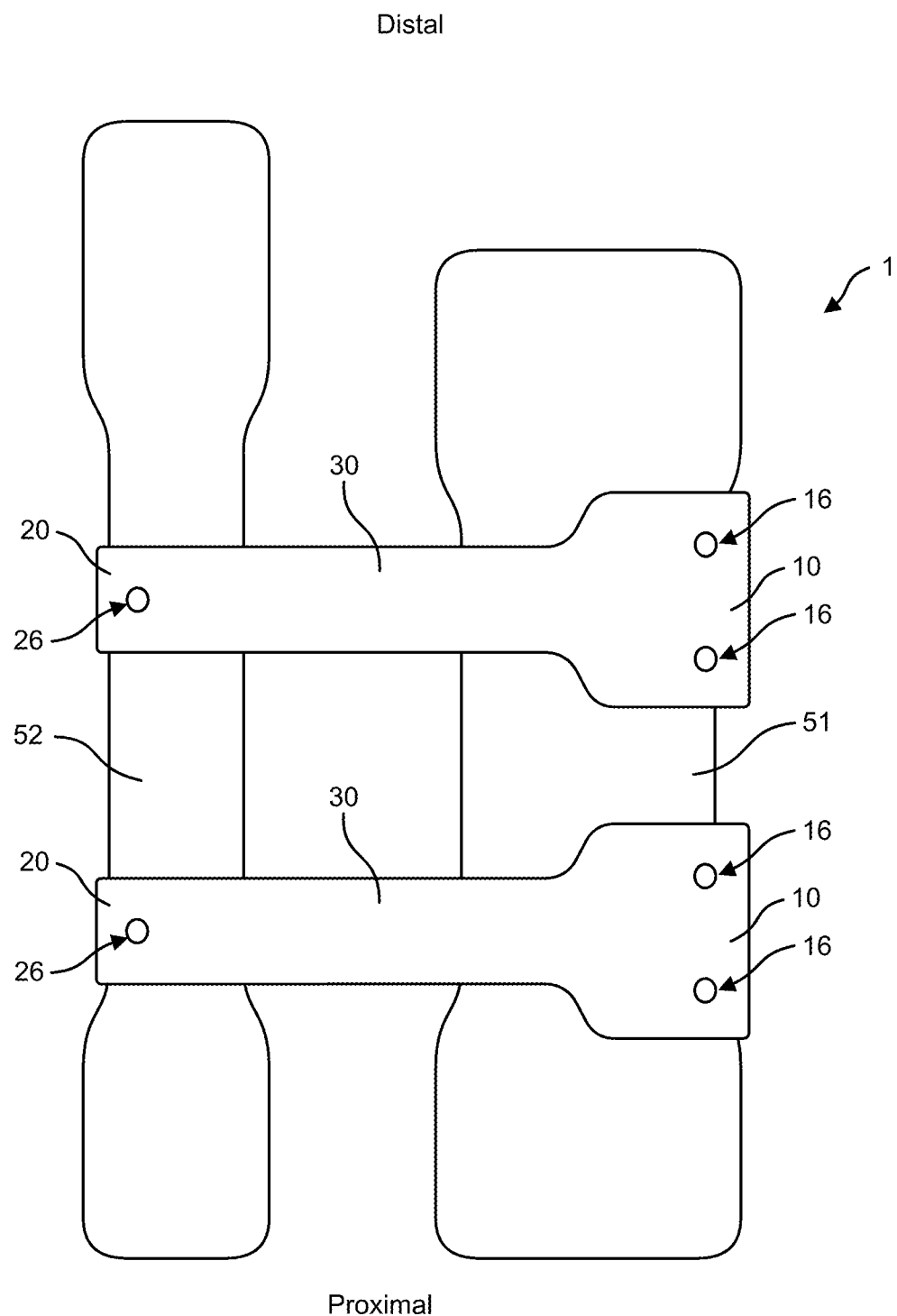
FIG. 37C depicts a top view of FIG. 37A.

According to another aspect, the intermediate portion may contact bone. In some embodiments, the intermediate portion may contact the dorsal aspect of the metatarsals. In some embodiments, the intermediate portion may include at least one bone anchor hole arranged to accept an anchoring element that anchors the implant to the bone. As shown in FIGS. 37A-37C, dorsal bone anchor hole 26 is arranged to accept an anchoring element that anchors the implant to the dorsal aspect of the second metatarsal 52. In some embodiments, the intermediate portion may include surface roughness or other suitable feature that encourages ingrowth of tissue into the intermediate portion to help hold the implant in place. In some embodiments, the surface roughness or other surface treatment is applied only to the underside surface of the intermediate portion that contacts bone, and not to the top surface of the intermediate portion facing away from the bone.

According to one aspect, the width of the implant in the distal-proximal direction is configured to provide a sufficient surface area of contact between the implant and the bone. A larger surface area of contact may permit the implant to better attach to the bone. In some instances, a wider distal-proximal width may permit an increased number of anchoring elements to fit on the implant. On the other hand, the width of the implant may be limited by the anatomy of the patient and by considerations of invasiveness and comfort. For example, wider implants may require more extensive incisions during implantation and may hinder movement of the foot. Arrangements may be selected depending on the patient's anatomy. For example, if there is sufficient surface area on the bone at the implantation site, an enlarged bone engaging feature may be used. In some embodiments, the width of the implant in the distal-proximal direction may be uniform. For example, as shown in FIGS. 29A and 29B, distal implant 6 has a constant distal-proximal width throughout the entire length of the device. The first bone engaging feature 10, second bone engaging feature 20, and intermediate portion 30 of distal implant 6 all have the same width. In other embodiments, the distal-proximal width of the implant may be non-uniform. For example, as shown in FIGS. 29A and 29B, proximal implant 4 has an enlarged first bone engaging feature 10, such that the distal-proximal width at the first bone engaging feature 10 is wider than the intermediate portion 30 and the second bone engaging feature 20. Similarly, in FIGS. 33A-36, implant 2 has an enlarged first bone engaging feature 10 such that the distal-proximal width at the first bone engaging feature 10 is wider than the intermediate portion 30 and the second bone engaging feature 20. In addition, FIGS. 29A and 29B also show that the distal-proximal width of proximal implant 4 steps down from a wider width at first bone engaging feature 10 to a narrower width that is uniform from the intermediate portion 30 to the second bone engaging feature 20. Of course, it should be appreciated that the present invention is not limited in this respect and other arrangements may be employed. In one embodiment, the proximal implant may have a constant distal-proximal width, while the distal implant may have an enlarged first and/or second bone engaging feature. In another embodiment, the distal implant may have a constant distal-proximal width, while the distal implant may have an enlarged first and/or second bone engaging feature. In another embodiment, the distal and proximal implants may both have constant distal-proximal widths. In yet another embodiment, the distal and proximal implants may both have enlarged first and/or second bone engaging features. In yet another embodiment, the first bone engaging feature, the second bone engaging feature, and the intermediate portion may all have different distal-proximal widths from one another.

The implant is implanted into the body of a patient according to various aspects. In the case of treating hallux valgus or tailor's bunion, a surgical procedure is required for implantation of the implant. Prior to surgery, images may be taken of the implantation site and anatomical measurements may be made. Images may include X-Rays, Magnetic Resonance Imaging (MM), Computed Tomography (CT) scans, or other suitable images. Anatomical measurements may include the intermetatarsal angle (the interior angle between the first and second metatarsals for hallux valgus or the interior angle between the fourth and fifth metatarsals for tailor's bunion), the distance between the first and second metatarsophalangeal (MTP) joints for hallux valgus (fourth and fifth MTP joints for tailor's bunion), curvature of the metatarsals, etc. Based on the images and anatomical measurements, a suitable-sized implant is chosen. Depending on the anatomy of the patient, the implant may be used as a proximal implant or a distal implant. As shown in FIGS. 29A and 29B, an implant system 1 may include both a proximal implant 4 and a distal implant 6.

In some embodiments, an implant system composed of multiple implants may be used. In some cases, the use of multiple implants may depend on the patient's intermetatarsal angle. In general, a normal intermetatarsal angle is less than about 9 degrees. In some embodiments, if the subject's intermetatarsal angle is less than about 12 degrees, a single implant may be sufficient. In some embodiments, if the subject's intermetatarsal angle is over about 12 degrees, two implants may be used. As shown in FIGS. 28, 29A, 29B, and 37A-38, a first implant 4 may be implanted at a proximal location and a second implant 6 may be implanted at a distal location. Of course, it should be appreciated that the present invention is not limited in this respect and other implantation positions may be used. For example, the first and second implants may be implanted closer or further away from each other. First implant 4 may sit at a position more or less proximally than that shown in FIGS. 29A and 29B, and the second implant 6 may sit at a position more or less distally than that shown in FIGS. 29A and 29B.

According to one aspect, first and second implants may be connected together to form a double-construct implant. For example, the double-construct implant may include a connector or section that joins first and second implants together. The connector may be arranged to be positioned in the space between the metatarsals upon implantation such that the double-construct implant forms an H-shape configuration. Alternatively, in some embodiments, the connector joining the first and second implants may be a plate that is wider than the space between the metatarsals. In another embodiment, the double-construct implant may have multiple connectors that join the first and second implants together. First and second implants may be connected together in any suitable way to form a double-construct implant, as this aspect is not limited in this regard. In some embodiments, the connector or connectors may be adjustable to enhance the anatomical fit of the implant. In some embodiments, the connector may have an adjustable length and/or thickness. For example, the connector may include heat shrinkable components, slidably or rotatably adjustable components, and/or bendable components that permit a user to adjust the length, width, and/or curvature of the connector. In another embodiment, the connector may include multiple removable segments. Segments may be added or removed to increase or decrease the length of the connector. In addition, the connector may be bendable, either by hand or with a tool such as a plate bender, to create a curvature suitable to the patient's anatomy. The connector may be adjusted preoperatively or intraoperatively.

Figure 38:
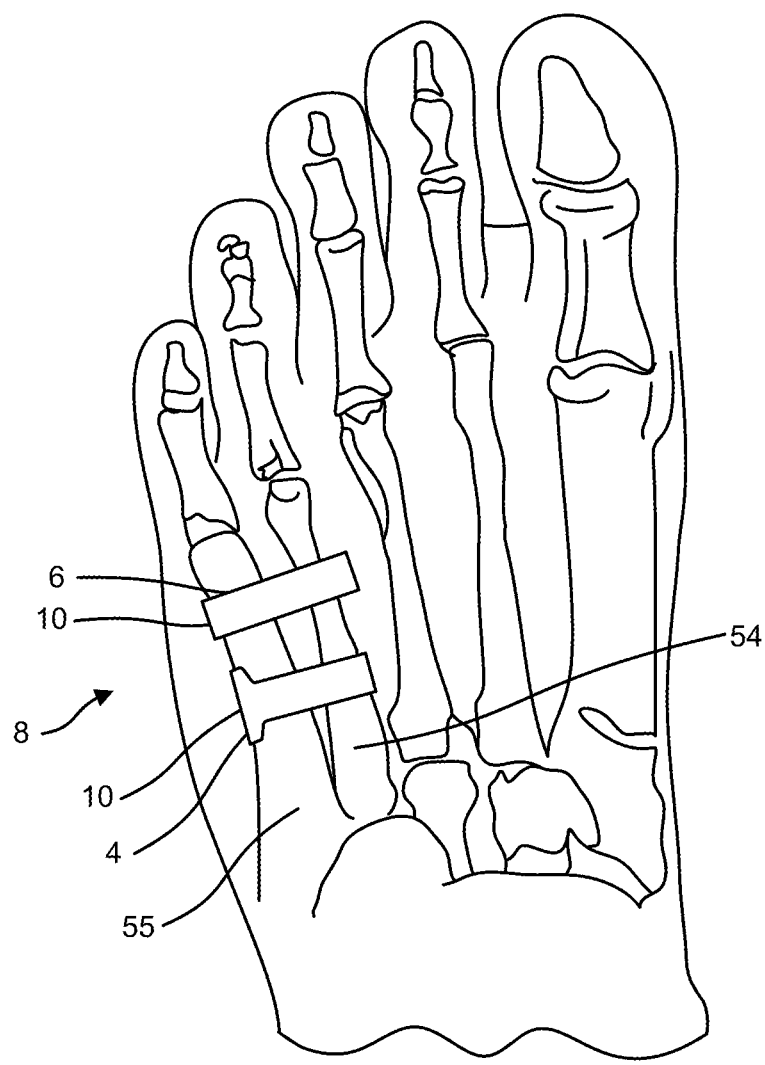
FIG. 38 depicts a corrected foot with an exemplary bunion correction implant system positioned on the fourth and fifth metatarsals in accordance with an aspect.

According to one aspect, the implant is not limited to use with the first and second metatarsals. In some embodiments, the implant may be used to treat a condition called tailor's bunion, also known as a bunionette. As shown in FIG. 38, implant system 8, including proximal implant 4 and distal implant 6, may stabilize the fifth metatarsal 55 to the fourth metatarsal 54 in the same manner that the first metatarsal 51 is stabilized to the second metatarsal 52 in the treatment of hallux valgus (FIGS. 28-29B). Although FIG. 38 depicts a proximal implant 4 with an enlarged first bone engaging feature 10, and a distal implant 6 with a uniform proximal-distal width, it should be appreciated that this aspect is not limited in this regard. In one embodiment, proximal implant 4 may have a uniform proximal-distal width, and distal implant 6 may have an enlarged first and/or second bone engaging feature. In another embodiment, distal implant 6 may have a uniform proximal-distal width, and proximal implant 4 may have an enlarged first and/or second bone engaging feature. In yet another embodiment, both implants 4,6 may have uniform proximal-distal widths. In other embodiments, a single implant or a double-construct implant may be used. Any arrangement suitable to fit the patient's anatomy may be used, as this aspect is not limited in this regard.

According to one aspect, the implant may include one or more flexure features that permit the metatarsals that are engaged by the implant to move relative to one another after the implant has been implanted. As a result, even with the implant implanted inside the patient's foot, the metatarsals of the patient's foot may have some degree of freedom to move relative to one another. In some cases, permitting relative movement between the engaged metatarsals may provide any one or combination of the following: improve comfort, decrease mechanical stresses or other wear on the implant, decrease mechanical stresses or other wear on the biological tissue surrounding the implant, improve the longevity of the implant or decrease the probability of post-operative complications. In some embodiments, the implant may include one or more flexure features that permit relative movement between the engaged metatarsals in the dorsal-ventral direction. Alternatively, or in addition, the one or more flexure features may permit movement between the engaged metatarsals in the lateral-medial direction. The implant may also permit the engaged metatarsals to rotate relative to one another about one or more flexure axes. The flexure feature can be any suitable arrangement that permits relative movement between the engaged metatarsals in the dorsal-ventral direction and/or the lateral-medial direction.

Figure 39A:
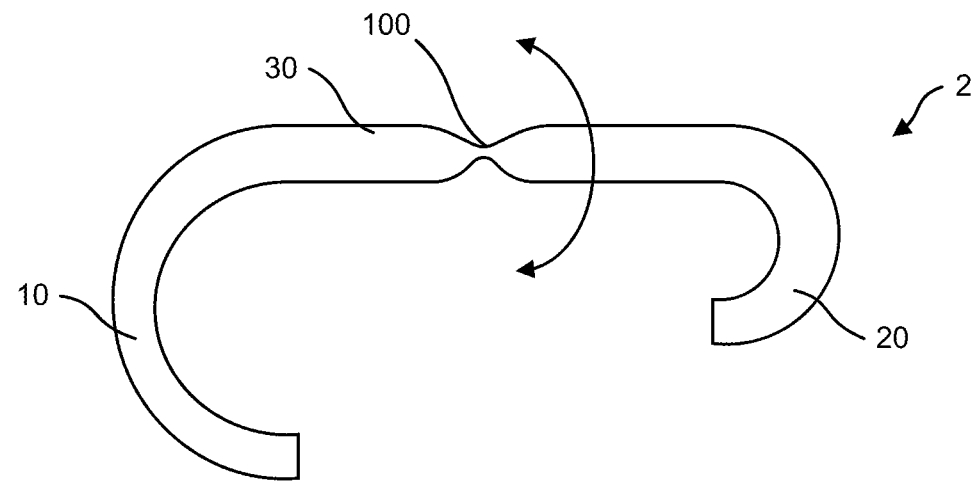
FIG. 39A depicts a side view of an exemplary bunion correction implant including a flexure feature.
Figure 39B:
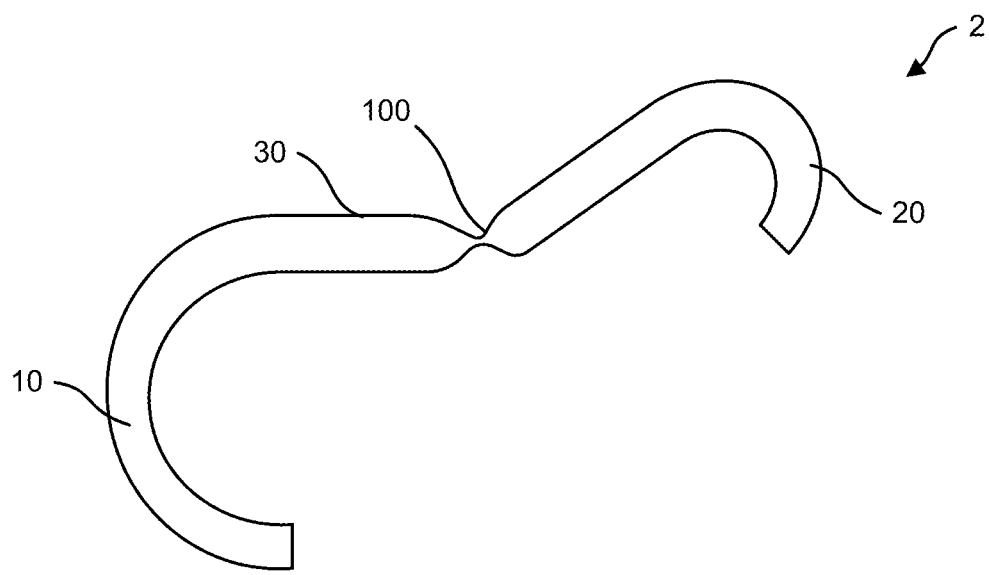
FIG. 39B depicts relative movement of first and second bone engaging features of the implant of FIG. 39A.
Figure 40:
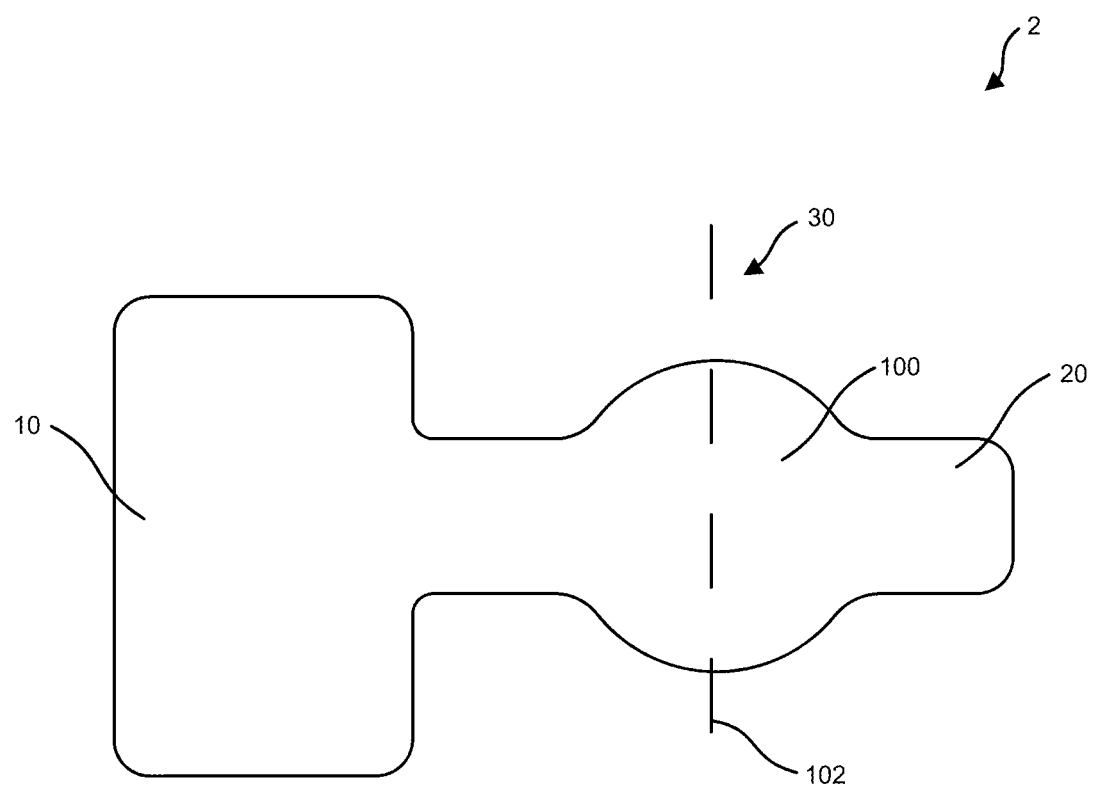
FIG. 40 depicts a top view of the implant of FIG. 39A.
Figure 42A:
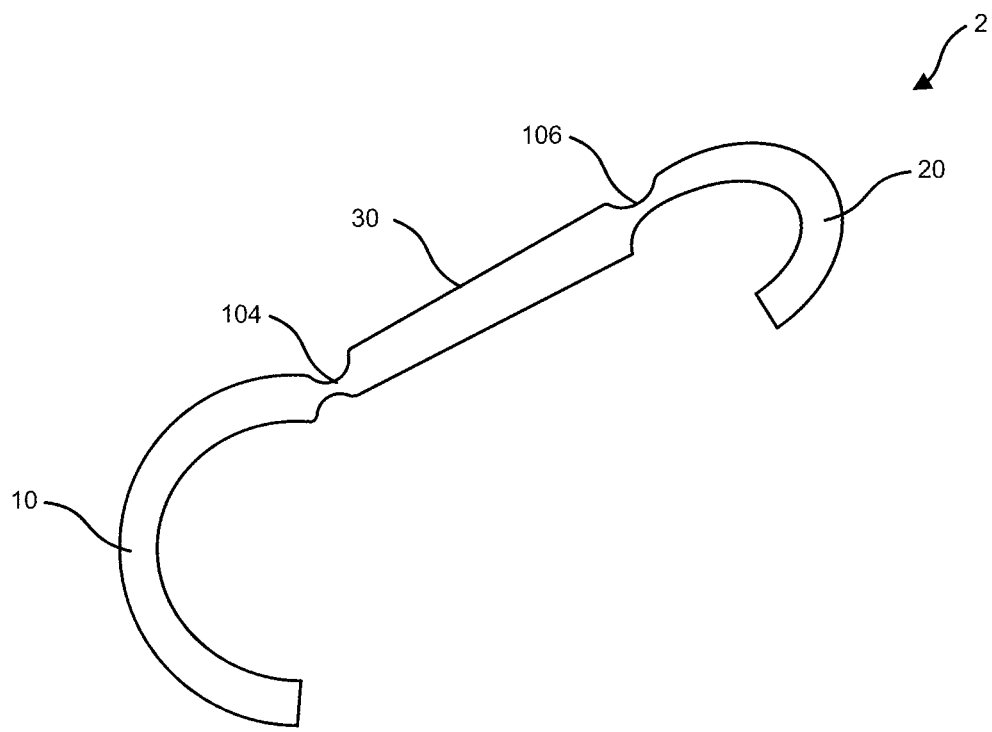
FIG. 42A depicts the implant of FIG. 41 in a first mode of operation.
Figure 42B:
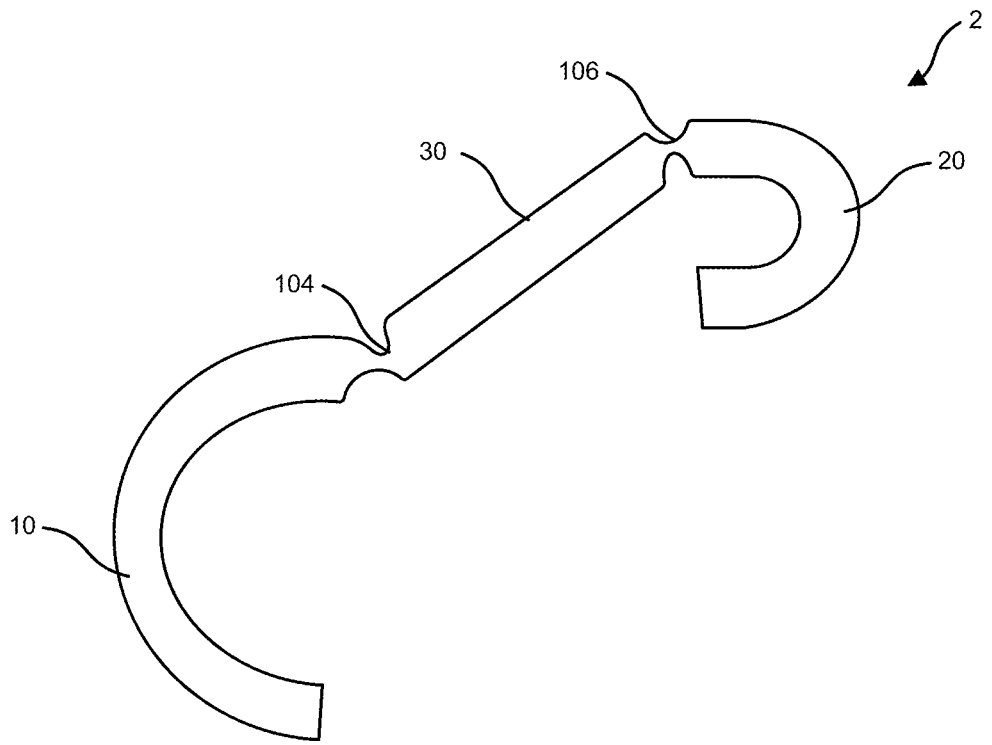
FIG. 42B depicts the implant of FIG. 41 in a second mode of operation.

In some embodiments, the flexure feature comprises a region of decreased depth in the dorsal-ventral direction relative to the rest of the intermediate portion and/or the rest of the implant. The decreased depth of the flexure feature in the dorsal-ventral facilitates flexing of the implant at the flexure feature. For example, in one embodiment, shown in FIGS. 39A and 39B, the intermediate portion 30 of implant 2 includes a flexure feature 100, which is a region of decreased depth in the dorsal-ventral direction relative to the rest of the intermediate portion 30. As depicted in FIG. 39B, flexure feature 100 permits bone engaging features 10 and 20 to rotate relative to one another. In another embodiment, shown in FIGS. 42-42B, the intermediate portion 30 of implant 2 includes two flexure features 104 and 106, which are regions of decreased depth in the dorsal-ventral direction relative to the rest of the intermediate portion 30. As depicted in FIG. 42B, flexure features 104, 106 permit bone engaging features 10 and 20 to rotate and translate relative to one another. To compensate for the decreased depth of the flexure feature in the dorsal-ventral direction, in some embodiments, the flexure feature has a wider width in the distal-proximal direction compared to the rest of the intermediate portion. FIG. 40 is a top down view of an implant 2 showing a flexure axis 102 of a flexure feature, about which the first bone engaging feature 10 can rotate relative to the second bone engaging feature 20. As seen in FIG. 40, flexure feature 100 has a wider distal-proximal width than the rest of intermediate portion 30. Without wishing to be bound by any theory, such an increased distal-proximal width may increase the cross-sectional area at the flexure feature and decrease the likelihood of fracture or other mechanical failure at the flexure feature 100. In other embodiments, however, the flexure feature may have the same or narrower distal-proximal width than the rest of the intermediate portion.

Figure 43A:
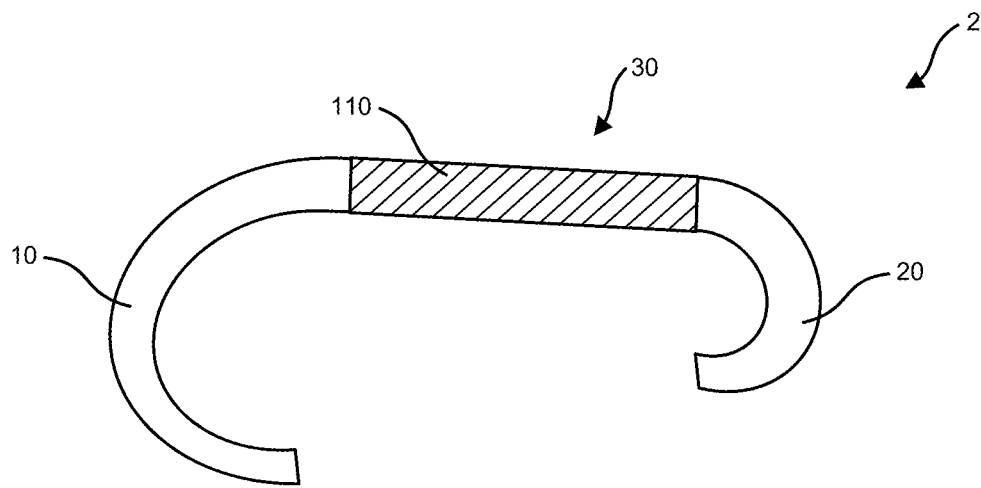
FIG. 43A depicts a side view of another exemplary bunion correction implant including a flexure feature.
Figure 43B:
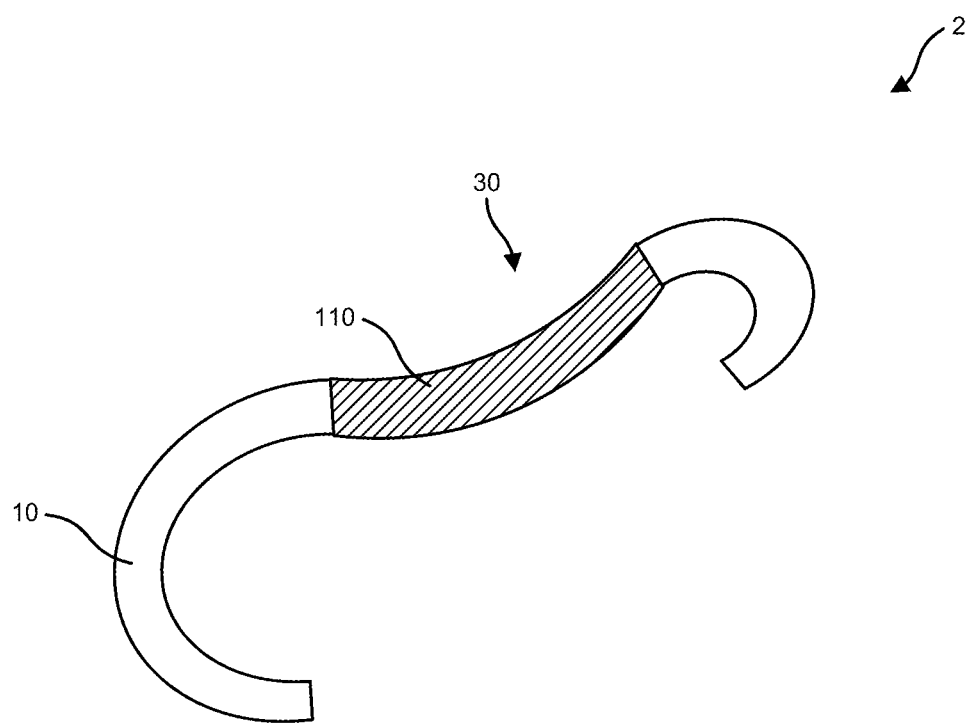
FIG. 43B depicts a side view illustrating relative movement of first and second bone engaging features of the implant of FIG. 43A.

In yet another embodiment, shown in FIGS. 43A and 43B, the flexure feature 110 comprises a region of flexible material. The flexure feature 110 is made of a material that is more flexible than that of the bone engaging features 10 and 20. The flexure feature 110 may permit the implant to flex in the dorsal-ventral direction. Alternatively, or in addition, the flexure feature 110 may permit the implant to elongate and/or shorten in the lateral-medial direction.

In yet another embodiment, shown in FIGS. 44A-46, the flexure feature comprises cables. In the embodiments shown in FIGS. 44A-45, the cables may allow the first and second bone engaging features 10, 20 to rotate, translate and twist relative to one another. In embodiments where the flexure feature comprises shorter cables, such as the embodiment shown in FIG. 46, the cables 140 may only permit rotational movement between the first and second bone engaging features. In some cases, however, shorter cables may permit rotation and some, but limited, translation and/or twisting between the first and second bone engaging features.

It should be appreciated that other flexure feature arrangements are possible. For example, the flexure feature may be an accordion-like arrangement, a sliding mechanism, may be stamped, may be bendable, may be thinner than the rest of the implant in a direction that is not limited to the dorsal-ventral direction, may have one or more reliefs, may have one large cutout in the center of the intermediate portion, leaving two side rails of material, may be a chain of links, a hinge, or any other suitable arrangement, as this aspect is not so limited.

Figure 41:
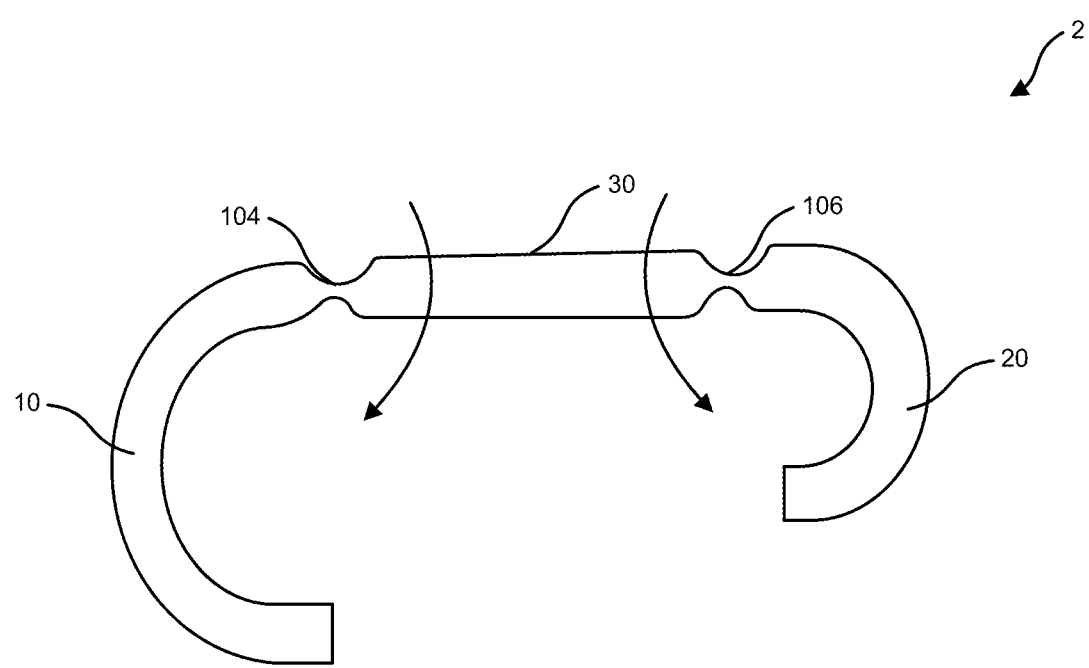
FIG. 41 depicts a side view of an exemplary bunion correction implant including two flexure features.

According to one aspect, the inclusion of one or more flexure features may impart 1, 2, 3, 4, 5 or 6 degrees of freedom to the implant. Depending on the type of flexure feature that is used, in some cases, an implant with additional flexure features may impart additional degrees of freedom to the implant. For example, the embodiment shown in FIGS. 39A and 39B includes one flexure feature 100 that imparts one degree of freedom: rotation about flexure feature 100, as seen in FIG. 39B. The embodiment shown in FIGS. 41-42B includes two flexure features 104, 106 that impart two degrees of freedom to the implant. FIG. 42A depicts the first degree of relative movement: rotation about flexure feature 104. FIG. 42B depicts the second degree of relative movement: rotation about flexure feature 106. As a result, first and second bone engaging features 10, 20 are able to rotate and translate relative to one another.

It should be appreciated that flexure features may be located at any suitable position along the implant. For example, in some embodiments where only one flexure feature is used, the flexure feature may be located closer or further away from the first bone engaging feature 10 than shown in the embodiment seen in FIGS. 39A and 39B. As another example, in some embodiments where two flexure features are used, flexure features may be located closer or further away from one another and/or from the first bone engaging feature 10 than shown in the embodiment seen in FIG. 41.

In some cases, however, a single flexure feature can impart any number of degrees of freedom to the implant. For example, in the embodiment shown in FIGS. 43A and 43B, the flexible material of flexure feature 110 may have any one or any combination of the following capabilities: flex in the dorsal-ventral direction, elongate in the lateral-medial direction, shorten in the lateral-medial direction, twist in the distal-proximal direction, or deform in any other suitable manner.

Figure 44A:
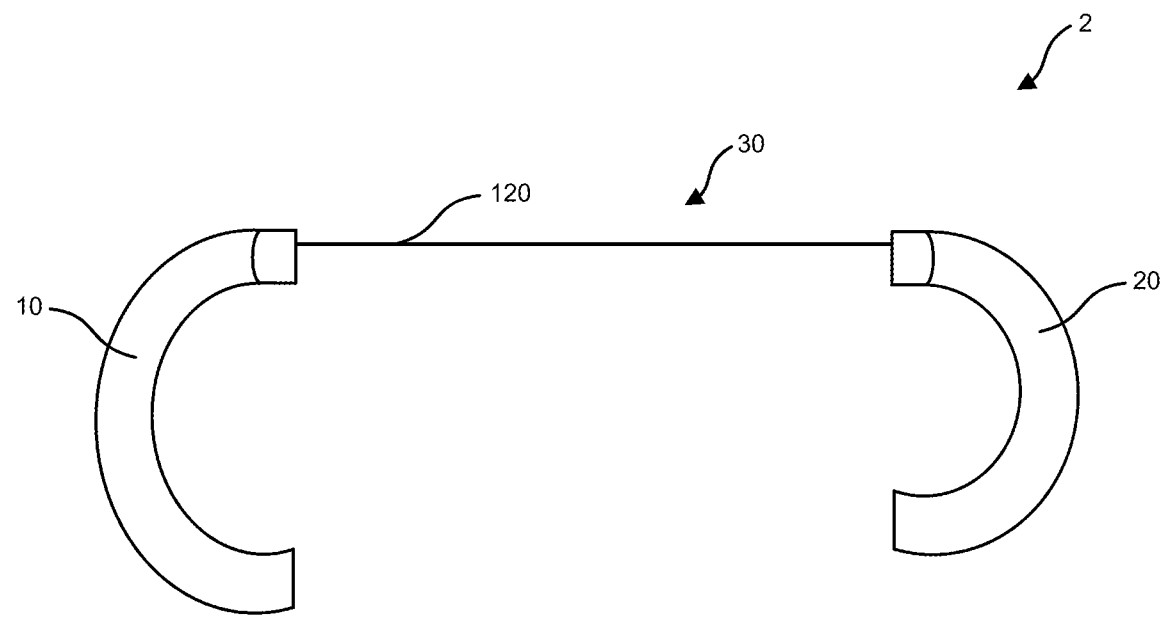
FIG. 44A depicts a side view of another exemplary bunion correction implant system.
Figure 44B:
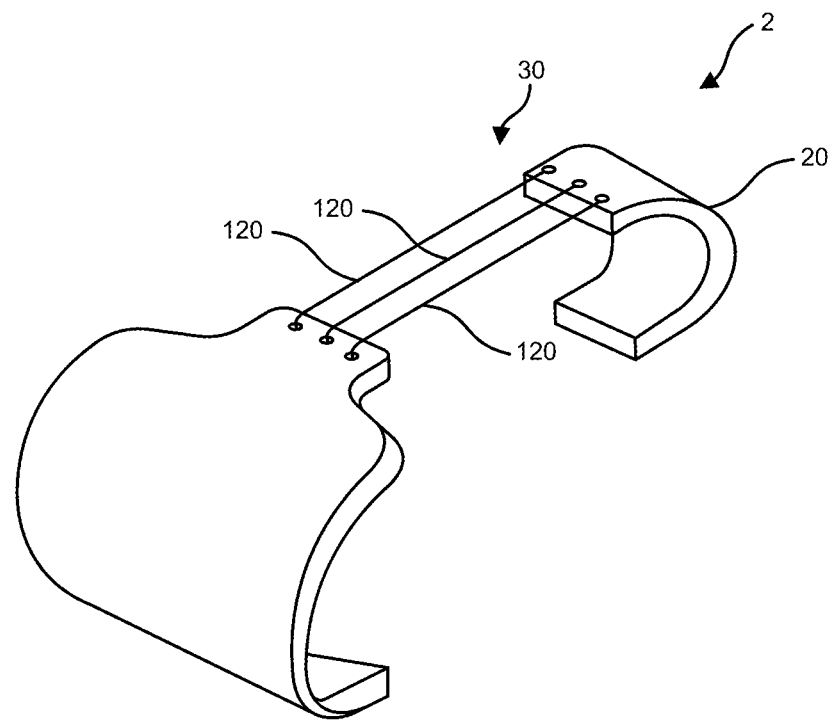
FIG. 44B depicts a top perspective view of the implant system of FIG. 44A.
Figure 45:
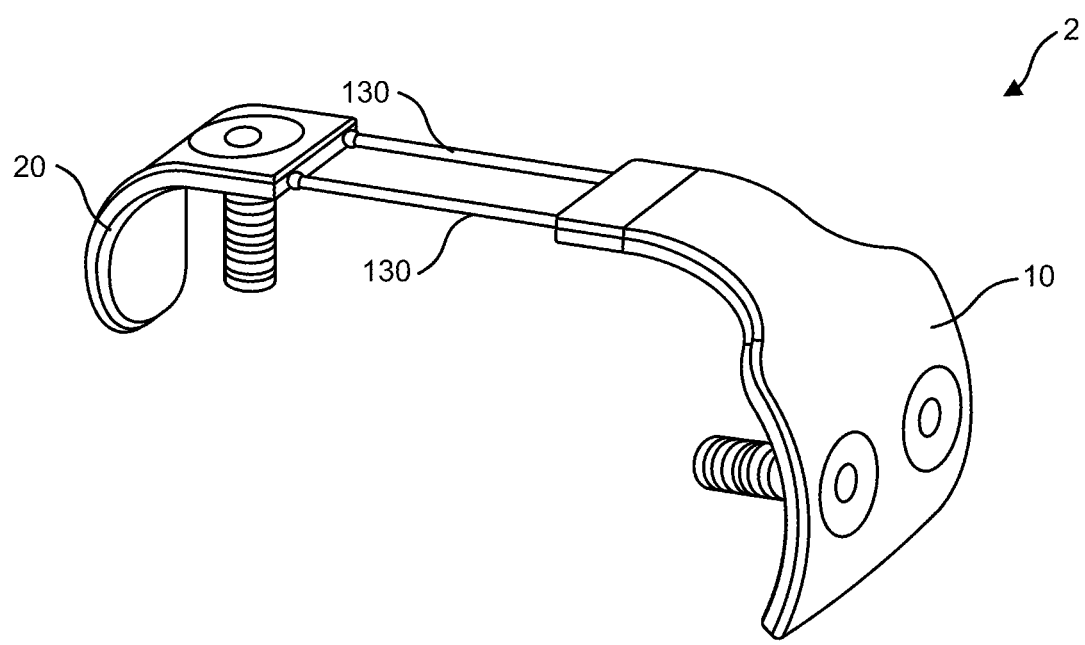
FIG. 45 depicts a top perspective view another exemplary bunion correction implant system.
Figure 46:
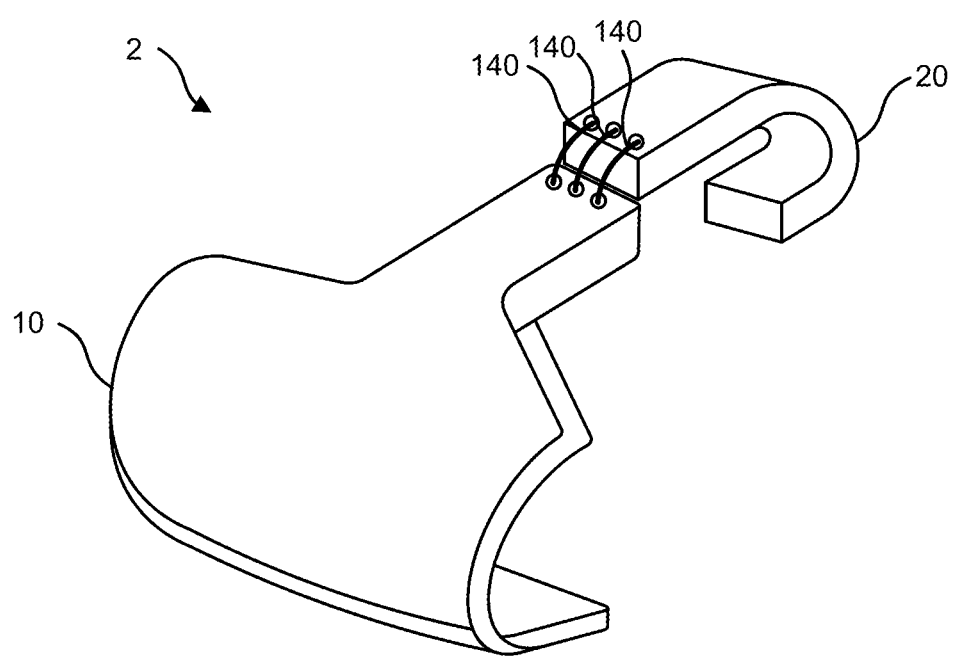
FIG. 46 depicts a top perspective view of another exemplary bunion correction implant system.

In other embodiments, as seen in FIGS. 44A-45, the flexure feature may comprise cables that impart multiple degrees of freedom. In the embodiment seen in FIGS. 44A and 44B, cables 120 may permit rotation, translation and twisting of the first and second bone engaging features 10, 20 relative to one another. In some embodiments, the cables are stretchable to impart an additional degree of freedom. In other embodiments, the cables cannot be stretched. It should be appreciated that any suitable number of cables may be used, as this aspect is not so limited. In one embodiment, depicted in FIG. 45, flexure features 130 may be one continuous loop, with one end of the loop being coupled to bone engaging feature 10 and the other end of the loop being coupled to bone engaging feature 20. In other embodiments, instead of one continuous loop, the flexure features 140 may be two separate strands that are coupled to the bone engaging features.

In some cases, the length of the cable may impact the degrees of freedom imparted to the implant. In some embodiments, longer cables such as those shown in FIGS. 44A-45 may be used to provide more than a single degree of freedom of relative movement between the first and second bone engaging features. On the other hand, in some embodiments, shorter cables may be used to restrict movement between the first and second bone engaging features to impart a single degree of freedom to the implant. In one embodiment, depicted in FIG. 46, implant 2 includes flexure features 140 in the form of short cables, creating a hinge-like connection.

It should be appreciated that the implant may have any suitable number of degrees of freedom, as this aspect is not so limited. Any suitable number of flexure features may be included and flexure feature(s) of any length may be used.

According to one aspect, in some embodiments, the flexure feature may be configured to limit the maximum distance between the engaged metatarsals so as to prevent the metatarsals from returning to their previous hallux valgus positions. For example, in the embodiment where the flexure feature is a region of flexible material as shown in FIGS. 43A and 43B, flexure feature 110 may be arranged such that it can only be shortened from its natural resting position, not elongated. As another example, in the embodiment where the flexure feature comprises one or more cables as shown in FIGS. 44A-46, the cables may be non-stretchable, thereby limiting the maximum distance between the engaged metatarsals. The flexure feature may be a chain of links, a hinge, a region of decreased depth in the dorsal-ventral direction or other suitable arrangement that permits the bone engaging features 10 and 20 to move toward one another, but restricts movement of the bone engaging features 10 and 20 away from one another beyond a maximum distance. In some embodiments, the flexure feature may be stretchable from its natural resting position, but the flexure feature has a maximum elongation length that prevents the metatarsals from returning to their previous hallux valgus positions.

The flexure feature may be coupled to the implant by any suitable means. In some embodiments, the flexure feature may be coupled to the implant by bonding, adhesive, soldering, welding, physical interlock, clamping, embedding at least one or more portions of the flexure feature within the implant, threading the flexure feature through holes in the implant, mechanical attachment, by being integrally formed with the implant as one monolithic structure, by being stamped into the implant, cutout from the implant, or by any other suitable arrangement, as this aspect is not so limited. As non-limiting, illustrative examples, the ends of flexure features 130 in the embodiment shown in FIG. 45 may be embedded within, welded to or otherwise coupled to first and second bone engaging features 10 and 20. In the case where flexure feature 130 is one continuous loop rather than two independent cables, the ends of the loop may be embedded within, welded to, or otherwise coupled to first and second bone engaging features 10 and 20.

The flexure feature may be made of titanium, nickel, nickel titanium alloy, nitinol or other shape-memory alloy, silver, gold, plastic, an elastomer, metal, metal alloy, stainless steel, a suture, FIBERWIRE, which is a multi-strand, long chain ultra-high molecular weight polythelyene (UHMWPE) core with a braided jacket of polyester and UHMWPE, or any other suitable material, as this aspect is not so limited. The flexure feature may be made from the same material as the rest of the implant or from a different material.

According to one aspect, the flexure feature may be located on only one side of the engaged bones. In some embodiments, where the implant is used in a foot, the flexure feature may be located substantially only dorsal to the metatarsals, such that the flexure feature is located at a height that is positioned above the metatarsals, as opposed to a height that is between the metatarsals or below the metatarsals. In other embodiments, the flexure feature may be located substantially only ventral to the metatarsals, such that flexure feature is located at a height that is positioned below the metatarsals, as opposed to a height that is between the metatarsals or above the metatarsals. The word "substantially" is used to include arrangements where the flexure feature bows slightly inward toward the space between the engaged metatarsals or is otherwise arranged such that a portion of the flexure feature is located at a height that is between the metatarsals. "Substantially only dorsal to or substantially only ventral to the metatarsals" includes such arrangements where a portion of the flexure feature is located at a height that is between the metatarsals.

Figure 47:
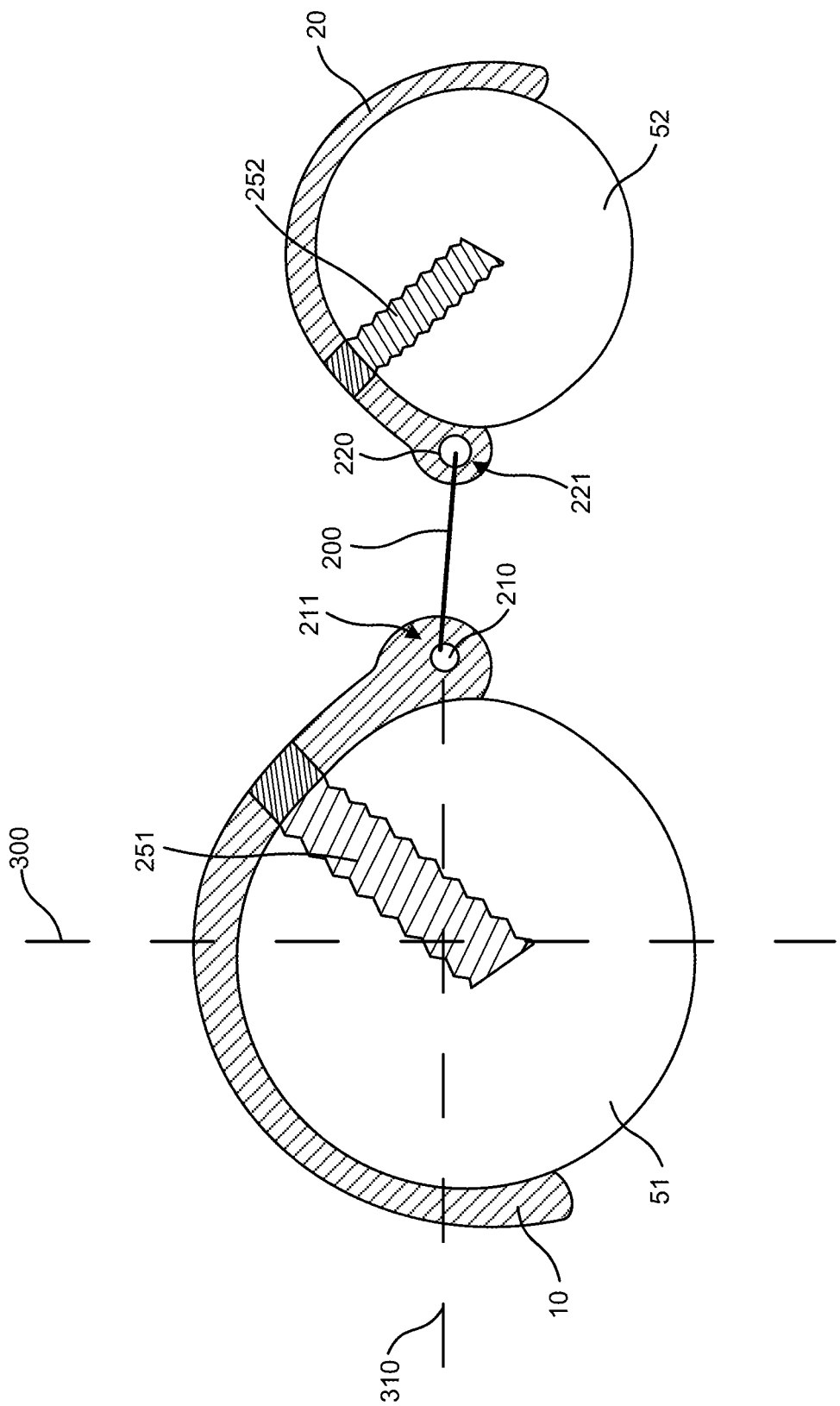
FIG. 47 depicts a side view of another exemplary bunion correction implant system engaged with first and second bones.
Figure 48:
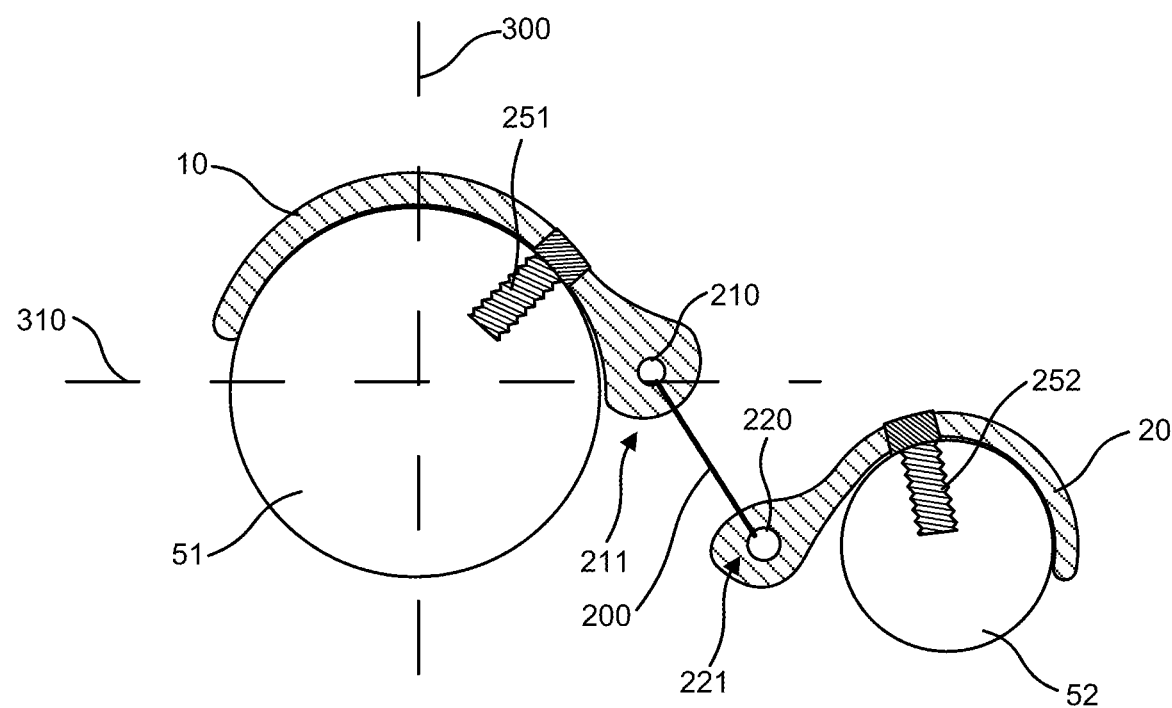
FIG. 48 depicts relative movement provided by the implant system of FIG. 47.
Figure 49:
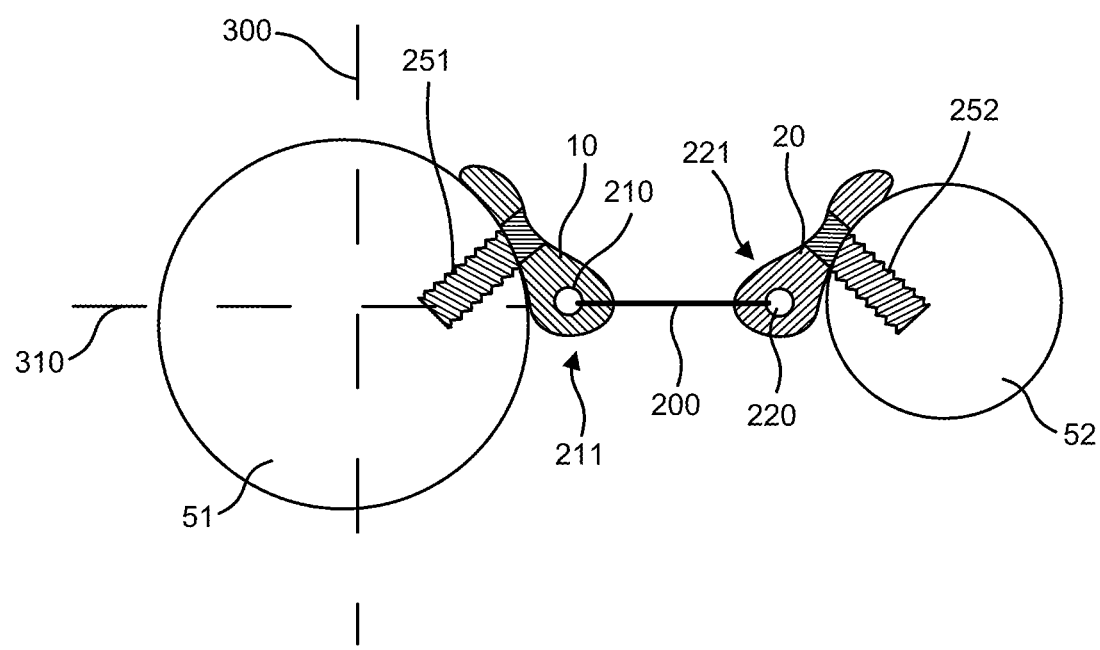
FIG. 49 depicts a side view of another exemplary bunion correction implant system engaged with first and second bones.

The Applicant has recognized that passing portions of an implant completely through a bone may decrease the structural integrity of the bone. As such, according to one aspect, the implant is configured to engage with two bones such that an intermediate portion of the implant is positioned substantially between two bones without any portion of the device (including bone anchors associated with the device) passing completely through either of the bones. As seen in FIGS. 47-49, an intermediate portion 200 of the implant (which also serves as a flexure feature) is positioned substantially between two metatarsals 51, 52, but no part of the implant passes completely through either bone.

In FIG. 47, a first bone engaging feature 10 is wrapped partially around a first metatarsal 51 and a second bone engaging feature 20 is wrapped partially around a second metatarsal 52. A flexure feature 200 couples the first bone engaging feature 10 to the second bone engaging feature 20. In such an arrangement, when the implant is engaged to the first and second bones 51, 52, the intermediate portion 200 is positioned substantially between the bones 51, 52 without passing through the bones. Further, no portion of the implant, including any associated bone anchors, passes completely through either of the bones 51, 52.

The flexure feature 200 may couple to the bone engaging features at coupling points 211, 221 on the bone engaging features. In some embodiments, the bone engaging features may include holes 210, 220 through which the flexure feature may pass. The flexure feature 200 may couple to the bone engaging features by passing through a hole 210 of the first bone engaging feature 10 and a hole 220 of the second bone engaging feature. For example, in one embodiment, the flexure feature 200 is passed through the holes 210, 220 and the flexure feature comprises a continuous loop (for example, the ends of the flexure feature may be tied to one another or otherwise attached to one another. In other embodiments, the flexure feature 200 may attach to the coupling points 211, 221 on the bone engaging features 10, 20 through the holes 210, 220 by an arrangement such as a knot, a cow hitch, via an adhesive, by welding, mechanical interlock, or by any other suitable arrangement.

In some embodiments, when the implant is engaged to the two metatarsals, the coupling portion 211 of the first bone engaging feature 10 is positioned near or substantially aligned with the horizontal plane 310 that bisects the first metatarsal through the lateral and medial aspects of the metatarsal. Similarly, the coupling portion 210 of the second bone engaging feature 20 may be positioned near or substantially aligned with a horizontal plane that bisects the second metatarsal through the lateral and medial aspects of the metatarsal. In some embodiments, when the implant is engaged to the two metatarsals, the intermediate portion 200 is positioned near or substantially along the horizontal plane 310 that bisects one of the metatarsals through the lateral and medial aspects of the metatarsal. In some embodiments, the intermediate portion 200, which may serve as or include a flexure feature (such as a cable or wire), the intermediate portion is only in tension and positioned substantially between the bones engaged by the device.

As discussed previously, a flexure feature may permit the metatarsals that are engaged by the implant to move relative to one another after the implant has been implanted. As seen in FIG. 48, the flexure feature 200 may permit translation and/or rotation of the bone engaging features 10, 20 relative to one another. In FIG. 48, the second metatarsal 52 and second bone engaging feature 20 have moved slightly downwardly relative to first metatarsal 51 and first bone engaging feature 10.

When the implant is implanted into the body, the first bone engaging feature 10 is located between the dorsal side of the first metatarsal 51 and the dorsal fascia of the foot, and the second bone engaging feature 20 is located between the dorsal side of the second metatarsal 52 and the dorsal fascia of the foot. In some embodiments, anchor holes are positioned on the bone engaging features such that the bone anchors can be inserted through the bones to attach the bone engaging feature to the bone. The first bone engaging feature 10 may include an anchor hole for receiving a first bone anchor 251, and the second bone engaging feature 20 may include an anchor hole for receiving a second bone anchor 252. Each bone anchor may be inserted through an incision in the dorsal fascia. In some embodiments, one or both of the bone anchors 251, 252 are monocortical anchors—i.e., the anchor penetrates through the metatarsal cortex only once (e.g., through the dorsal cortex), instead of penetrating through the cortex twice.

Figure 50:
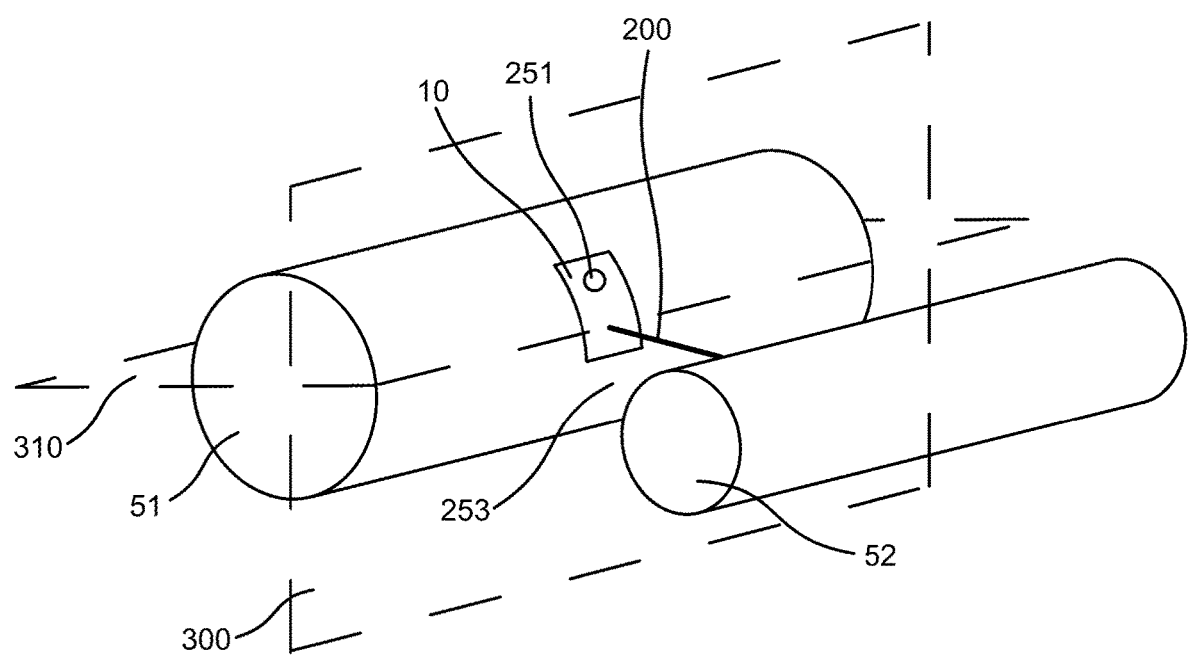
FIG. 50 depicts a perspective view illustrating the use of the implant system of FIG. 49.

According to one aspect, the implant may be constructed and arranged to couple substantially only to bone aspects that face one another. For example, as shown in FIGS. 49 and 50, which depicts the first and second metatarsals of the left foot, the first bone engaging feature 10 is coupled substantially only to the lateral aspect of the first metatarsal 51, and the second bone engaging feature 20 is coupled substantially only to the medial aspect of the second metatarsal 52. In other words, the bone engaging features 10, 20 are coupled substantially only to metatarsal aspects that face one another (the lateral aspect of the first metatarsal faces the medial aspect of the second metatarsal.) The words "substantially only to the medial/lateral aspect" include arrangements where a bone engaging feature also couples to a portion of the dorsal side or ventral side of the bone. As seen in FIGS. 49 and 50, where the implant is constructed and arranged to couple substantially only to bone aspects that face one another, the bone engaging features 10, 20 may be coupled to one another via an intermediate portion 200. In other embodiments, the implant may be constructed and arranged to couple only to bone aspects that face one another, such that the bone engaging feature does not couple to the dorsal or ventral sides of the bones. A bone anchor 251 may be used to attach the first bone engaging feature 10 to the first metatarsal 51 and a second bone anchor 252 may be used to attach the second bone engaging feature 20 to the second metatarsal 52. As with the embodiment shown in FIG. 47, when the implant is engaged to the first and second bones 51, 52, the intermediate portion 200 is positioned substantially between the bones 51, 52 without passing through the bones. Further, no portion of the implant, including any associated bone anchors (such as anchors 251, 252), passes completely through either of the bones 51, 52. In some embodiments, the intermediate portion 200 may include or serve as a flexure feature such as a cable, wire or elastic member. As discussed previously, the flexure feature 200 may couple to coupling points 211, 221 of the bone engaging features 10, 20 via holes 210, 220 in the bone engaging features. In the embodiment shown in FIGS. 49 and 50, only a single bone anchor 251 is used to attach the first bone engaging feature 10 to the first metatarsal 51.

Figure 51:
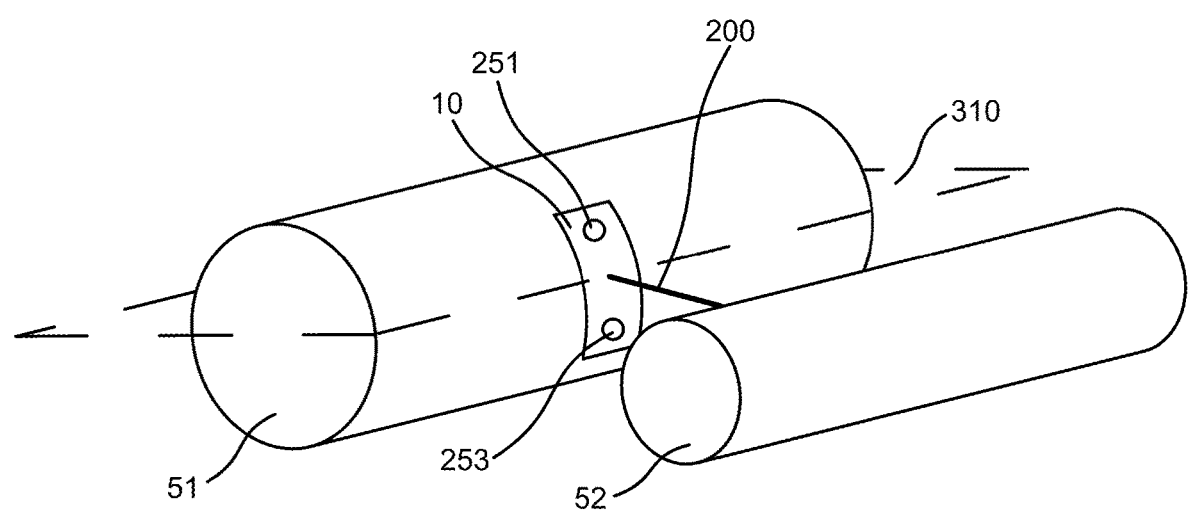
FIG. 51 depicts a top perspective view another exemplary bunion correction implant system.
Figure 52:
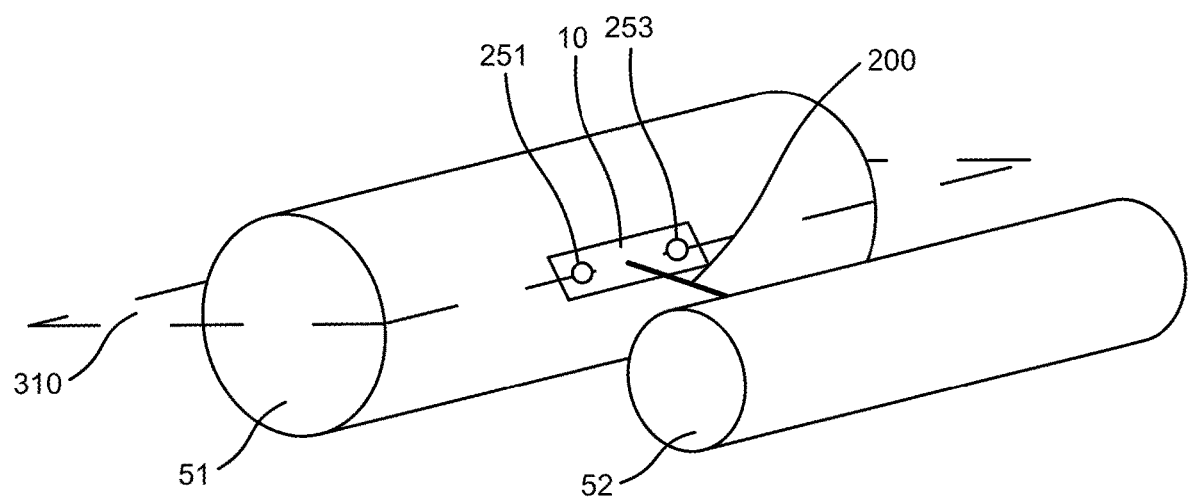
FIG. 52 depicts a top perspective view another exemplary bunion correction implant system.

In other embodiments, such as the embodiments shown in FIGS. 51 and 52, a plurality of bone anchors 251, 253 may be used to attach the first bone engaging feature 10 to the first metatarsal 51. In each of the embodiments shown in FIGS. 51 and 52, the implant is also constructed and arranged to couple substantially only to bone aspects that face one another. In each of the embodiments, the first bone engaging feature 10 is coupled substantially only to the lateral aspect of the first metatarsal 51, and a second bone engaging feature is coupled substantially only to the medial aspect of the second metatarsal 52. In the embodiment shown in FIG. 51, the bone engaging feature 10 extends along the circumference of the bone such that one anchor 251 is positioned above the horizontal plane 310 and one anchor 253 is positioned below the horizontal plane 310. In FIG. 52, the bone engaging feature 10 extends along the length of the bone such that the anchors 251, 253 are substantially aligned in a direction that is parallel to the horizontal plane 310.

The Applicant has recognized that one common failure mode for some bone anchors (such as bone screws) is due to shear loads, and that arranging bone anchors to bear loads in tension may help to decrease the occurrence of such failure modes. The Applicant has also recognized that arranging bone anchors to be placed in the body in a position and orientation that is the most easily accessible to a medical practitioner may help to decrease procedure time and risks of complications. The Applicant has appreciated that arranging bone anchors to bear loads in tension may result in the bone anchors being positioned and/or oriented in a manner that is not easily accessible to a medical practitioner. As such, the Applicant has appreciated the need for a balance between these two considerations. According to one aspect, bone anchors used to attach the implant to the metatarsals are angled in a manner that decreases shear loads on the bone anchors, while simultaneously being accessible by a medical practitioner.

As seen in each of the illustrative embodiments shown in FIGS. 47-49, the anchors 251, 252 are arranged at an angle relative to a vertical plane 300 that bisects one of the metatarsals through the dorsal and ventral sides of the metatarsal. In some embodiments, such an angle may be accomplished by arranging anchor holes on the bone engaging features at a position such that the bone anchors can be inserted through the bones at an angle relative to the vertical axis 300. In other words, in some embodiments, an anchor hole is positioned on a portion of a bone engaging feature that is constructed and arranged to contact or be positioned close to a portion of the bone that is angled away from the vertical plane 300. Such an angle may be achievable by a medical practitioner when inserting the anchor, and/or may allow the medical practitioner to access the anchor if the anchor requires removal. In addition, such an angle may help to decrease the shear loads that the anchor is subjected to. In some embodiments, the bone anchors may be substantially parallel to a horizontal plane 310 that bisects one of the metatarsals through the lateral and medial aspects of the metatarsal. In some embodiments, when the implant device is engaged with the metatarsals, the bone anchors are substantially parallel to the flexure feature 200, which may be a wire. While this aspect discusses positioning anchors at an angle relative to the vertical plane, it should be appreciated that, in other embodiments, the bone anchors may be substantially parallel to the vertical plane 300. In some embodiments, the bone anchors 251, 252 may be located as closely as possible to the coupling points 211, 221 of the bone engaging features 10, 20.

According to certain aspects, a surgical procedure is used to deploy the implant. In some embodiments, when treating a patient with hallux valgus, a standard medial approach for hallux valgus repair may be employed. During the procedure, the surgeon may perform a complete lateral release either through a separate distal approach or through the medial incision. A small incision may be placed just lateral to the second metatarsal, thereby exposing the metatarsal. A fascial elevator may be inserted from the medial aspect of the first metatarsal just proximal to the metaphysis, extending to the lateral aspect of the second metatarsal. As a result, the soft tissue may be elevated to form an envelope. The surgeon may then choose an appropriately sized implant based on the patient's anatomical characteristics. The implant may be inserted into the space provided by the fascial elevator, and may be placed around the second metatarsal. The first metatarsal may then be manually reduced, and the implant may be secured to the first metatarsal with locking or non-locking bone screws or other suitable bone engaging feature. Bone screws or other hardware may be drilled just through the cortex of the bone to a depth of about 1 mm, without fully penetrating through the entire bone. As illustrated in FIGS. 29A and 35, in one embodiment, bone screws or other hardware may be inserted though bone anchor holes 16. An additional screw may be secured dorsally into the second metatarsal. As illustrated in FIG. 25, in one embodiment, the additional screw may be inserted through dorsal bone anchor hole 26. In some embodiments, treatment of tailor's bunion may employ a similar procedure. Of course, it should be appreciated that the present invention is not limited in this respect and other suitable procedures may be employed.

Figure 53:
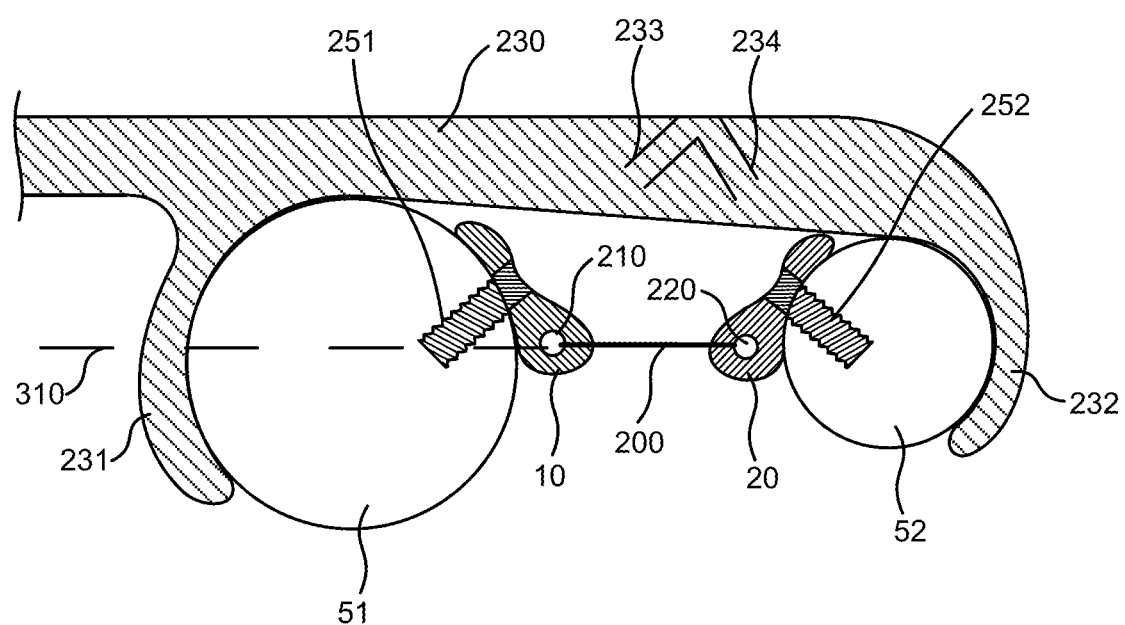
FIG. 53 depicts a side view of an instrument used to deploy a bunion correction implant system of the present disclosure.

According to one aspect, a specially configured instrument may be used to deploy the implant. The instrument may have a clasping mechanism that provides a holding force to keep the metatarsals of interest parallel to each other or in any other desirable configuration while the implant is coupled to the metatarsals. In some embodiments, the instrument holds the metatarsals of interest in place while anchors are used to couple the implant to the metatarsals. As the bone anchors engage metatarsals, the instrument is disengaged from the metatarsals. In one illustrative embodiment, shown in FIG. 53, an instrument 230 has two clasping members 231, 232 that provide a holding force on the metatarsals 51, 52 to keep the metatarsals at a set distance from one another and/or parallel to each other, or in any other desirable configuration while an implant is coupled to the metatarsals. In some embodiments, the instrument 230 has passages 233, 234 through which anchors 251, 252 can be passed such that the anchors 251, 252 can be used to attach the implant to the metatarsals. Once the anchors are in place, the instrument 230 can be disengaged from the metatarsals 51, 52.

According to one aspect, any implant disclosed herein may be positioned on the dorsal side of a bone, such as a metatarsal bone. Alternatively, any implant may be positioned on the ventral side of a bone. Positioning of implants on the dorsal side of the metatarsals may be preferred due to improved patient comfort and less interference with daily activities. In addition, deployment of an implant on the dorsal side of the metatarsals may require a less invasive surgical procedure.

According to one aspect, depending on the extent of the deformity (e.g. large intermetatarsal angle), an implant disclosed herein may be used as an adjunctive device in combination with an additional surgical procedure. Surgical procedures include wedge osteotomy, transpositional osteotomy, fusion, joint replacement, or other suitable surgical procedure, as this aspect is not limited in this regard.

In some embodiments, an implant disclosed herein may remain permanently within the body. In some cases, the implant may be replaced after a certain amount of time. In others, the implant may be bioabsorbable or may be removed after a certain amount of time.

In some embodiments, the implants disclosed herein may be constructed of any biocompatible material such as titanium, nickel, nickel titanium alloy, nitinol or other shape-memory alloy, silver, gold, plastic, or other suitable material. In some embodiments, the material may be substantially rigid, as opposed to elastic. In other embodiments, the material may be elastic. In some cases, the material may be substantially deformable by hand. The implant may be formed from a plate or strip of material that is about 0.7 to about 1.2 millimeters thick and about 5 to about 15 millimeters wide.

According to one aspect, an implant disclosed herein may be formed using any suitable process. The implants may be stamped out of sheet metal or cast from metal and curved at each end by a plate bender or other suitable tool. Any suitable finishing and/or sterilization processes may be applied to the implants, as this aspect is not limited in this regard.

According to one aspect, an implant disclosed herein may have permanent discrete lengths, widths and/or thicknesses. In some embodiments, a range of implants of different sizes may be provided in a kit. For example, in one embodiment, the kit may include a range of five discretely sized implants or implant systems: the first may be suitable for very small patients, the second may be suitable for patients who are somewhat smaller than average, the third may be suitable for average-sized patients, and so on, where the size range of implants or implant systems is scaled (e.g., linearly). In some embodiments, the first implant may have a length of about 32 mm, the second may have a length of about 34 mm, the third implant may have a length of about 36 mm, the fourth implant may have a length of about 38 mm, and the fifth implant may have a length of about 40 mm, for example. In some embodiments, kits may be designed to suit a specific gender, age, and/or severity of deformity. For example, kits for pediatric applications may include smaller implants than kits for adult applications. In some embodiments, kits may also include instruments used to adjust the implants, such as a plate bender. Of course, it should be appreciated that the present disclosure is not limited in this respect and other suitable kits may be employed. For example, the kits may include any number of implants at any range of sizes. In another embodiment, each discretely-sized implant may be provided individually rather than in a collective kit.

The above aspects may be employed in any suitable combination, as the present disclosure is not limited in this respect. Also, any or all of the above aspects may be employed in an implant; however, the present disclosure is not limited in this respect, as the above aspects may be employed with other medical devices.

Also, as described herein, the implants disclosed herein may be used for correction of hallux valgus or tailor's bunion. However, embodiments are not limited to use for correction of hallux valgus, tailor's bunion, or deformities of the foot bones. According to some aspects, the implants and systems may be used in other locations of the body, for example, with the metacarpals of the hand, the radius and ulna of the arm, or the fibula and tibia of the leg, etc., as aspects are not limited in this regard. In addition, while some embodiments disclosed herein may discuss use of a surgical implant with a human subject, the surgical implant may be used in non-human subjects as well, as the invention is not limited in this regard.

The terminology used herein is for the purpose of describing particular embodiments only and is not intended to be limiting of an invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), "contain" (and any form contain, such as "contains" and "containing"), and any other grammatical variant thereof, are open-ended linking verbs. As a result, a method or article that "comprises", "has", "includes" or "contains" one or more steps or elements possesses those one or more steps or elements, but is not limited to possessing only those one or more steps or elements. Likewise, a step of a method or an element of an article that "comprises", "has", "includes" or "contains" one or more features possesses those one or more features, but is not limited to possessing only those one or more features.

As used herein, the terms "comprising," "has," "including," "containing," and other grammatical variants thereof encompass the terms "consisting of" and "consisting essentially of."

The phrase "consisting essentially of" or grammatical variants thereof when/if used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed compositions or methods.

Any publication cited in this specification are herein incorporated by reference as if each individual publication were specifically and individually indicated to be incorporated by reference herein as though fully set forth. Any subject matter incorporated by reference is not considered to be an alternative to any claim limitations, unless otherwise explicitly indicated.

Where one or more ranges are referred to throughout this specification, each range is intended to be a shorthand format for presenting information, where the range is understood to encompass each discrete point within the range as if the same were fully set forth herein. While several aspects and embodiments of the present disclosure have been described and depicted herein, alternative aspects and embodiments may be affected by those skilled in the art to accomplish the same objectives. Accordingly, this disclosure and the appended claims are intended to cover all such further and alternative aspects and embodiments as fall within the true spirit and scope of inventions of the present disclosure.

It is to be understood that the above description is intended to be illustrative, and not restrictive. Numerous changes and modifications may be made herein by one of ordinary skill in the art without departing from the general spirit and scope of the invention as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably connected" is used herein to refer to both connections resulting from separate, distinct components being directly or indirectly coupled and components being integrally formed (i.e., monolithic). Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the disclosure may include only some of the described embodiments. Accordingly, the invention is not to be seen as limited by the foregoing description, but is only limited by the scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An implant system for correcting a bunion, the implant comprising:
    a first bone engaging implant configured to couple to a first bone;
    a second bone engaging implant configured to couple to a second bone that is adjacent the first bone; and
    a flexible cable member extending between the first and second implants that allows motion between the first and second implants, wherein the first and second implants are configured to engage respective metatarsal bones of a foot of the patient to prevent movement of the metatarsal bones away from each other,
    wherein end portions of the flexible cable member are each fixedly coupled within an aperture of a fitting, the fittings being coupled to an inner portion of the first bone engaging implant,
    wherein a loop portion of the flexible cable member extending between the fittings loops through a pair of apertures within an inner portion of the second bone engaging implant,
    where a guide portion of the second bone engaging implant is positioned between the pair of apertures thereof, the guide portion including an inwardly extending arm associated with each of the pair of apertures that guides the loop of the flexible cable member through the inner portion of the second bone engaging implant, and
    wherein a cap member cooperates with an interior side of the guide portion of the second bone engaging implant, the cap member forming a channel between the guide portion that guides the loop of the flexible cable member through the inner portion of the second bone engaging implant.

2. The implant system of claim 1, wherein the length of the flexible cable member extending between the first and second implants is configured to decrease an angle formed between the first and second bones and prevent the angle from increasing.

3. The implant system of claim 1, wherein the length of the flexible cable member extending between the first and second implants is configured to decrease an intermetatarsal angle between the metatarsal bones.

4. The implant system of claim 1, wherein the first bone is a first metatarsal bone and the second bone is a second metatarsal bone.

5. The implant system of claim 1, wherein the first implant is configured to wrap partially around the first bone, and the second implant configured to wrap partially around the second bone.

6. The implant system of claim 1, wherein the first implant includes a first bone engagement surface for engaging the first bone including a first portion defined by a first radius, and the second implant includes a second bone engagement surface for engaging the second bone including a second portion defined by a second radius that is smaller than the first radius, wherein the first portion has a first arc length and the second portion has a second arc length that is smaller than the first arc length.

7. The implant system of claim 1, wherein the first and second bone engaging implants further include at least one bone anchor hole configured to accept at least one anchoring element that anchors the implants to the respective first or second bone.

8. The implant system of claim 1, wherein the flexible cable member allows an angle between the first and second implants to vary, and prevents movement of the first and second implants away from each other along the proximal-distal direction.

9. The implant system of claim 1, wherein the flexible cable member is slidably coupled to the second implant.

10. A method of repositioning a first bone relative to an adjacent second bone, the method comprising:
    coupling the first bone engaging implant of the implant system of claim 1 to the first bone;
    coupling the second bone engaging implant of the implant system of claim 1 to the second bone; and
    coupling the flexible cable member between the first and second implants such that the first bone is drawn towards the second bone,
    wherein the flexible cable member allows motion between the first and second bones but for movement away from each other.

11. The method of claim 10, wherein drawing the first bone toward the second bone decreases an angle formed between the first and second bones, wherein the first bone and the second bone are respective metatarsal bones of the foot of a patient.

12. The implant system of claim 11, wherein the angle is the intermetatarsal angle between the metatarsal bones.

13. The method of claim 10, wherein, when the cable member is coupled between the first and second implants, the flexible cable member allows an angle between the first and second implants to vary.

14. The method of claim 10, wherein coupling the cable member between the first and second implants comprises rigidly coupling the cable member to the first and second implants implant via the fittings and slidably coupling the cable member to the second implant via looping the cable member through the pair of apertures within the inner portion of the second bone engaging implant.

15. The implant system of claim 1, wherein the first bone engaging implant comprises an outer portion, an inner portion and an intermediate portion extending between the outer and inner portions, the first and second portions having differing dorsal-plantar depths as measured from a dorsal-most surface of the first bone engaging implant to a plantar-most surface of each of the outer and inner portions, and wherein the dorsal-plantar depth of the outer portion is greater than the dorsal-plantar depth of the inner portion of the first bone engaging implant.

16. The implant system of claim 15, wherein the second bone engaging implant comprises an outer portion, an inner portion and an intermediate portion extending between the outer and inner portions, the first and second portions having differing dorsal-plantar depths as measured from a dorsal-most surface of the second bone engaging implant to a plantar-most surface of each of the outer and inner portions, and wherein the dorsal-plantar depth of the outer portion is greater than the dorsal-plantar depth of the inner portion of the second bone engaging implant.

17. The implant system of claim 16, wherein the dorsal-plantar depth of the outer portion is greater than the dorsal-plantar depth of the inner portion of the second bone engaging implant by a lesser degree than the dorsal-plantar depth of the outer portion is greater than the dorsal-plantar depth of the inner portion of the first bone engaging implant.

18. The implant system of claim 1, wherein the first bone engaging implant comprises an outer portion, an inner portion and an intermediate portion extending between the outer and inner portions, and wherein the outer and intermediate portions of the first bone engaging implant both include a plurality of bone anchor holes configured to accept at least one anchoring element therethrough and into the first bone.

19. The implant system of claim 18, wherein the second bone engaging implant comprises an outer portion, an inner portion and an intermediate portion extending between the outer and inner portions, and wherein the intermediate portion of the second bone engaging implant includes a plurality of bone anchor holes, and the outer portion of the second bone engaging implant includes a singular bone anchor hole, that are configured to accept at least one anchoring element therethrough and into the second bone.

20. An implant for repositioning bones of a patient, the implant comprising:
a first bone engaging implant configured to engage a portion of an outer surface of a first bone;
a second bone engaging implant configured to o engage a portion of an outer surface of a second bone; and
an intermediate portion connecting the first and second bone engaging implants, the intermediate portion and the first and second bone engaging implants cooperating to enable the first bone to be drawn toward the second bone,
wherein end portions of the intermediate member are each fixedly coupled within an aperture of a fitting, the fittings being coupled to an inner portion of the first bone engaging implant,
wherein a loop portion of the intermediate member extending between the fittings loops through a pair of apertures within an inner portion of the second bone engaging implant,
where a guide portion of the second bone engaging implant is positioned between the pair of apertures thereof, the guide portion including an inwardly extending arm associated with each of the pair of apertures that guides the loop of the intermediate member through the inner portion of the second bone engaging implant,
wherein a cap member cooperates with an interior side of the guide portion of the second bone engaging implant, the cap member forming a channel between the guide portion that guides the loop of the intermediate member through the inner portion of the second bone engaging implant,
wherein the intermediate portion prevents movement of the first and second bone engaging implants away from each other to prevent the first and second bones from moving away from each other,
wherein the first bone engaging implant comprises an outer portion, the inner portion and an intermediate portion extending between the outer and inner portions, the inner and outer portions having differing dorsal-plantar depths as measured from a dorsal-most surface of the first bone engaging implant to a plantar-most surface of each of the outer and inner portions, and wherein the dorsal-plantar depth of the outer portion is greater than the dorsal-plantar depth of the inner portion of the first bone engaging implant.

* * * * *